US012662514B2

(12) United States Patent
Heck et al.

(10) Patent No.: US 12,662,514 B2
(45) Date of Patent: Jun. 23, 2026

(54) METHODS TO BLOCK APHID TRANSMISSION OF POLEROVIRUSES AND TO DEVELOP VIRUS MANAGEMENT TOOLS

(71) Applicant: The United States of America, as represented by The Secretary of Agriculture, Washington, DC (US)

(72) Inventors: Michelle L. Heck, Ithaca, NY (US); Jennifer R. Wilson, Ithaca, NY (US); Carl J. Schiltz, Joelton, TN (US); Joshua S. Chappie, Ithaca, NY (US); Myfanwy C. Adams, Ithaca, NY (US)

(73) Assignees: The United States of America, as represented by The Secretary of Agriculture, Washington, DC (US); Cornell University, Ithaca, NY (US)

( * ) Notice: Subject to any disclaimer, the term of this patent is extended or adjusted under 35 U.S.C. 154(b) by 90 days.

(21) Appl. No.: 18/066,191

(22) Filed: Dec. 14, 2022

(65) Prior Publication Data

US 2023/0272413 A1     Aug. 31, 2023

Related U.S. Application Data

(60) Provisional application No. 63/289,790, filed on Dec. 15, 2021.

(51) Int. Cl.
| | |
|---|---|
| *C07K 14/005* | (2006.01) |
| *A01N 63/50* | (2020.01) |
| *C07K 16/10* | (2006.01) |
| *C12N 7/00* | (2006.01) |
| *C12N 15/82* | (2006.01) |
| *G01N 33/569* | (2006.01) |

(52) U.S. Cl.
CPC ............ *C07K 14/005* (2013.01); *A01N 63/50* (2020.01); *C07K 16/10* (2013.01); *C12N 7/00* (2013.01); *C12N 15/8286* (2013.01); *G01N 33/56983* (2013.01); *C07K 2317/569* (2013.01); *C12N 2770/00021* (2013.01); *C12N 2770/00022* (2013.01); *G01N 2333/08* (2013.01)

(58) Field of Classification Search
None
See application file for complete search history.

(56) References Cited

FOREIGN PATENT DOCUMENTS

WO      2021095031 A2      5/2021

OTHER PUBLICATIONS

Casteel et. al., 2015. GeneBank Accession No. AJY53724 (Oct. 31, 2014) (Year: 2014).*
Boissinot et al., Both Structural and Non-Structural Forms of the Readthrough Protein of Cucurbit aphid-borne yellows virus Are Essential for Efficient Systemic Infection of Plants, 2014, PLoS ONE, 9(4):e93448 (Year: 2014).*
Bakhsh A., Development of efficient, reproducible and stable agrobacterium—mediated genetic transformation of five potato cultivars, Food Technology and Biotechnology, 2020, 58:57-63 (Year: 2020).*
Fung et. al., Targeting and processing of membrane-anchored YFP fusion proteins to protein storage vacuoles in transgenic tobacco seeds, Seed Science Research (2005) 15, 361-364. (Year: 2005).*
Xu et al., A Stem-Loop Structure in Potato Leafroll Virus Open Reading Frame 5 (ORF5) Is Essential for Readthrough Translation of the Coat Protein ORF Stop Codon 700 Bases Upstream, 2018, J Virol., 92:e01544-1). (Year: 2018).*
Boissinot et al., Both Structural and Non-Structural Forms of the Readthrough Protein of Cucurbit aphid-borne yellows virus Are Essential for Efficient Systemic Infection of Plants, 2014, PLoS ONE, 9:e93448 (Year: 2014).*
Xu et al., A Stem-Loop Structure in Potato Leafroll Virus Open Reading Frame 5 (ORF5) Is Essential for Readthrough Translation of the Coat Protein ORF Stop Codon 700 Bases Upstream, 2018, Journal of Virology, 92:e01544-17) (Year: 2018).*
International Search Report on PCT/US2022/081631 dated Dec. 15, 2022.
NCBI, Gen Bank accession No. CAA54536. I (Jul. 30, 1997) Definition; and sequence.
Liu, S. et al., A peptide that binds the pea aphid gut impedes entry of Pea enation mosaic virus into the aphid hemocoel, Virology, 2010, vol. 401, pp. 107-116.
Uchi, N. et al., Antimicrobial Activities of Cysteine-rich Peptides Specific to Bacteriocytes of the Pea Aphid Acyrthosiphon pisum, Microbes Environ., 2019, vol. 34, No. 2, pp. 155-160.
Brault, V. et al., The Polerovirus Minor Capsid Protein Determines Vector Specificity and Intestinal Tropism in the Aphid, Journal of Virology, 2005, vol. 79, No. 15, pp. 9685-9693.
Boissinot, S. et al., Both Structural and Non-Structural Forms of the Readthrough Protein of Cucurbit aphid-bome yellows virus Are Essential for Efficient Systemic Infection of Plants, PLOS ONE, I Apr. 2014, vol. 9, Issue 4, Article e93448, pp. 1-10.

* cited by examiner

*Primary Examiner* — Bratislav Stankovic
*Assistant Examiner* — Jay Chatterjee
(74) *Attorney, Agent, or Firm* — John Fado; Mark McNemar

(57) ABSTRACT

Disclosed herein are plant-based, molecular and diagnostic tools that can be used to block aphid transmission of poleroviruses, including stabilized proteins for expression in transgenic plants and/or in formulations for direct plant delivery. Further disclosed are proteins that can kill aphids and methods to produce these proteins. Antibodies and useful for diagnostic and therapeutic uses against poleroviruses.

18 Claims, 23 Drawing Sheets

Specification includes a Sequence Listing.

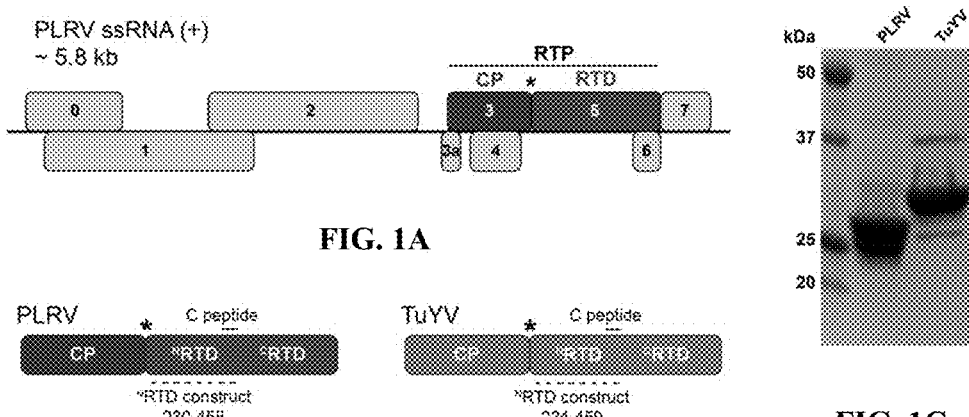
FIG. 1A
FIG. 1B
FIG. 1C
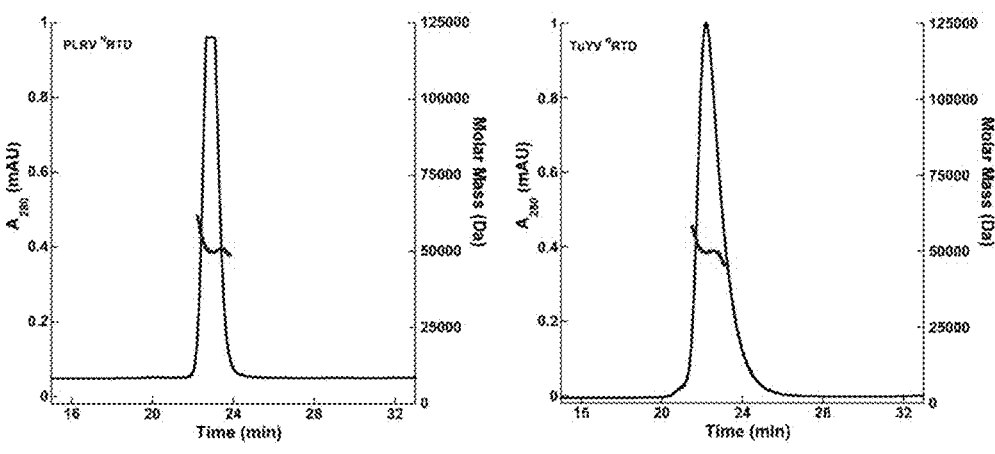
FIG. 1D
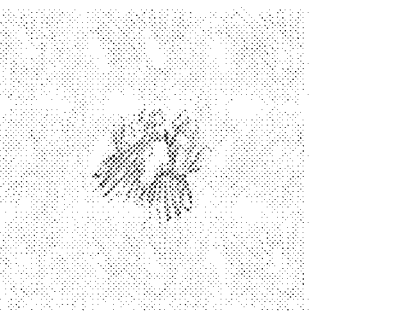
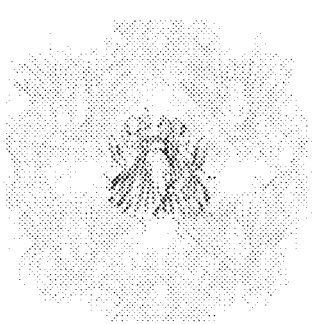
FIG. 1E                                    FIG. 1F

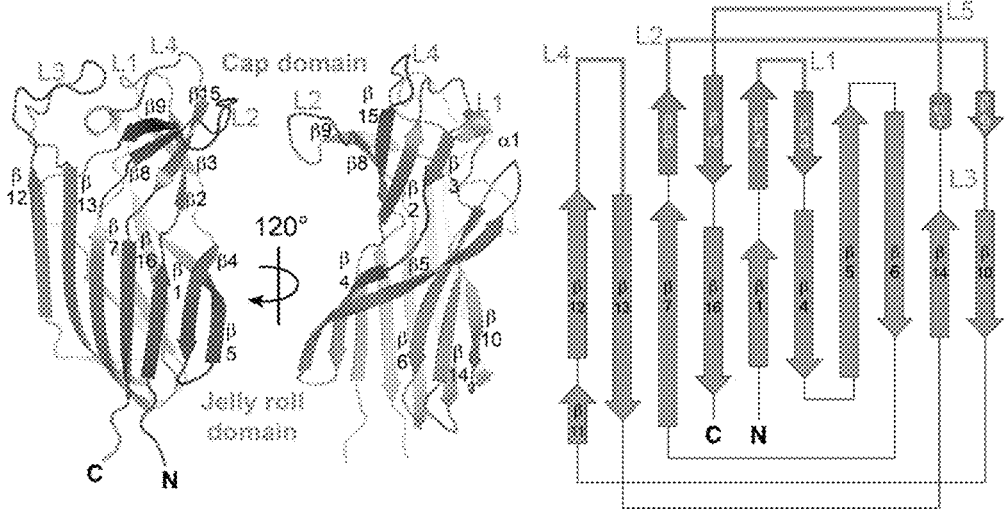
FIG. 3A                    FIG. 3B
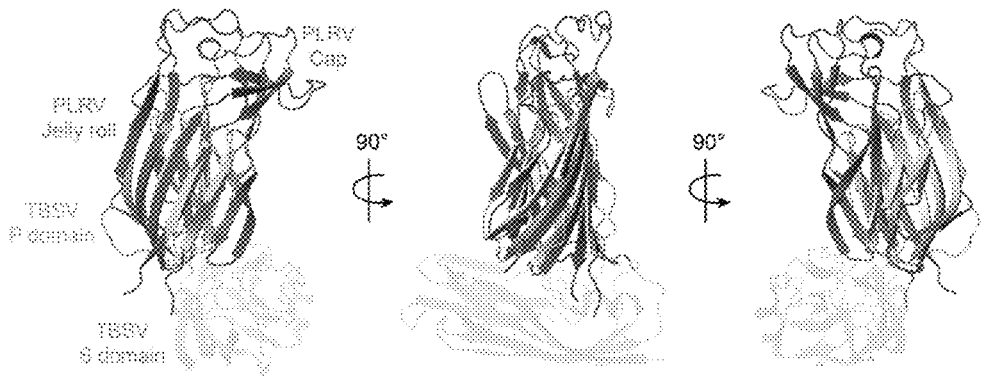
FIG. 3C
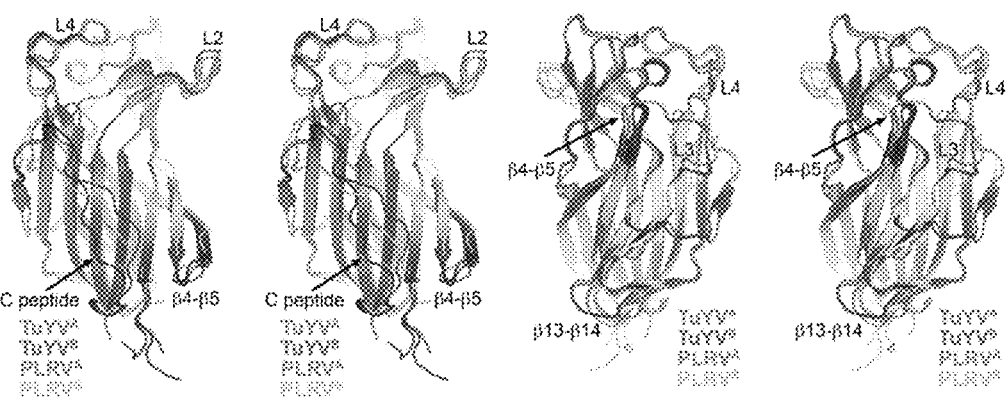
FIG. 3D

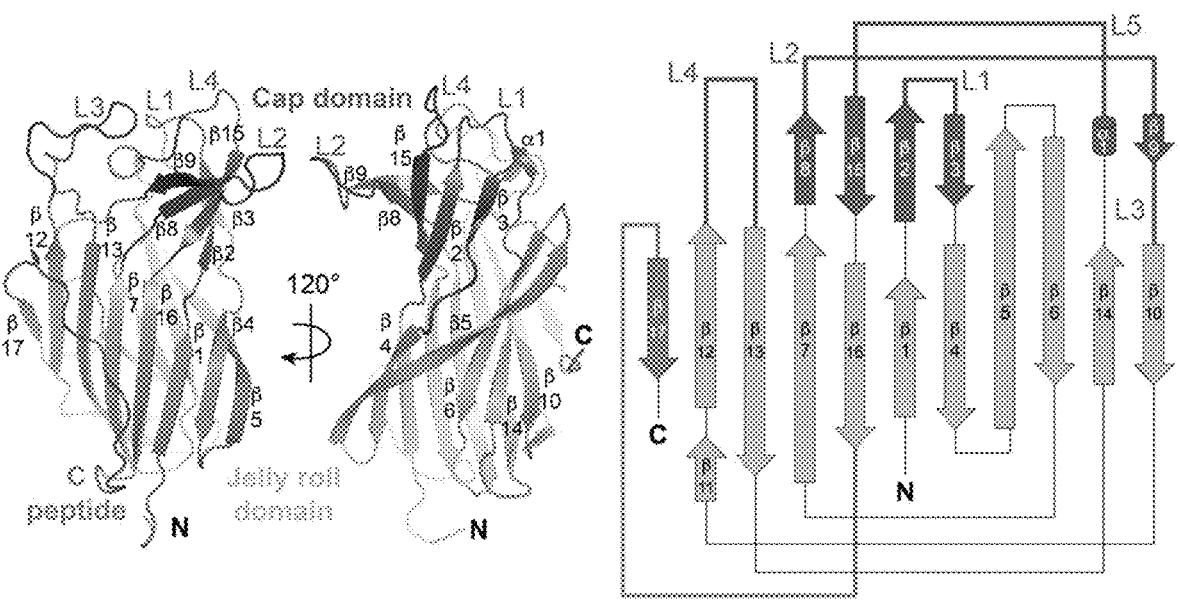
FIG. 4A                                                    FIG. 4B
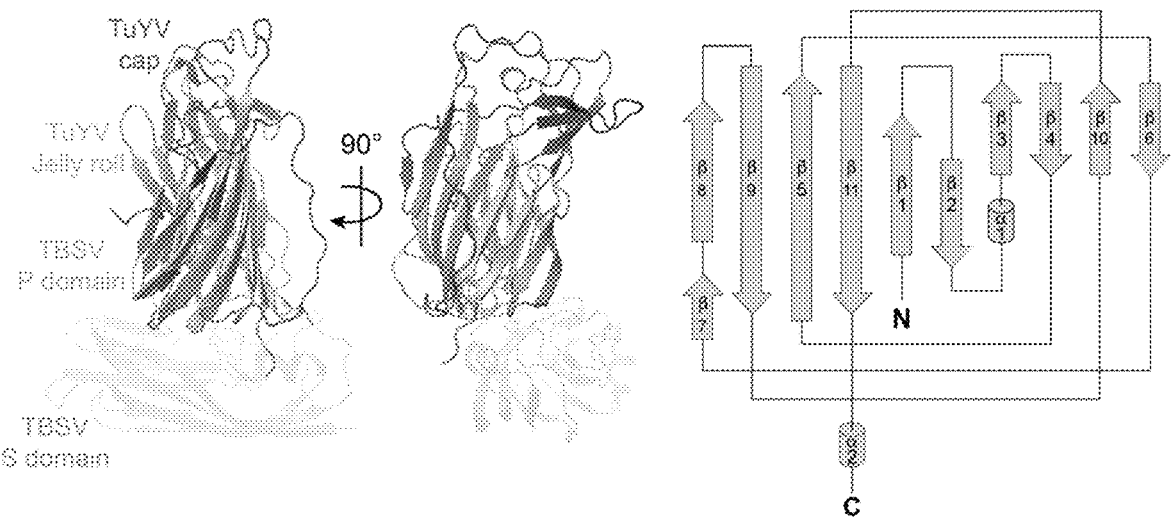
FIG. 4C                                                    FIG. 4D

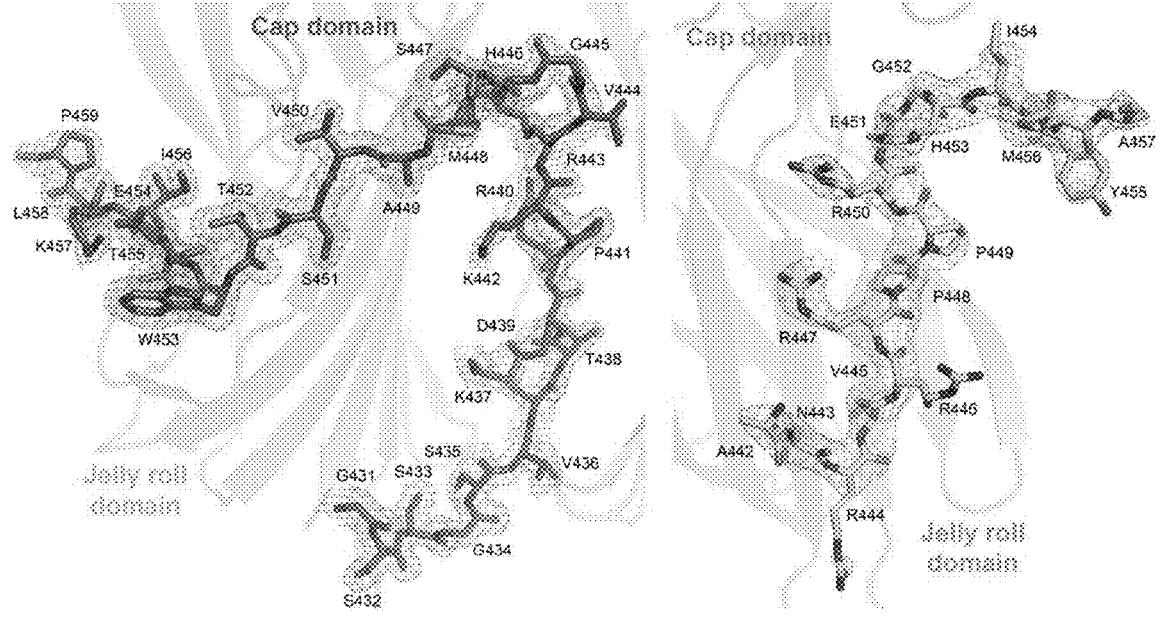
FIG. 6A                              FIG. 6B
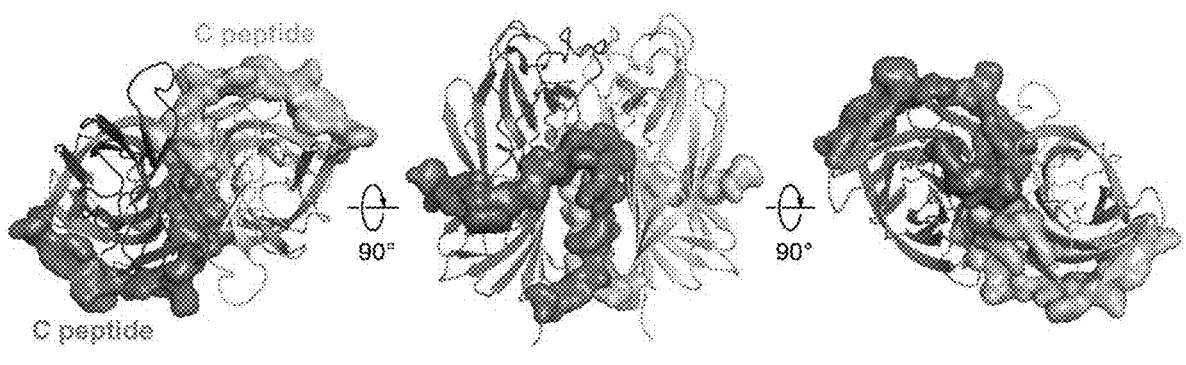
FIG. 6C

FIG. 8B                    FIG. 8E

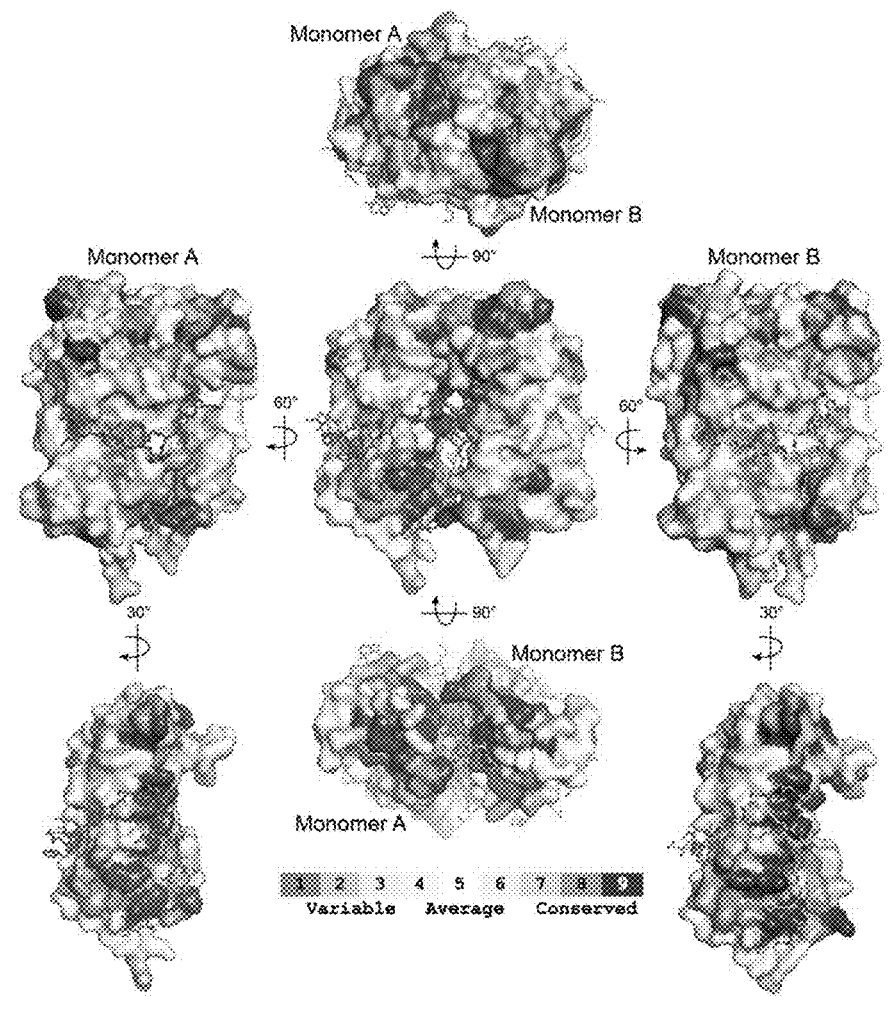
FIG. 9A
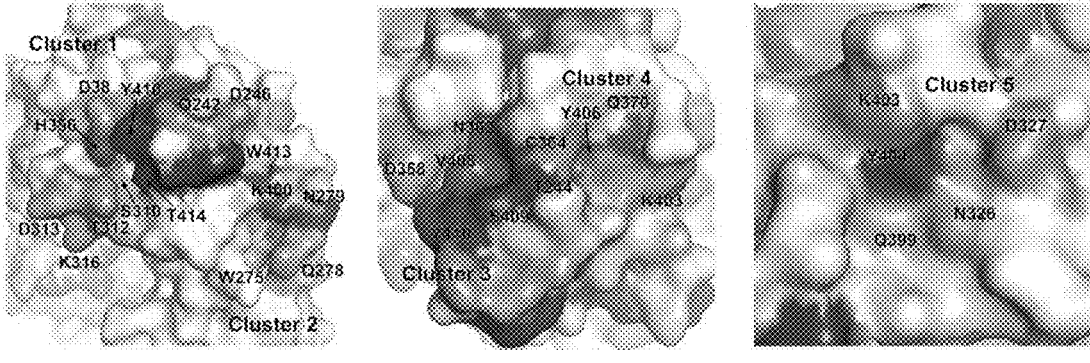
FIG. 9B                    FIG. 9C                    FIG. 9D

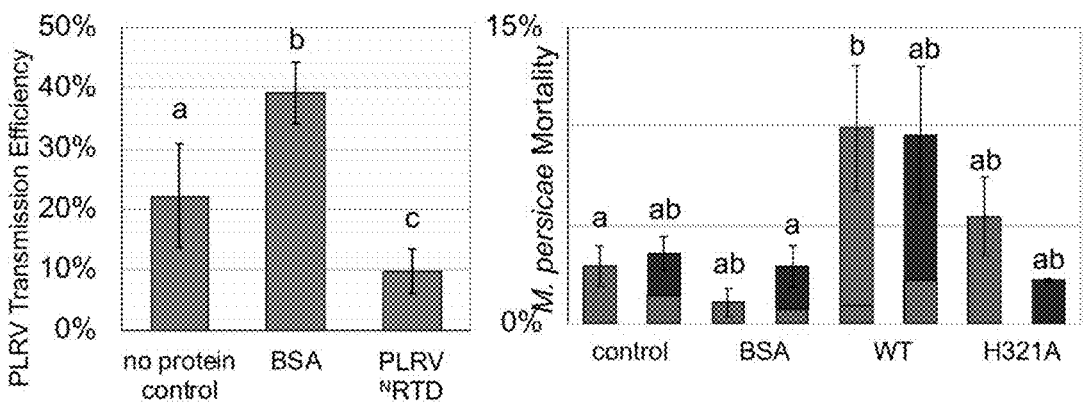
FIG. 12A                    FIG. 12B
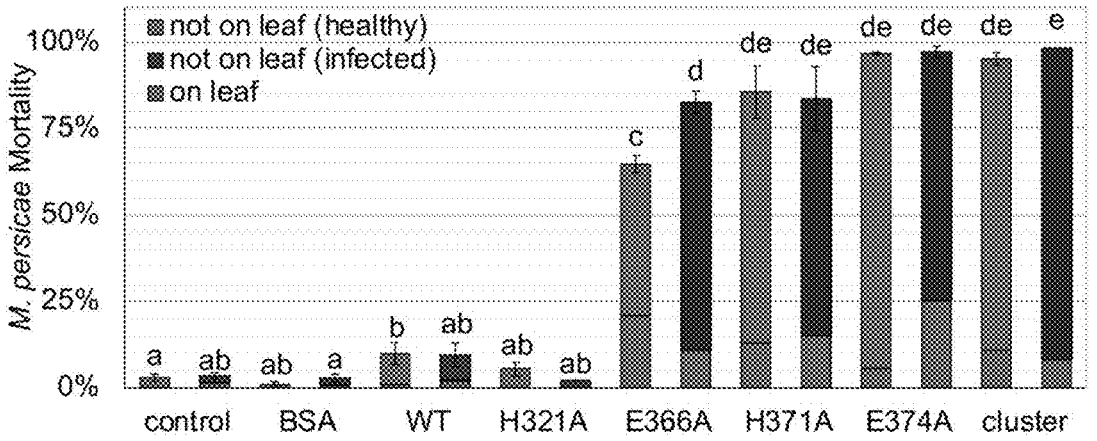
FIG. 12C
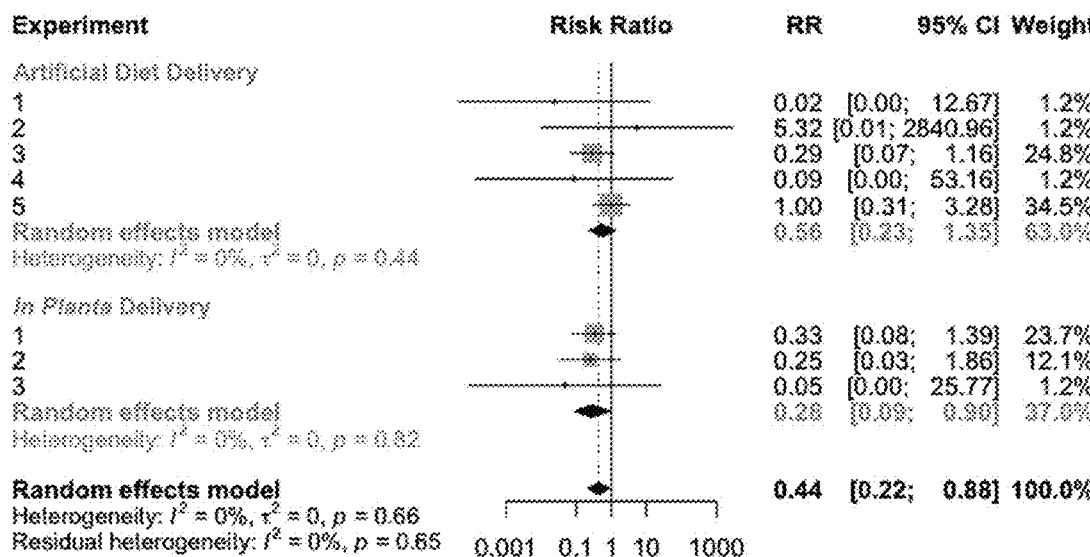
FIG. 12D

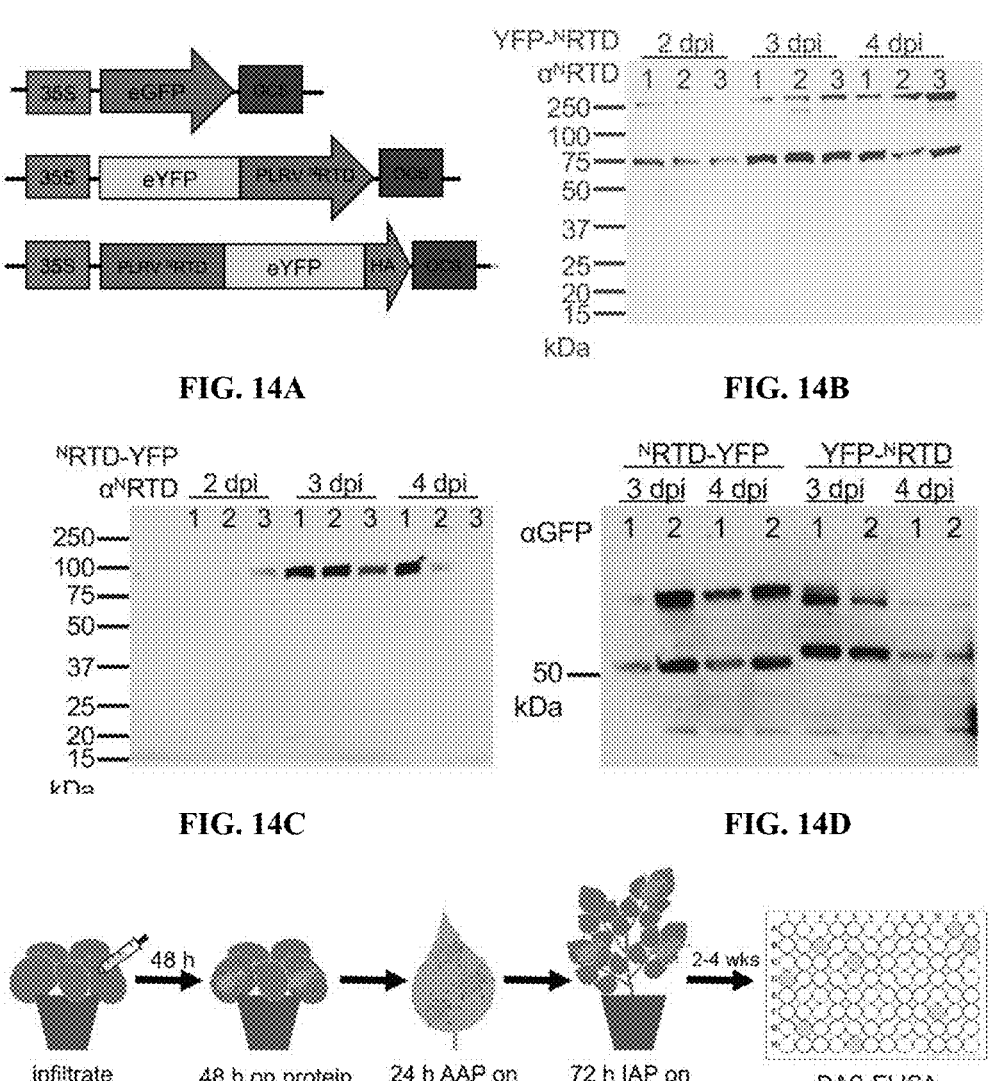
FIG. 14A
FIG. 14B
FIG. 14C
FIG. 14D
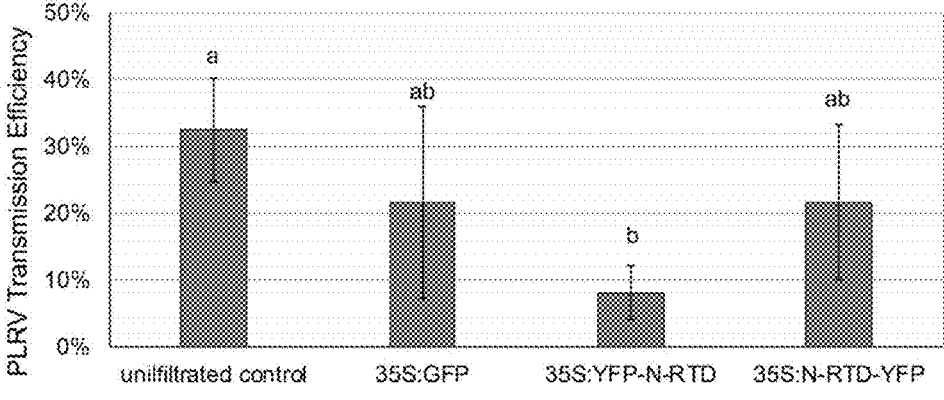
FIG. 14E
FIG. 14F

48 h on
artificial diet
with proteins 24 h AAP on
PLRV-infected
detached leaf

OR 24 h AAP on
uninfected
detached leaf

Assess aphid
mortality and
dispersal

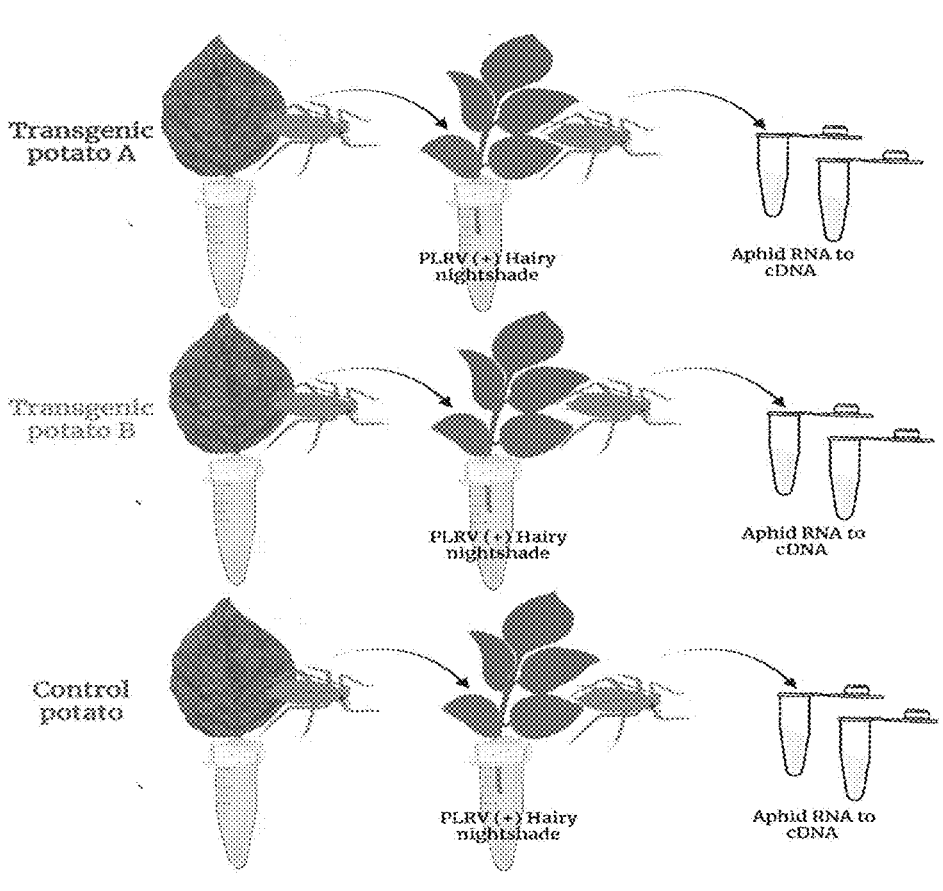
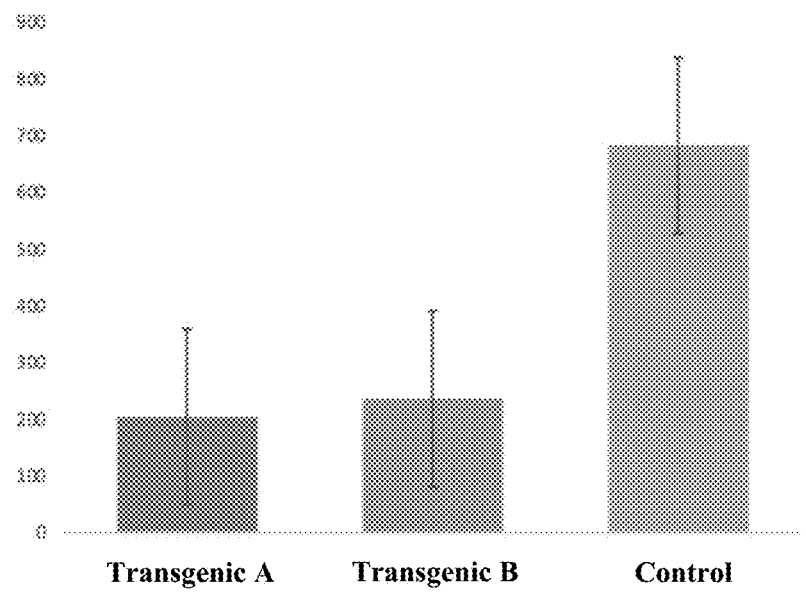
FIG. 19

| BSA, 1 mg/mL | |
| Purified PLRV N~RTD, 100 ug/mL | ● |
| PLRV infected Hairy nightshade | ● |
| Healthy Hairy nightshade | |

FIG. 20

METHODS TO BLOCK APHID TRANSMISSION OF POLEROVIRUSES AND TO DEVELOP VIRUS MANAGEMENT TOOLS

CROSS-REFERENCE

The present application claims priority to U.S. Provisional Patent Application Ser. No. 63/289,790 filed Dec. 15, 2021, the contents of which are expressly incorporated herein by reference.

SEQUENCE LISTING

The instant application contains a Sequence Listing XML required by 37 C.F.R. § 1.831(a) which has been submitted in XML file format via the USPTO patent electronic filing system and is hereby incorporated by reference in its entirety. The XML file was created on Dec. 13, 2022, is named Sequence_Listing_CONVERSION-006721.xml, and has 81.8 KB bytes.

BACKGROUND OF THE INVENTION

Field of Invention

Disclosed herein are plant-based, molecular and diagnostic tools that can be used to block aphid transmission of poleroviruses, including stabilized proteins for expression in transgenic plants and/or in formulations for direct plant delivery. Further disclosed are proteins that can kill aphids, methods to produce these proteins and antibodies useful for diagnostic and therapeutic uses against poleroviruses.

Background

The genus Polerovirus (Family: Solemoviridae) encompasses plant viruses capable of infecting most major crop and biofuel plants. Poleroviruses are unusual among plant pathogens in that they remain confined to the vasculature of plant tissue, specifically the phloem, where they are acquired and later transmitted exclusively by sap-feeding aphid vectors and in one documented instance, whiteflies. Along with related enamoviruses (Family: Solemoviridae) and luteoviruses (Family: Tombusviridae) (with all three genera collectively referred to as P/E/L viruses), poleroviruses have a ~5.8 kb single-stranded positive-sense RNA genome, encoding nine known proteins. Poleroviruses move systemically in both plant hosts and aphid vectors as icosahedral virions. They share a conserved arrangement of open reading frames in the 3' half of their genome, including those that encode the structural proteins.

ORF3 encodes the coat protein (CP), which constitutes the major component of the viral capsid. Ribosomal readthrough of the CP stop codon generates a second minor capsid component—termed the readthrough protein (RTP)—that contains an additional readthrough domain (RTD) encoded by ORF5 fused to its C-terminus codon. The RTD itself is not required for particle assembly or plant infection but plays an important role in aphid transmission. There are two biologically active forms of the RTP: one that becomes incorporated into virions and a second, soluble form that is not in the capsid. The incorporated form regulates long-distance movement in plants and is required for aphid transmission, while the soluble form regulates phloem-retention and virus systemic movement in planta. Virus mutants which abolish the stop codon are not infectious and do not form particles, but the role of $^N$RTD incorporation and folding in hampering virion formation in these mutants is not known.

P/E/L viruses all share a common circulative pathway within their aphid vectors. While the aphid is feeding on the plant phloem, viruses are ingested and acquired through the aphid gut. Each P/E/L virus species is transmitted efficiently by only one or a few aphid species. During acquisition, different virus species display different affinities to various regions of the gut (i.e., midgut or hindgut). Potato leafroll virus (PLRV, Polerovirus) is acquired into midgut epithelial cells, while the yellow dwarf viruses are acquired by the hindgut. Virus particles lacking the RTD are not transmissible by aphids because they do not get endocytosed into the aphid gut efficiently. The RTD is also required for uptake by the accessory salivary glands. Aphids that acquire P/E/L viruses from an infected plant can carry the virus and remain competent for transmission for their entire life. There are no natural, durable sources of plant resistance to P/E/L virus infection in plants. Thus, there is a need for a method to block transmission of these viruses by aphids.

The process of accurately diagnosing a P/E/L virus infection requires detection of the viral RNA genome or proteins produced by the viral RNA. Detection of the viral genome requires reverse transcription coupled to polymerase chain reaction, a highly technical process that involves trained laboratory personnel and access to a molecular biology laboratory. There is need for protein-based diagnostics that growers and extension agents can use in the field with no access to sophisticated laboratory equipment.

All publications, patents and patent applications mentioned in this specification are herein incorporated by reference to the same extent as if each individual publication, patent or patent application was specifically and individually indicated to be incorporated by reference.

SUMMARY OF THE INVENTION

The present disclosure provides isolated proteins having the sequences disclosed as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12. In some embodiments, such proteins are recombinantly modified to comprise a green-fluorescent protein (GFP), a yellow fluorescent protein (YFP), strep tag, FlAsH tag, or polyhistidine (HIS) tag.

The present disclosure also provides a vector comprising a nucleic acid encoding a protein having SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

Further provided herein are recombinant potato leaf roll viruses expressing proteins having the sequence provided in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

Also provided herein are modified proteins comprising a polypeptide having at least 95% identity to SEQ ID NO: 2 or 95% identity to SEQ ID NO: 3, wherein the modified protein comprises an amino acid substitution in any one of residues 137, 138, 139, 140, 141, 142, 143, 144, or 145. In an embodiment of this aspect, the polypeptide has at least 95% identity to SEQ ID NO: 2 and the modified protein comprises an amino acid substitution in any one of residues 137, 138, 139, 140, 141, 142, 143, 144, or 145. In specific embodiments of this modified SEQ ID NO: 2, the amino acid substitution comprises an alanine substitution. In another embodiment of this aspect of the disclosure, the polypeptide has at least 95% identity to SEQ ID NO: 3 and the modified protein comprises an amino acid substitution in any one of residues 137, 138, 139, 140, 141, 142, 143, 144, or 145. In specific embodiments of this modified SEQ ID NO: 3, the amino acid substitution comprises an alanine substitution.

The present disclosure further provides transgenic plants comprising a heterologous nucleic acid encoding SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, the heterologous nucleic acid is operatively linked to a plant promoter sequence.

Also provided herein are plants comprising a protein having the amino acid sequence of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

An additional embodiment disclosed herein are nanobodies having the amino acid sequence of SEQ ID NO: 15, SEQ ID NO: 16, or SEQ ID NO: 17.

The present disclosure additionally provides a method of controlling aphids, where the method has at least the steps of exposing an aphid to a protein having an amino acid sequence: 1) at least 95% identical to SEQ ID NO: 2 and has an amino acid substitution in at least one of residues 137, 138, 139, 140, 141, 142, 143, 144, or 145; or 2) at least 95% identical to SEQ ID NO: 3 and has an amino acid substitution in any one of residues 137, 138, 139, 140, 141, 142, 143, 144, or 145, and inducing increased mortality in the aphid due to exposure. In some embodiments, the protein utilized has the amino acid sequence of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, other than the amino acid substitution. In particular embodiments of this method, the exposing step comprises an aphid feeding on a plant containing the protein.

An additional method disclosed herein is decreasing potato leaf roll virus (PLRV) titer in an aphid, comprising at least the steps of: exposing an aphid to a protein having an amino acid sequence: 1) at least 95% identical to SEQ ID NO: 2 and wherein the protein comprises an amino acid substitution in at least one of residues 137, 138, 139, 140, 141, 142, 143, 144, or 145; or 2) at least 95% identical to SEQ ID NO: 3 and has an amino acid substitution in any one of residues 137, 138, 139, 140, 141, 142, 143, 144, or 145, thereby decreasing PLRV titer in the aphid. In some versions of this method, the exposing step is an aphid feeding on a plant containing the protein. In some embodiments, the protein utilized has the amino acid sequence of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, other than the amino acid substitution.

The present disclosure further provides a method for detecting potato leaf roll virus (PLRV) in a sample, comprising the steps of: (i) incubating a sample with the nanobody having the amino acid sequence of SEQ ID NO: 15, SEQ ID NO: 16, or SEQ ID NO: 17; and (ii) detecting an immunological complex comprising the nanobody and PLRV, wherein the presence or absence of the immunological complex indicates the presence or absence of PLRV in the sample. Samples for such methods can come from, for example, plants or aphids.

BRIEF DESCRIPTION OF THE DRAWINGS

The novel features of the invention are set forth with particularity in the claims. Features and advantages of the present invention are referred to in the following detailed description, and the accompanying drawings of which:

FIG. 1A, FIG. 1B, FIG. 1C, FIG. 1D, FIG. 1E, and FIG. 1F provide pictorial representation of polerovirus $^N$RTD construct designs and data describing the purification and characterization of $^N$RTD construct oligomeric states in solution. FIG. 1A, PLRV genome arrangement with the open reading frames (ORFs) numbered. ORFs 3 (coat protein, CP; blue) and 5 (readthrough domain, RTD; green) together encode the viral readthrough protein (RTP). FIG. 1B, Design of PLRV (left) and TuYV (right) $^N$RTD protein constructs. Dashed lines indicate the location of each $^N$RTD construct relative to the rest of the RTD. Solid black lines denote the positions of the C peptide. Numbering indicates the amino acid residues at the boundaries of each construct. FIG. 1C, SDS-PAGE gel of purified PLRV and TuYV $^N$RTD constructs. FIG. 1D, Size exclusion chromatography coupled to multi-angle light scattering (SEC-MALS) analysis of PLRV (left) and TuYV (right) $^N$RTD constructs indicating each forms a stable dimer in solution. Black line denotes UV trace and blue line denotes measured mass across each peak. Calculated molecular weights of PLRV and TuYV $^N$RTD monomers are 26.4 kDa and 27.1 kDa, respectively. FIG. 1E, Crystal packing of PLRV $^N$RTD. Dimer is colored light blue. FIG. 1F, Crystal packing of TuYV $^N$RTD. Dimer is colored light blue.

FIG. 2A, FIG. 2B, FIG. 2C, FIG. 2D, and FIG. 2E provide pictorial representation of the subunit organization and symmetry of PLRV and TBSV viral capsids. FIG. 2A, T=3 icosahedral symmetry of PLRV capsid (PDB: 6SCO). Individual subunits that constitute the icosahedral asymmetric unit (black triangles) are colored raspberry, light green, and sky blue respectively. 2-, 3-, and 5-fold symmetry axes are marked with a yellow ellipse, yellow triangles, and yellow pentagons, respectively. FIG. 2B, Top and side views of the isolated PLRV asymmetric unit. The PLRV coat protein (CP) is labeled. FIG. 2C, T=3 icosahedral symmetry of TBSV capsid (PDB: 1TBV). Individual subunits that constitute the icosahedral asymmetric unit are colored as in (FIG. 1A). FIG. 2D, Top and side views of the TBSV asymmetric unit. S and P domains are labeled. FIG. 2E, Superposition of PLRV CP (lime) and TBSV S domain (teal) monomers.

FIG. 3A, FIG. 3B, FIG. 3C, and FIG. 3D provide pictorial representation of structure and topology of the PLRV $^N$RTD and its comparison to the full-length coat protein from Tomato bushy stunt virus (TBSV) and the Turnip Yellows Virus (TuYV) $^N$RTD. Structure (FIG. 3A) and topology (FIG. 3B) of PLRV $^N$RTD with jelly roll domain (red), cap domain (blue) labeled. Cap domain loops are labeled L1-L5. FIG. 3C, Superposition of PLRV $^N$RTD and TBSV coat protein (PDB: 2TBV; sequence identity: 4% (across the P domain); DALI14 Z score: 8.3; RMSD: 2.5 Å; P domain, light green, S domain, teal). FIG. 3D, Superposition of TuYV (marine and red) and PLRV (olive and blue-white) $^N$RTD monomers shown in stereo in two orientations. Segments exhibiting conformational differences are labeled in black.

FIG. 4A, FIG. 4B, FIG. 4C, and FIG. 4D provide pictorial representation of structure and topology of the Turnip Yellows Virus (TuYV) $^N$RTD. Structure (FIG. 4A) and topology (FIG. 4B) of TuYV $^N$RTD with jelly roll domain (orange), cap domain (purple) and C peptide (marine) labeled. Cap domain loops are labeled L1-L5. FIG. 4C, Superposition of TuYV $^N$RTD with Tomato bushy stunt virus (TBSV) coat protein (PDB: 2TBV; sequence identity: 9% (across the P domain); DALI Z score: 7.0; RMSD: 2.7 Å; P domain, light green; S domain, teal). FIG. 4D, Topology of TBSV P domain.

FIG. 5A, TuYV $^N$RTD cap domain (purple) shares a conserved β-barrel fold that is present in a wide array of proteins. Structural representatives are shown with associated PDB codes. FIG. 5B, Superposition of β-barrel domains shown in stereo with individual models colored as in FIG. 5A. FIG. 5C, Topology diagrams of conserved β-barrel domains depicted in FIG. 5A and FIG. 5B.

FIG. 6A, FIG. 6B, and FIG. 6C provide pictorial representation of the resolved electron density and localization of the C peptide in polerovirus $^N$RTD structures. 2fo-fc electron density (gray mesh) associated with the C peptide in TuYV (FIG. 6A) and PLRV (FIG. 6B) crystal structures contoured to 1σ. The modeled C peptide residues are colored marine and yellow in TuYV (FIG. 6B) and PLRV (FIG. 6B), respectively. FIG. 6C, Segmented surface representation of the C peptides in the context of the TuYV $^N$RTD dimer. Individual structural segments are colored as follows: Jelly roll domains, orange and light orange; cap domains, purple and light pink; C peptides, marine and light blue Monomers are colored as in FIG. 7A. Top (left), side (middle), and bottom (right) views of the dimer are depicted.

FIG. 7C and FIG. 7D: Slice sections through the dimer at the levels indicated by the solid lines in (FIG. 7A) highlighting stabilizing interactions at the dimer interface. Dashed black lines denote hydrogen bonds. Key residues are labeled with a superscript (A or B) to indicate from which monomer they originate. Secondary structure elements (see FIG. 4A and FIG. 4B) are labeled where applicable. FIG. 7E, C peptide interactions. Residues contributing hydrogen bonding (dashed black lines) and hydrophobic contacts are labeled.

FIG. 8A, FIG. 8B, FIG. 8C, FIG. 8D, and FIG. 8E provide pictorial representation of the architecture of the PLRV $^N$RTD dimer. Cartoon (FIG. 8A) and surface (FIG. 8B) representations of the PLRV $^N$RTD dimer. Individual structural segments are labeled in each monomer and colored as follows: Jelly roll domains, salmon and raspberry; cap domains, light blue and dark blue; C peptide, yellow. FIG. 8C, Slice section through the dimer at the level indicated by the solid line in (FIG. 8A) highlighting stabilizing interactions at the dimer interface. Dashed black lines denote hydrogen bonds. Key residues are labeled with a superscript (A or B) to indicate from which monomer they originate. Secondary structure elements (see FIG. 3A and FIG. 3B) are labeled where applicable. FIG. 8D, Additional stabilized interactions occurring in trans at the upper side of the PLRV dimer. FIG. 8E, C peptide interactions. Residues contributing hydrogen bonding (dashed black lines) and hydrophobic contacts are labeled.

FIG. 9A, FIG. 9B, FIG. 9C, and FIG. 9D provide pictorial representation of structural mapping of P/E/L virus sequence conservation. FIG. 9A, Conservation of $^N$RTD surface exposed residues. Multiple orientations of the TuYV $^N$RTD dimer (center) and individual monomers (sides, peeled away and rotated relative to the two-symmetry axis) are shown. Coloring reflects sequence conservation among P/E/L viruses (see legend below) and was generated using the ConSurf server and the alignment in FIG. 21A and FIG. 21B. C peptides are shown as sticks and colored marine (monomer A) and light blue (monomer B). FIG. 9B, FIG. 9C, and FIG. 9D, zoomed views of conserved residue clusters that do not strictly contribute to the dimer interface.

FIG. 10A, Domain connectivity in TBSV capsid proteins. Unstructured linker that connects the C-terminus of the S domain (light blue) to the N-terminus of the P domain (dark blue) is highlighted in yellow. FIG. 10B, Arrangement of TBSV capsid proteins at the two-fold symmetry axis (dashed arrow) in the assembled virion shown in two orientations. S and P domains associated with individual monomers are colored orange and olive (monomer A) and slate and dark blue (monomer B). FIG. 10C, predicted connectivity in P/E/L virus capsid proteins based on structural modeling. Dashed yellow line denotes the predicted trajectory linking the C-terminus of the CP (light blue, from PLRV) to the N-terminus of the $^N$RTD (dark blue, from TuYV). FIG. 10D, composite model of the polerovirus RTP built from the crystallized TuYV $^N$RTD dimer and CP monomers taken from the cryo-EM reconstruction of the PLRV virus-like particle (VLP) (PDB: 6SCO). RTP dimer is organized around two-fold symmetry axis analogous to the arrangement in (FIG. 10B). FIG. 10E, View of subunit associations in (FIG. 10B) and (FIG. 10D) looking down the two-fold axis of symmetry in the direction of the dashed arrow in (FIG. 10B). FIG. 10F, Model illustrating the feasible positioning of $^N$RTD dimers (olive and dark blue) around icosahedral asymmetric unit of PLVR VLP assuming the structural organization in (FIG. 10D). Associated CP monomers are colored orange and slate with the reset of the capsid surface colored wheat.

FIG. 12A, FIG. 12B, FIG. 12C, and FIG. 12D provide graphical representation of data showing the PLRV $^N$RTD protein can be a used as tool to decrease PLRV transmission and kill *M. persicae*. FIG. 12A, The PLRV transmission efficiency of *M. persicae* is significantly different after feeding on various artificial diet treatments: no protein control (n=63), BSA (n=74), or purified PLRV $^N$RTD (SEQ ID NO: 2) (n=82). Experiment was repeated independently 5 times, with an average of 12 reps/treatment/experiment. FIG. 12B, *M. persicae* mortality after feeding on 0.1 mg/mL of BSA (n=232), the WT PLRV $^N$RTD (n=247), PLRV $^N$RTD with the point mutation SEQ ID NO: 4 (n=183), or no protein controls (n=244) for 48 hours and then moved to a PLRV-infected or uninfected detached hairy nightshade leaf. FIG. 12C, Same graph as in (FIG. 12B) with the following additional treatments: purified point mutants of the PLRV $^N$RTD SEQ ID NO: 5 (n=118), SEQ ID NO: 6

(n=264), SEQ ID NO: 7 (n=161) or one cluster mutant of the PLRV $^N$RTD (SEQ NO: 8; containing the three mutations N368A, C370A, Y411A, n=256). For FIG. 12A, FIG. 12B, and FIG. 12C, different letters represent significantly different treatments (P<0.05) by logistic regression analysis. Error bars represent #one standard error. FIG. 12D, Forest plot showing metanalysis of various trials of WT $^N$RTD feeding transmission assays using a random effects model. Graphed is the risk ratio (RR) of a plant becoming infected with PLRV after pre-exposure of aphids to the WT $^N$RTD as compared to the no protein control, grouped by whether the $^N$RTD was delivered via artificial diet or in planta. The vertical axis (x=1) represents the line of no effect. Values to the left of this line indicate a reduced chance of PLRV infection. Boxes represent the point estimate of effect size in each individual study. The size of the box corresponds to sample size (number of infected plants overall in that study). Horizontal lines represent the 95% confidence interval (95% CI) of the effect in each study. The center of the diamond represents the point estimate of the effect for each subgroup (red and blue) or all studies pooled (black), with the width of the diamond representing the 95% CI.

FIG. 13A, Experimental design for microinjection experiments. *M. persicae* aphids were microinjected using a microcapillary needle and compressed air with 1 μL of the PLRV $^N$RTD, BSA, or no protein controls. Aphids were immediately moved to PLRV-infected detached hairy nightshade leaves to acquire virus for a 24-hour acquisition access period (AAP). Next, aphids were moved to uninfected potato plants (cv. Red Maria) for a 72-hour an inoculation access period (IAP), 3-5 aphids/plant, 5-12 plants/treatment. After the IAP, aphids were killed by a pesticide application. After several weeks, the inoculated plants were tested for systemic PLRV infection via DAS-ELISA. FIG. 13B, The PLRV transmission efficiency of *M. persicae* is unaltered after microinjection with no protein control (n=19), or two concentrations each (0.1 mg/mL and 1 mg/mL) of BSA (n=40), or purified PLRV $^N$RTD (n=38). Experiment was repeated independently twice, with an average of 10 reps/treatment/experiment. Different letters represent significantly different treatments (P<0.05) by logistic regression analysis. Error bars represent ±one standard error.

FIG. 14A, FIG. 14B, FIG. 14C, FIG. 14D, FIG. 14E and FIG. 14F provide pictorial and graphic representation of in planta delivery methodology of the PLRV $^N$RTD to aphids and data collected therefrom. FIG. 14A, Construct design for in planta expression of the PLRV $^N$RTD. FIG. 14B and FIG. 14C, Western blot analysis of expression tests of YFP-$^N$RTD (FIG. 14B) and $^N$RTD-YFP (FIG. 14C) blotted with the anto-$^N$RTD antibody. FIG. 14D, Samples from the same expression tests in (FIG. 14B) and (FIG. 14C) blotted with an anti-GFP antibody. FIG. 14E, Experimental design for the in planta delivery experiments. *N. benthamiana* plants were infiltrated with transient expression constructs. At 2 days post inoculation (dpi) aphids fed on protein-expressing tissue for 48 hours. Then, *M. persicae* aphids were moved to PLRV-infected detached hairy nightshade leaves to acquire virus for a 24-hour acquisition access period (AAP). Next, aphids were moved to uninfected potato plants (cv. Red Maria) for a 72-hour an inoculation access period (IAP), 5 aphids/plant, 10-15 plants/treatment. After the IAP, aphids were killed by a pesticide application. After several weeks, the inoculated plants are tested for systemic PLRV infection via DAS-ELISA (n=37). FIG. 14F, PLRV transmission efficiency of *M. persicae* aphids after in planta delivery of the PLRV $^N$RTD. Different letters represent significantly different treatments (P<0.05) by logistic regression analysis. Error bars represent ±one standard error.

FIG. 19 provides pictorial and graphic representation of the experimental design and results for detecting virus titer in *M. persicae* aphids feeding on transgenic potatoes expressing PLRV $^N$RTD fused to YFP at the N-terminus.

FIG. 20 provides results of a dot blot analysis using an anti-PLRV $^N$RTD nanobody A7 (SEQ ID NO: 16).

DETAILED DESCRIPTION OF THE INVENTION

Figure 2E:
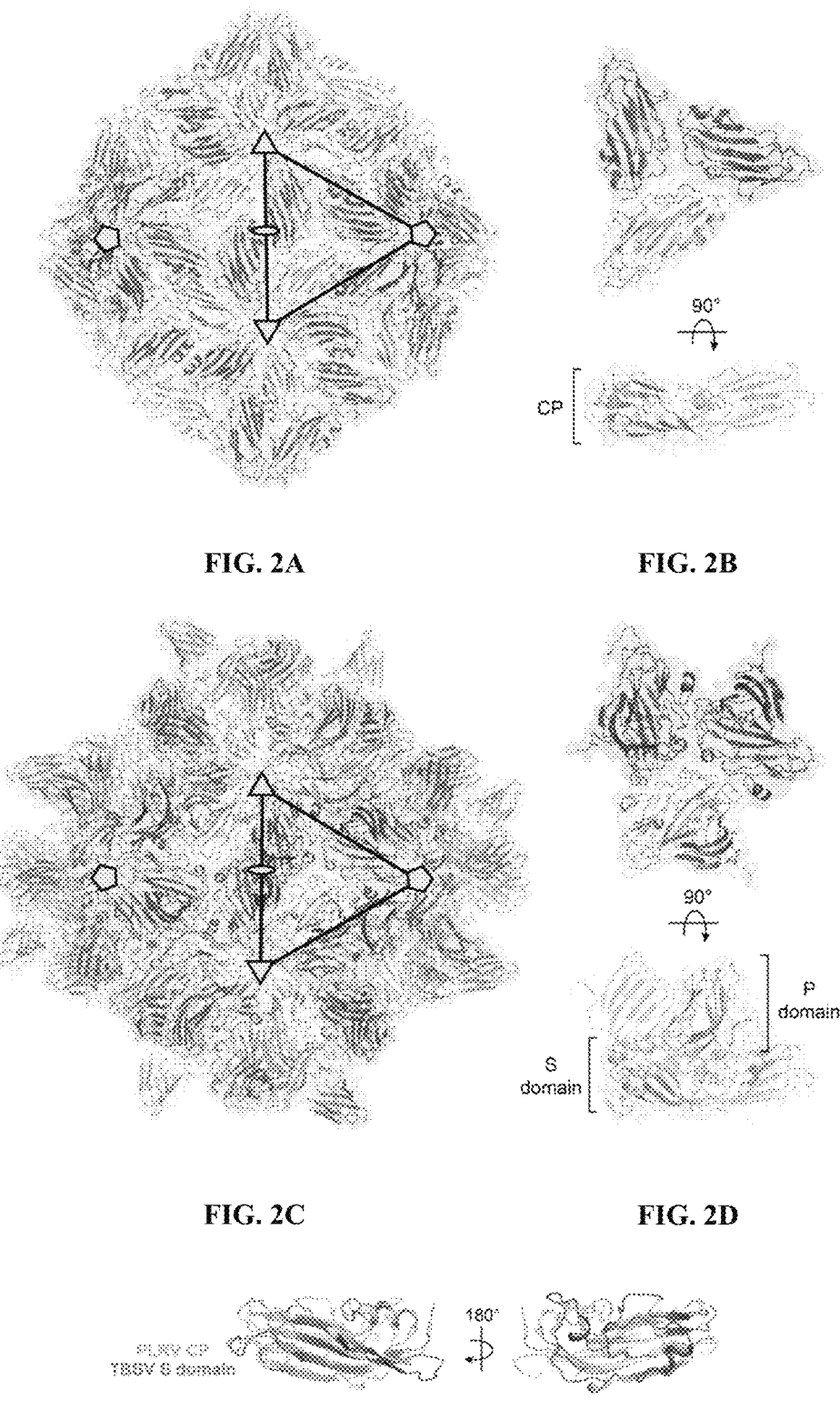

The present disclosure provides for the production and purification of proteins that block aphid acquisition and transmission of P/E/L viruses, including PLRV. This protein, termed $^N$RTD, is a two-domain protein encompassing a jelly roll domain, an interwoven cap domain, and an extended peptide segment immediately downstream of the jelly roll C-terminus (C peptide) that is structurally conserved and required for proper folding. In some embodiments, the monomeric forms of the protein form a dimer in solution.

$^N$RTD can, in some embodiments, be fused to a tag at the N-terminus or C-terminus. Exemplary tags include, but are not limited to, yellow fluorescent protein (YFP), green fluorescent protein (GFP), strep tag, FlAsH tag, or a polyhis-tidine tag (HIS tag).

These exemplary proteins of the invention were discovered by analyzing protein disorder, alignment to polerovirus genomes and atomic-resolution structural determination using X-ray crystallography. Prediction of secondary structure can also assist in developing P/E/L virus $^N$RTD proteins. Prior to the work presented herein, there were no structural models for P/E/L virus RTD proteins and there is a poor understanding of the aphid receptors and trafficking pathways that mediate viral uptake in the insect gut. These knowledge gaps have limited efforts to design targeted, small molecule inhibitors of transmission. The structural data presented herein and the constructs that are described in the disclosure provide new strategies to address both.

A fourth aspect of the invention provides a method of generation of $^N$RTD cap domain mutants that are lethal to aphids, where in the amino acid changes to generate the mutants can be determined by mapping the $^N$RTD sequence conservation onto the structure and/or identifying solvent accessible conserved residues that were not involved in interactions that structurally stabilized the protein folds and/or manual inspection of the $^N$RTD crystal structures for exposed residues in the cap domain.

The present disclosure further provides for the production of antibodies and nanobodies specific to P/E/L virus $^N$RTD with solubilized versions of the proteins. Antibodies can include monoclonal and polyclonal antibodies, as well as other antigen-binding biological proteins (e.g., heavy chain variable regions (VH), alpaca-derived antigen binding fragment of heavy-chain-only antibodies (VHH), and variable domain of new antigen receptors (VNAR)). These can be used for the production of anti-P/E/L virus $^N$RTD-specific immunological tools for virus detection and/or virus neutralization. Specifically provided herein are rabbit-derived polyclonal antibodies and alpaca-derived nanobodies that bind to PLRV $^N$RTD.

The present disclosure also provides for transgenic plants expressing P/E/L virus $^N$RTD, variants thereof (e.g., mutants and fusion proteins), or nanobodies that bind to $^N$RTD. Transgenic plants can be produced as stable transgenic plants, transiently transgenic or modified using symbiont technology.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N. Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

The term "antibody" refers to an immunoglobulin molecule produced by B lymphoid cells with a specific amino acid sequence. Antibodies are evoked in humans or other animals by a specific antigen (immunogen). Antibodies are characterized by reacting specifically with the target antigen in some demonstrable way, antibody and antigen each being defined in terms of the other. The term includes such variants as monoclonal antibodies, humanized antibodies, and other laboratory-created forms of natural antibodies.

The terms "coding sequence" and "coding region" as used herein refer to nucleotide sequences and nucleic acid sequences, including both RNA and DNA, that encode genetic information for the synthesis of an RNA, a protein, or any portion of an RNA or protein.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A◇T; G◇C; A◇U) and reading in the 5' to 3' direction, i.e., in opposite direction of the represented nucleotide sequence.

The term "control", and grammatical variants thereof, is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. This definition does not refer to internal controls for experiments.

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The term "PLRV RTP" and synonyms thereof refer to the PLRV wild-type readthrough protein having the sequence provided in SEQ ID NO:1. The amino acid at position 209 in SEQ ID NO: 1 is glutamine 90% of the time as indicated here but sometimes can be a tyrosine or a histidine.

The term "PLRV $^N$RTD" and synonyms thereof refer to the protein defined herein as SEQ ID NO: 2, a segment derived from the full-length PLRV RTP (SEQ ID NO: 1). The skilled artisan will understand that this disclosure contemplates all DNA and RNA species that encode these proteins, including codon-optimized sequences. The term can also refer to mutations of the proteins, or those with added components such as tags, as indicated by a relevant signifier. Specific examples of such modified sequences are provided as SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

The term "TuYV RTP" and synonyms thereof refer to the TuVY wild-type readthrough protein having the sequence provided in SEQ ID NO: 13.

The term "TuVY $^N$RTD" and synonyms thereof refer to the protein defined herein as SEQ ID NO: 14, a segment derived from the full-length TuYV RTP (SEQ ID NO: 13). The skilled artisan will understand that this disclosure contemplates all DNA and RNA species that encode these proteins, including codon-optimized sequences. This term also refers to mutations of the proteins, or those with added components such as tags, as indicated by a relevant signifier.

The term "CLRDV-RPV RTP" and synonyms thereof refer to the CLRDV-RPV wild-type readthrough protein having the sequence provided in SEQ ID NO: 18.

The term "CLRDV-RPV $^N$RTD" and synonyms thereof refer to the protein defined herein as SEQ ID NO: 19, a segment derived from the full-length CLRDV-RPV RTP (SEQ ID NO: 18). The skilled artisan will understand that this disclosure contemplates all DNA and RNA species that encode these proteins, including codon-optimized sequences. This term also refers to mutations of the proteins, or those with added components such as tags, as indicated by a relevant signifier.

The term "BYDV-PAV RTP" and synonyms thereof refer to the BYDV-PAV wild-type readthrough protein having the sequence provided in SEQ ID NO: 20.

The term "BYDV-PAV $^N$RTD" and synonyms thereof refer to the protein defined herein as SEQ ID NO: 21, a segment derived from the full-length CLRDV-RPV RTP (SEQ ID NO: 20). The skilled artisan will understand that this disclosure contemplates all DNA and RNA species that encode these proteins, including codon-optimized sequences. This term also refers to mutations of the proteins, or those with added components such as tags, as indicated by a relevant signifier.

The term "nucleic acid" as used herein, refers to a polymer of ribonucleotides or deoxyribonucleotides. Typically, "nucleic acid" polymers occur in either single- or double-stranded form but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs) and bridged nucleic acid (BNA, 2'-0,4'-aminoethylene bridged nucleic acid. See, e.g., Rahman, et al. (2007) *Nucleosides Nucleotides Nucleic Acids* 26:1625-1628). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein. For nucleic acids, sizes are given in either kilobases (kb) or base pairs (bp), or nucleotides (nt). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences. Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). Because of the degeneracy of nucleic acid codons, one can use various different polynucleotides to encode identical polypeptides. The table below contains information about which nucleic acid codons encode which amino acids.

| Amino acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |

-continued

| Amino acid | Nucleic acid codons |
|---|---|
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like).

A "conservative substitution" in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The phrase "high percent identity", and grammatical variations thereof in the context of two polynucleotides or polypeptides, refers to two or more sequences or subsequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

$^{N}$RTD Sequences

Figure 21A:
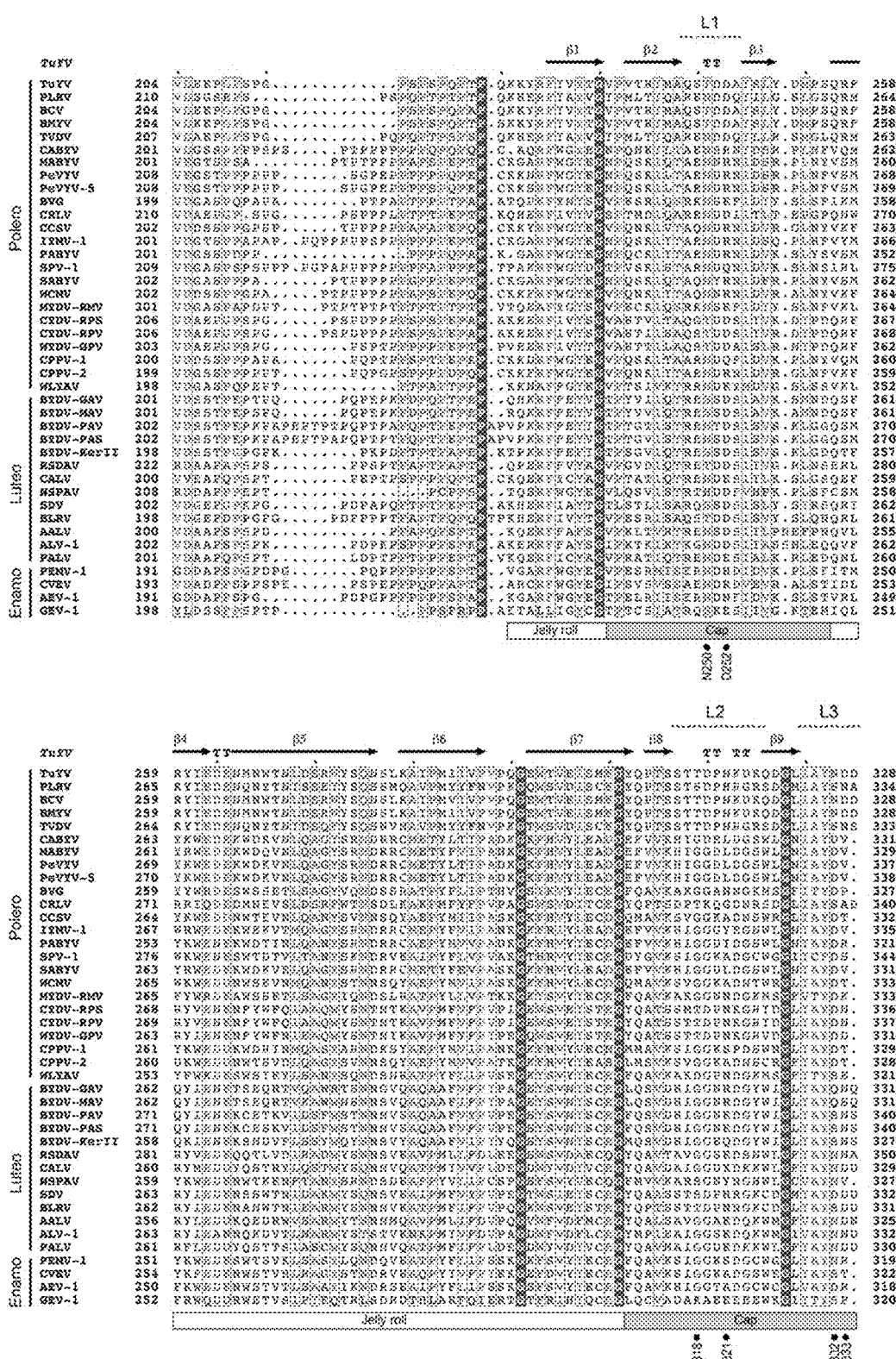
FIG. 21A and FIG. 21B provide a protein sequence alignment of P/E/L virus $^N$RTDs. Sequence alignment of P/E/L virus $^N$RTD regions with the secondary structure of the TuYV $^N$RTD mapped above. Sequences are organized by genera to distinguish between poleroviruses (polero), luteoviruses (luteo), and enamoviruses (enamo). Segments within the jelly roll domain, cap domain, and C peptide, respectively, are labeled beneath. Cap domain loops (L1-5) and C peptide are labeled above. Black circles below the alignment designate positions of PLRV mutations tested in this study. Sequence shading indicates conservation: white text on red background, 100% conserved; boxed red text on white background, 70% conserved. For PLRV $^N$RTD, position 210 in FIG. 21A and position 335 in FIG. 21B correspond to positions 210 and 335 in SEQ ID NO: 1, respectively. For TuYV $^N$RTD, position 204 in FIG. 21A and position 329 in FIG. 21B correspond to positions 204 and 329 in SEQ ID NO: 13, respectively. Abbreviations in sequence alignment are as follows with accompanying KEGG database IDs: TuYV, Turnip yellows virus (vg: 940480) SEQ ID NO: 13; PLRV, Potato leafroll virus (vg: 1493889) SEQ ID NO: 1; BCV, Beet chlorosis virus (vg: 921081) SEQ ID NO: 22; BMYV, Beet mild yellowing virus (vg: 935287) SEQ ID NO: 23; TVDV, Tobacco vein distorting virus (vg: 6325587) SEQ ID NO: 24; CABYV, Cucurbit aphid-borne yellows virus (vg: 940449) SEQ ID NO: 25; MABYV, Melon aphid-borne yellows virus (vg: 6369694) SEQ ID NO: 26; PeVYV, Pepper vein yellows virus (vg: 10192273) SEQ ID NO: 27; PeVYV-5, Pepper vein yellows virus 5 (vg: 35659779) SEQ ID NO: 28; BVG, Barley virus G (vg: 27246436) SEQ ID NO: 29; CRLV, Carrot red leaf virus (vg: 3021801) SEQ ID NO: 30; CCSV, Chickpea chlorotic stunt virus (vg: 4187204) SEQ ID NO: 31; IYMV-1, Ixeridium yellow mottle virus 1 (vg: 27111910) SEQ ID NO: 32; PABYV, Pepo aphid-borne yellows virus (vg: 27924363) SEQ ID NO: 33; SPV-1, Strawberry polerovirus/(vg: 22276102) SEQ ID NO: 34; SABYV, Suakwa aphid-borne yellows virus (vg: 13564455) SEQ ID NO: 35; WCMV, White clover mottle virus (vg: 30090157) SEQ ID NO: 36; MYDV-RMV, Maize yellow dwarf virus RMV (vg: 16215725) SEQ ID NO: 37; CYDV-RPS, Cereal yellow dwarf virus RPS (vg: 1489893) SEQ ID NO: 38; CYDV-RPV, Cereal yellow dwarf virus RPV (vg: 1478313) SEQ ID NO: 18; WYDV-GPV, Wheat yellow dwarf virus-GPV (vg: 10220411) SEQ ID NO: 39; CPPV-1, Cowpea polerovirus 1 (vg: 31653049) SEQ ID NO: 40; CPPV-2, Cowpea polero-virus 2 (vg: 31653057) SEQ ID NO: 41; WLYAV, Wheat leaf yellowing-associated virus (vg: 33867841) SEQ ID NO: 42; BYDV-GAV, Barley yellow dwarf virus GAV (vg: 1485846) SEQ ID NO: 43; BYDV-MAV, Barley yellow dwarf virus MAV (vg: 940436) SEQ ID NO: 44; BYDV-PAV, Barley yellow dwarf virus PAV (vg: 1492000) SEQ ID NO: 45; BYDV-PAS, Barley yellow dwarf virus PAS (vg: 1489885) SEQ ID NO: 46; BYDV-KerII, Barley yellow dwarf virus KerlI (vg: 15842601) SEQ ID NO: 47; RSDAV, Rose spring dwarf-associated virus (vg: 6369703) SEQ ID NO: 48; CALV, Cherry associated luteovirus (vg: 30204393) SEQ ID NO: 49; NSPAV, Nectarine stem pitting-associated virus (vg: 24528016) SEQ ID NO: 50; SDV, Soybean dwarf virus (vg: 921703) SEQ ID NO: 51; BLRV, Bean leafroll virus (vg: 932046) SEQ ID NO: 52; AALV, Apple-associated luteovirus (vg: 41701548) SEQ ID NO: 53; ALV-1, Apple luteovirus 1 (vg: 41702098) SEQ ID NO: 54; PALV, Peach associated luteovirus (vg: 33133630) SEQ ID NO: 55; PEMV-1, Pea enation mosaic virus 1 (vg: 940255) SEQ ID NO: 56; CVEV, Citrus vein enation virus (vg: 15957166) SEQ ID NO: 57; AEV-1, Alfalfa enamovirus 1 (vg: 27429657) SEQ ID NO: 58; GEV-1, Grapevine enamovi-rus-1 (vg: 32965585) SEQ ID NO: 59.
Figure 21B:
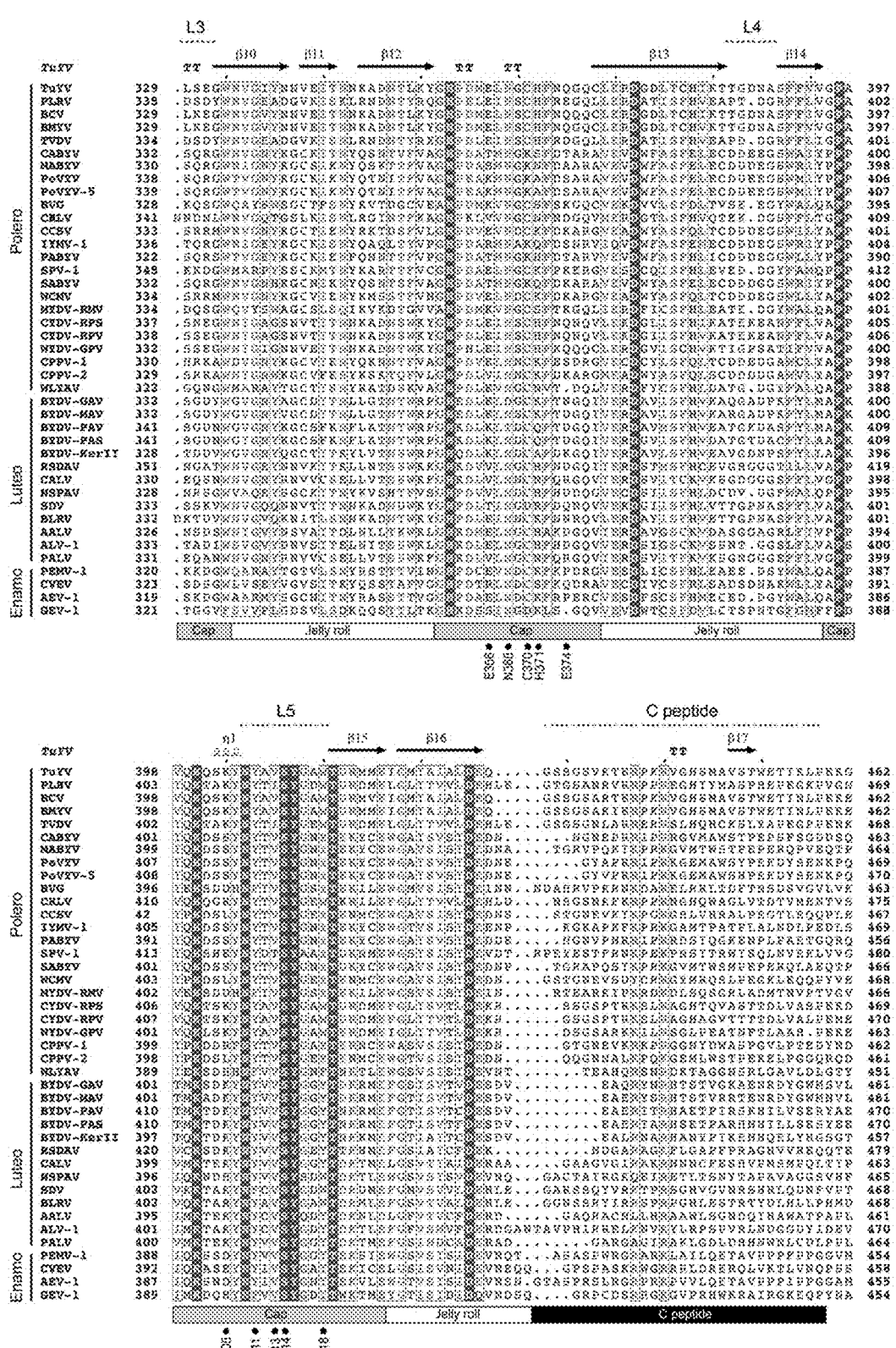

Sequence alignment of P/E/L virus $^{N}$RTD regions with the secondary structure of the TuYV $^{N}$RTD mapped above can be found in FIG. 21A and FIG. 21B. Sequences are organized by genera to distinguish between poleroviruses (polero), luteoviruses (luteo), and enamoviruses (enamo). Segments within the jelly roll domain, cap domain, and C peptide, respectively, are labeled below the alignment (see FIG. 4A and FIG. 4B). These $^{N}$RTD sequences of different poleroviruses, luteoviruses and enamoviruses are highly similar to each other. For example, the region between amino acids 204-462 of the TuYV RTP (SEQ ID NO: 13) and 201-469 of the PLRV RTP (SEQ ID NO: 1) share a high percent identity and overall conservation of predicted secondary structural elements. These structural elements include 17 beta sheets, 5 loops, which are intercalated between the beta sheets, and a C-peptide, which encompasses the C-terminal end of the $^{N}$RTD and found in all available sequences of P/E/L virus $^{N}$RTD available in public sequence repositories. While not predicted by the primary amino acid sequence, the structure of the $^{N}$RTD reveals regions of the cap domain that are either more variable among P/E/L viruses or more highly conserved. These positions on the cap domain and their conservation in the family guided the selection of certain residues for mutagenesis, in some embodiments H92 in SEQ ID NO: 2, corresponding to H321 in SEQ ID NO: 1, as being a variable amino acid or S185 in SEQ ID NO: 2, corresponding to S414 in SEQ ID NO: 1, as being absolutely conserved among all P/E/L virus species. Cap domain loops (L1-5) and C peptide are labeled above. Black circles below the alignment designate positions of PLRV mutations (see FIG. 9B, FIG. 9C, FIG. 9D, FIG. 12B, FIG. 12C, and FIG. 12D) with numbering relating to the position in SEQ ID NO:1. Sequence shading in alignment indicates conservation: white text on red background, 100% conserved; boxed red text on white background, 70% conserved. Abbreviations in sequence alignment are as follows with accompanying KEGG database IDs: TuYV, Turnip yellows virus (vg: 940480) SEQ ID NO: 13; PLRV, Potato leafroll virus (vg: 1493889) SEQ ID NO: 1; BCV, Beet chlorosis virus (vg: 921081) SEQ ID NO: 22; BMYV, Beet mild yellowing virus (vg: 935287) SEQ ID NO: 23; TVDV, Tobacco vein distorting virus (vg: 6325587) SEQ ID NO: 24; CABYV, Cucurbit aphid-borne yellows virus (vg: 940449) SEQ ID NO: 25; MABYV, Melon aphid-borne yellows virus (vg: 6369694) SEQ ID NO: 26; PeVYV, Pepper vein yellow's virus (vg: 10192273) SEQ ID NO: 27; PeVYV-5, Pepper vein yellows virus 5 (vg: 35659779) SEQ ID NO: 28; BVG, Barley virus G (vg: 27246436) SEQ ID NO: 29; CRLV, Carrot red leaf virus (vg: 3021801) SEQ ID NO: 30; CCSV, Chickpea chlorotic stunt virus (vg: 4187204) SEQ ID NO: 31; IYMV-1, Ixeridium yellow mottle virus/(vg: 27111910) SEQ ID NO: 32; PABYV, Pepo aphid-borne yellows virus (vg: 27924363) SEQ ID NO: 33; SPV-1, Strawberry polerovirus 1 (vg: 22276102) SEQ ID NO: 34; SABYV, Suakwa aphid-borne yellows virus (vg: 13564455) SEQ ID NO: 35; WCMV, White clover mottle virus (vg: 30090157) SEQ ID NO: 36; MYDV-RMV, Maize yellow dwarf virus RMV (vg: 16215725) SEQ ID NO: 37; CYDV-RPS, Cereal yellow dwarf virus RPS (vg: 1489893) SEQ ID NO: 38; CYDV-RPV, Cereal yellow dwarf virus RPV (vg: 1478313) SEQ ID NO: 18; WYDV-GPV, Wheat yellow dwarf virus-GPV (vg: 10220411) SEQ ID NO: 39; CPPV-1, Cowpea polerovirus 1 (vg: 31653049) SEQ ID NO: 40; CPPV-2, Cowpea polerovirus 2 (vg: 31653057) SEQ ID NO: 41; WLYAV, Wheat leaf yellowing-associated virus (vg: 33867841) SEQ ID NO: 42; BYDV-GAV, Barley yellow dwarf virus GAV (vg: 1485846) SEQ ID NO: 43; BYDV-MAV, Barley yellow dwarf virus MAV (vg: 940436) SEQ ID NO: 44; BYDV-PAV, Barley yellow dwarf virus PAV (vg: 1492000) SEQ ID NO: 45; BYDV-PAS, Barley yellow dwarf virus PAS (vg: 1489885) SEQ ID NO: 46; BYDV-KerII, Barley yellow dwarf virus KerII (vg: 15842601) SEQ ID NO: 47; RSDAV, Rose spring dwarf-associated virus (vg: 6369703) SEQ ID NO: 48; CALV, Cherry associated luteovirus (vg: 30204393) SEQ ID NO: 49; NSPAV, Nectarine stem pitting-associated virus (vg: 24528016) SEQ ID NO: 50; SDV, Soybean dwarf virus (vg: 921703) SEQ ID NO: 51; BLRV, Bean leafroll virus (vg: 932046) SEQ ID NO: 52; AALV, Apple-associated luteovirus (vg: 41701548) SEQ ID NO: 53; ALV-1, Apple luteovirus 1 (vg: 41702098) SEQ ID NO: 54; PALV, Peach associated luteovirus (vg: 33133630) SEQ ID NO: 55; PEMV-1, Pea enation mosaic virus 1 (vg: 940255) SEQ ID NO: 56; CVEV, Citrus vein enation virus (vg: 15957166) SEQ ID NO: 57; AEV-1, Alfalfa enamovirus 1 (vg: 27429657) SEQ ID NO: 58; GEV-1, Grapevine enamovirus-1 (vg: 32965585) SEQ ID NO: 59.

Specific, non-limiting examples of $^{N}$RTD sequences, including wild-type, other truncated and mutant sequences provided herein include SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term "recombinant nucleic acids" refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

In practicing some embodiments of the disclosure disclosed herein, it can be useful to modify the genomic DNA, chloroplast DNA or mitochondrial DNA of a recombinant strain of a host cell to produce a P/E/L virus $^N$RTD protein, or mutant thereof to introduce genetic elements allowing for the expression of introduced genes (e.g., promoters and other regulatory elements). In some embodiments, such a host cell is a plant cell.

Modifications intended to alter function of a target protein can involve mutations of the DNA or gene encoding the target protein, including deletion of all or a portion of a target gene, including but not limited to the open reading frame of a target locus. Such deletional mutations can be achieved using any technique known to those of skill in the art. Mutational, insertional, and deletional variants of disclosed nucleotide sequences and genes can be readily prepared by methods which are well known to those skilled in the art. It is well within the skill of a person trained in this art to make mutational, insertional, and deletional mutations which are equivalent in function to the specific ones disclosed herein.

Where a recombinant nucleic acid is intended for expression, cloning, or replication of a particular sequence, DNA constructs prepared for introduction into a host cell will typically comprise a replication system (i.e. vector) recognized by the host, including the intended DNA fragment encoding a desired polypeptide, and can also include transcription and translational initiation regulatory sequences operably linked to the polypeptide-encoding segment. Additionally, such constructs can include cellular localization signals (e.g., chloroplast localization signals). In preferred embodiments, such DNA constructs are introduced into a host cell's genomic DNA, chloroplast DNA or mitochondrial DNA.

In some embodiments, a non-integrated expression system can be used to induce expression of one or more introduced genes. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the disclosure disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present disclosure. One of skill in the art will recognize that any relevant markers available can be utilized in practicing the inventions disclosed herein.

Screening and molecular analysis of recombinant organisms (e.g., transgenic plants or recombinant bacteria) of the present disclosure can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject disclosure. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) *Current Protocols in Molecular Biology*, John Wiley & Sons, NY, N. Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Because the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present disclosure can also encompass homologues of the specifically disclosed sequences. Homology (e.g., sequence identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, word-length=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Recombinant host cells (such as transgenic plant cells or recombinant microbial cells), in the present context, are those which have been genetically modified to contain an isolated nucleic molecule, and/or contain one or more genes to produce at least one recombinant protein. The nucleic acid(s) encoding the protein(s) of the present disclosure can be introduced by any means known to the art which is appropriate for the particular type of cell, including without limitation, transformation, lipofection, electroporation or any other methodology known by those skilled in the art.

Transgenic Plants and Plant Cells

One embodiment of the present disclosure provides a plant or plant cell comprising one or more modified plant genes and/or introduced genes. For example, the present disclosure provides transgenic plants that express PLRV $^N$RTD, mutants and other modified versions thereof, including those toxic to aphids and those which decrease luteovirus transmission.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium Protocols*, ed: Gartland, Humana Press Inc. (1995); and Wang, et al. *Acta Hort.* 461:401-408 (1998). The choice of method varies with the type of plant to be transformed, the particular application and/or the desired result. The appropriate transformation technique is readily chosen by the skilled practitioner.

Any methodology known in the art to delete, insert or otherwise modify the cellular DNA (e.g., genomic DNA and organelle DNA) can be used in practicing the inventions disclosed herein. For example, a disarmed Ti-plasmid, containing a genetic construct for deletion or insertion of a target gene, in *Agrobacterium tumefaciens* can be used to transform a plant cell, and thereafter, a transformed plant can be regenerated from the transformed plant cell using procedures described in the art, for example, in EP 0116718, EP 0270822, PCT publication WO 84/02913 and published European Patent application ("EP") 0242246. Ti-plasmid vectors each contain the gene between the border sequences, or at least located to the left of the right border sequence, or the T-DNA of the Ti-plasmid. Of course, other types of vectors can be used to transform the plant cell, using procedures such as symbiont technology (WO 21/055656), direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536, 475), and other methods such as the methods for transforming certain lines of corn (e.g., U.S. Pat. No. 6,140,553; Fromm et al., Bio/Technology (1990) 8, 833-839); Gordon-Kamm et al., The Plant Cell, (1990) 2, 603-618) and rice (Shimamoto et al., Nature, (1989) 338, 274-276; Datta et al., Bio/Technology, (1990) 8, 736-740) and the method for transforming monocots generally (PCT publication WO 92/09696). For cotton transformation, the method described in PCT patent publication WO 00/71733 can be used.

Transgenic plants of the present disclosure can be used in a conventional plant breeding scheme to produce more transgenic plants with the same characteristics, or to introduce the genetic alteration(s) in other varieties of the same or related plant species. Seeds, which are obtained from the transformed plants, can contain the genetic alteration(s) as a stable insert in chromosomal or organelle DNA. Plants comprising the genetic alteration(s) in accordance with the disclosure include plants comprising, or derived from, root stocks of plants comprising the genetic alteration(s) of the disclosure, e.g., fruit trees or ornamental plants. Hence, any non-transgenic grafted plant parts inserted on a transformed plant or plant part are included in the disclosure.

Introduced genetic elements, whether in an expression vector or expression cassette, which result in the expression of an introduced gene will typically utilize a plant-expressible promoter. A 'plant-expressible promoter' as used herein refers to a promoter that ensures expression of the genetic alteration(s) of the disclosure in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871-2887), CabbB-S (Franck et al., Cell (1980) 21, 285-294) and CabbB-JI (Hull and Howell, Virology, (1987) 86, 482-493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., EMBO J, (1984) 3, 2723-2730).

Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., Plant J, (1997) 12:293-304) has been described to be a strong promoter for expression in vascular tissue and is useful in one embodiment of the current disclosure. Alternatively, a plant-expressible promoter can also be a wound-inducible promoter, such as the promoter of the pea cell wall invertase gene (Zhang et al., Plant Physiol, (1996) 112:1111-1117). A 'wound-inducible' promoter as used herein means that upon wounding of the plant, either mechanically or by insect feeding, expression of the coding sequence under control of the promoter is significantly increased in such plant. These plant-expressible promoters can be combined with enhancer elements, they can be combined with minimal promoter elements, or can comprise repeated elements to ensure the expression profile desired.

In some embodiments, genetic elements can be used to increase expression in plant cells can be utilized. For example, an intron at the 5' end or 3' end of an introduced gene, or in the coding sequence of the introduced gene, e.g., the hsp70 intron. Other such genetic elements can include, but are not limited to, promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

An introduced gene of the present disclosure can be inserted in host cell DNA so that the inserted gene part is upstream (i.e., 5') of suitable 3' end transcription regulation signals (i.e., transcript formation and polyadenylation signals). This is preferably accomplished by inserting the gene in the plant cell genome (nuclear or chloroplast). Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835-845), the SCSV or the Malic enzyme terminators (Schunmann et al., Plant Funct Biol, (2003) 30:453-460), and the T-DNA gene 7 (Velten and Schell, Nucleic Acids Res, (1985) 13, 6981-6998), which act as 3'-untranslated DNA sequences in transformed plant cells.

Antibodies and Immunoassays

One skilled in the art will recognize that any classical or alternative methods can be used to prepare the antibodies and nanobodies of the invention. For monoclonal and polyclonal antibody production, the immunogen (i.e., antigen) of interest is typically administered (e.g. intraperitoneal injection) to wild-type mice or transgenic mice, rats, rabbits, or other animal species which can produce native, humanized, or other desired antibodies and variants thereof (nanobodies). The immunogen can be administered alone or as a fusion protein to induce an immune response with adjuvants known to one of skill in the art including.

The antibodies and nanobodies disclosed herein (and other versions such as monoclonal antibodies) can be utilized in any immunoassay system known in the art including, but not limited to: radioimmunoassays, enzyme-linked immunosorbent assay (ELISA), "sandwich" assays, precipitin reactions, gel diffusion immunodiffusion assays, agglutination assays, fluorescent immunoassays, protein A immunoassays, immunohistochemistry assays, and immunoelectrophoresis. Such assays can be used to detect the presence and/or amounts a target luteovirus $^{N}$RTD in a biological or environmental sample. Antibodies and nanobodies of the present disclosure can be bound to a solid support in which the immunoassay is to be performed. The solid support can be glass or a polymer, including, but not limited to cellulose, polyacrylamide, nylon, polystyrene, polyvinylchloride or polypropylene. The solid supports can be in the form of tubes, beads, discs microplates, or any other surfaces suitable for conducting an immunoassay.

Antibodies, nanobodies, or fragments thereof, can be labeled using any of a variety of labels and methods of labeling known to those of skill in the art. Examples of types of labels which can be used in the present invention include, but are not limited to, enzyme labels, radioisotopic labels, non-radioactive isotopic labels, chromogenic labels, fluorescent labels, and chemiluminescent labels (see e.g., Harlow and Lane, Antibodies: A Laboratory Manual [Cold Spring Harbor Laboratory, New York 1988] 555-612).

Lateral Flow Immunoassays and Devices

The present disclosure contemplates the inclusion of anti-P/E/L virus-$^{N}$RTD antibodies and nanobodies into lateral flow chromatography assay devices to allow detection of P/E/L virus in a sample. Generally, such devices have an extended base layer on which a differentiation can be made between a sample application region and an evaluation region. Typically, the sample (or portion thereof) to be tested is applied to an application region, flows along a liquid transport path (e.g., nitrocellulose or wicking paper), and into an immunocomplex-formation region. A capture reagent is present in the immunocomplex-formation region which captures the antigen to be detected (if present in the sample) and the captured antigen can be detected. For example, the assay may produce a visual signal, such as color change, fluorescence, luminescence, and the like, when indicating the presence or absence of an analyte in a biological sample. In some instances, where the device is electronic, the formation of the antigen-antibody complex creates a signal which is transformed to a visual signal, such as on a display screen.

Such devices preferably provide a clear signal indicating to a user when the antigen of interest (e.g., an amanitin) is present in the tested sample and a different signal when the antigen is absent. Non-limiting examples include a plus signal when the antigen is present and a minus signal when absent, two bands when absent and one band when present, two bands when present and one band when absent, and the like. Devices of this kind are well known in the art (e.g., pregnancy tests, ovulation tests, urine tests, spinal fluid tests, blood tests, etc.). They are used by skilled technicians and lay person alike. Thus, there is a strong impetus to provide devices that are simple and reliable. Desirably, the assays are single-step devices wherein the user need only apply the sample prior to viewing the result.

Having generally described this invention, the same will be better understood by reference to certain specific examples, which are included herein to further illustrate the invention and are not intended to limit the scope of the invention as defined by the claims.

EXAMPLES

Example 1

Structural Organization of Polerovirus Proteins $^{N}$RTD from different P/E/L virus species form dimers in solution. To understand the molecular interactions governing polerovirus acquisition and aphid transmission, we generated soluble versions of the $^{N}$RTD regions from PLRV (SEQ ID NO: 2) and TuYV (SEQ ID NO: 14) that could be expressed in *E. coli* and purified on the milligram scale for structural and biochemical studies. (FIG. 1A, FIG. 1B and FIG. 1C). Size exclusion chromatography coupled to multi-angle light scattering (SEC-MALS) shows that these constructs form stable dimers in solution (FIG. 1D). Both readily crystallized and we solved the structure of the PLRV $^N$RTD at 2.22 Å by single wavelength anomalous diffraction (SAD) phasing using selenomethionine-labeled protein (FIG. 3A, FIG. 3B, and Table 1). The TuYV $^N$RTD structure was subsequently solved by molecular replacement yielding a more complete model that was refined to 1.53-Å resolution (FIG. 4A, FIG. 4B, and Table 1-Values in parentheses in Table 1 are for highest-resolution shell. Each structure was determined from a single crystal).

TABLE 1

| | | |
|---|---|---|
| Data collection and refinement statistics. | | |
| | PLRV $^N$RTD | TuYV $^N$RTD |
| Data collection | | |
| Space group | P2₁22₁ | P2₁2₁2₁ |
| Cell dimensions | | |
| a, b, c (Å) | 63.23, 65.15, 109.68 | 46.46, 74.86, 130.78 |
| α, β, γ (°) | 90, 90, 90 | 90, 90, 90 |
| Resolution (Å) | 56.01-2.22 (2.29-2.22) | 64.97-1.53 (1.55-1.53) |
| $R_{merge}$ | 0.01 (0.85) | 0.07 (0.73) |
| I/σI | 10.5 (0.8) | 20.5 (2.2) |
| Completeness (%) | 96.8 (75.2) | 99.5 (93.1) |
| Redundancy | 5.1 (2.0) | 6.7 (6.3) |
| Refinement | | |
| Resolution (Å) | 2.22 | 1.53 |
| No. reflections | 22,407 | 69703 |
| $R_{work}/R_{free}$ | 20.1/24.6 | 17.4/19.6 |
| No. atoms | | |
| Protein | 3437 | 3822 |
| Ligand/ion | 5 | 0 |
| Water | 16 | 587 |
| B-factors | | |
| Protein | 57.6 | 23.6 |
| Ligand/ion | 54.1 | — |
| Water | 45.7 | 33.6 |
| R.m.s deviations | | |
| Bond lengths (Å) | 0.01 | 0.01 |
| Bond angles (°) | 1.3 | 1.3 |

Figures 5A, 5B, 5C:
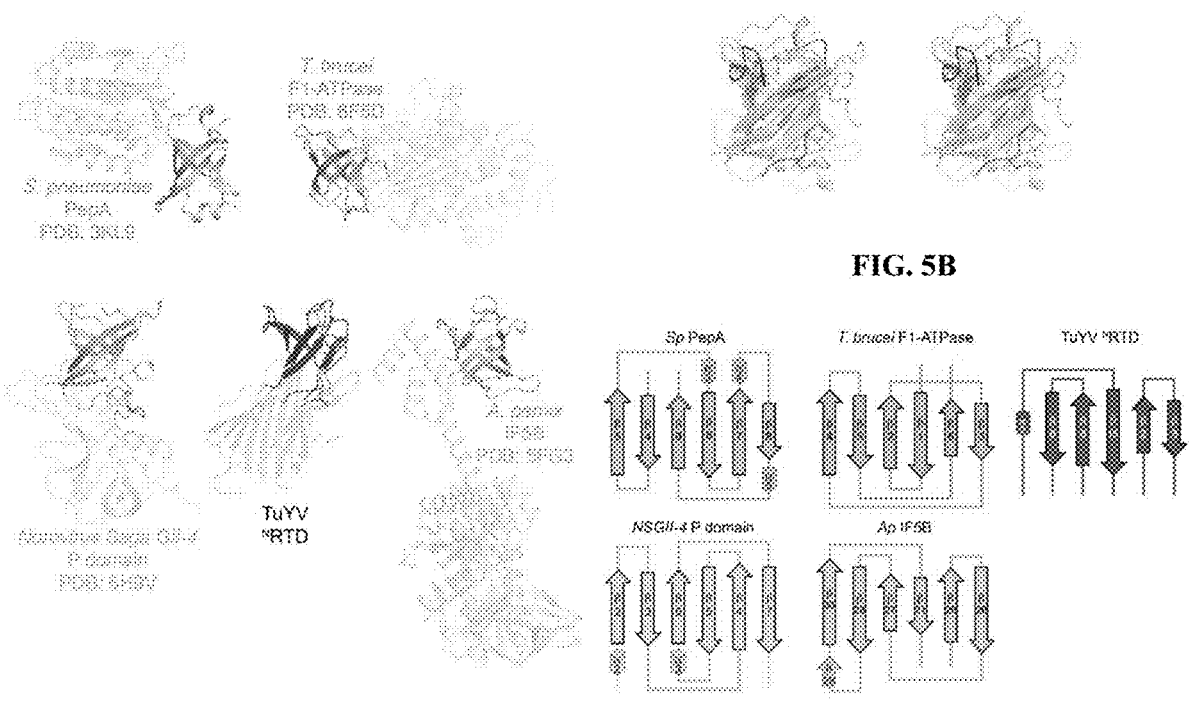
FIG. 5A, FIG. 5B, and FIG. 5C provide pictorial representation of the cap domain β-barrel adopting a conserved fold with unique topology.

The $^N$RTD is a two-domain protein. Each TuYV $^N$RTD monomer contains a total of 16 β-strands that are divided among two structural domains. Eleven of these strands form two anti-parallel β-sheets—ordered β12-13-7-16-1-4-5 (sheet 1) and β5-6-14-10 (sheet 2)—that sandwich together to adopt a jellyroll fold (FIG. 4A, FIG. 4B, orange). β5 adopts a twisted conformation that runs orthogonal to the plane of the sandwich and connects the two sheets along one edge (FIG. 4A, FIG. 4B). The short β11 strand connects the sheets on the opposite edge. The additional five strands form an anti-parallel β-sheet (β9-8-15-2-3) that curves into a small barrel with a short a helix (α1) flanking the edge of β3 (FIG. 4A, FIG. 4B, purple). A series of well resolved loops (L1-L5) connect these segments, with L4 folding over and acting as a lid. We designate this barrel the 'cap domain', as it sits above the jellyroll base. The DALI alignment algorithm indicates that the cap domain fold is present in a number of unrelated proteins, including the dimerization domains of aminopeptidases, the N-terminal region of the F1-ATPase rotary subunits, the *Aeropyrum pernix* IF5B initiation factor, and mammalian Norovirus spike proteins (FIG. 5A, FIG. 5B). The topology differs in TuYV, however, as the individual secondary structure elements are distributed throughout the jellyroll rather than being clustered sequentially as a single globular unit (FIG. 4B, FIG. 5A, FIG. 5B, FIG. 5C). PLRV $^N$RTD monomers adopt the same specific domain arrangement and topology (FIG. 3A, FIG. 3B), suggesting this organization is an important feature unique to P/E/L viruses.

The jelly roll domains of P/E/L viruses $^N$RTDs are structurally related to domains in other plant viruses. DALI also reveals that PLRV and TuYV $^N$RTDs share structural homology with the P domains of some viruses in the Tombusviridae family, with the nearest structural homologs being Tomato bushy stunt virus (TBSV; PDB: 2TBV), Melon necrotic spot virus (PDB: 2ZAH), and Cucumber necrosis virus (PDB: 4LLF). Tombusviruses share many biological properties with P/E/L viruses—including a small, positive-sense single-stranded RNA genome, a non-enveloped icosahedral capsid with T=3 symmetry comprised of 180 copies of the CP (FIG. 2A, FIG. 2B, FIG. 2C, FIG. 2D), and similar host range of infection, but are distinct in that they not aphid transmissible and lack an analogous readthrough domain. Instead, the viral CP contains two domains (S and P) that are constitutively expressed as a single polypeptide, with the S domain forming the icosahedral capsid shell and the P domain extending from each monomer via flexible linker at all points of two-fold rotational symmetry within the assembled virion (FIG. 2C, FIG. 2D). While previous cryo-EM studies demonstrated structural homology between polerovirus CPs and tombusvirid S domains (FIG. 2E), structural superposition here shows that the TBSV P domain aligns with the jelly roll domain of each P/E/L virus $^N$RTD but lacks the corresponding inserts that make up the cap domain (FIG. 3B, FIG. 3C, FIG. 4B, FIG. 4C and FIG. 4D). The conserved topologies between both families (FIG. 3B, FIG. 4B and FIG. 4D) and the intricate distribution of cap domain segments throughout the primary sequence (FIG. 21A, FIG. 21B) suggest that poleroviruses may be ancestral to tombusvirids, with tombusvirids likely evolving via the gradual loss of cap domain elements and truncation of loops L1-L5 rather than through the concerted acquisition of these segments in a manner that would be constrained by the proper folding of both domains.

A peptide at the C-terminus of the $^N$RTD allows for stabilization of the $^N$RTD dimer. We also observe a largely unstructured peptide (the 'C peptide') extending from β16 in the TuYV $^N$RTD, which transverses sheet 1 and terminates in a final strand (β17) that packs against β12 in an antiparallel orientation (FIG. 4A, FIG. 4B, marine). From the electron density, we can define the sequence of this segment unambiguously as the C-terminal portion of the construct (residues 431-459) (FIG. 6A). A disconnected fragment of the C peptide (residues 442-445) is resolved in the PLRV structure (FIG. 6B), likely owing to partial proteolytic cleavage and dissociation of the liberated fragment during purification and/or crystallization.

Figures 7A, 7B, 7C, 7D, 7E:
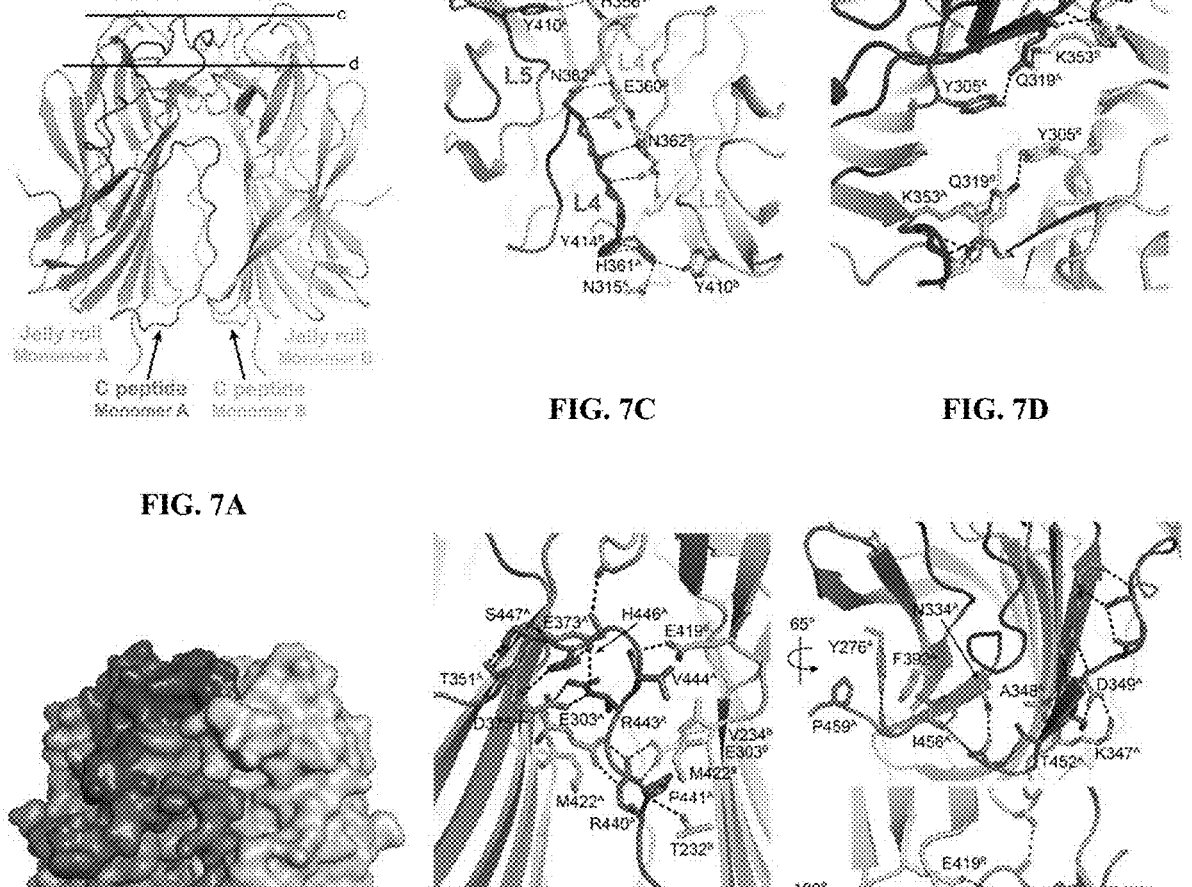
FIG. 7A, FIG. 7B, FIG. 7C, FIG. 7D, and FIG. 7E provide pictorial representation of the architecture of the TuYV $^N$RTD dimer. Cartoon (FIG. 7A) and surface (FIG. 7B) representations of the TuYV $^N$RTD dimer. Individual structural segments are labeled in each monomer and colored as follows: Jelly roll domains, orange and light orange; cap domains, purple and light pink; C peptides, marine and light blue.
Figures 8A, 8C, 8D:
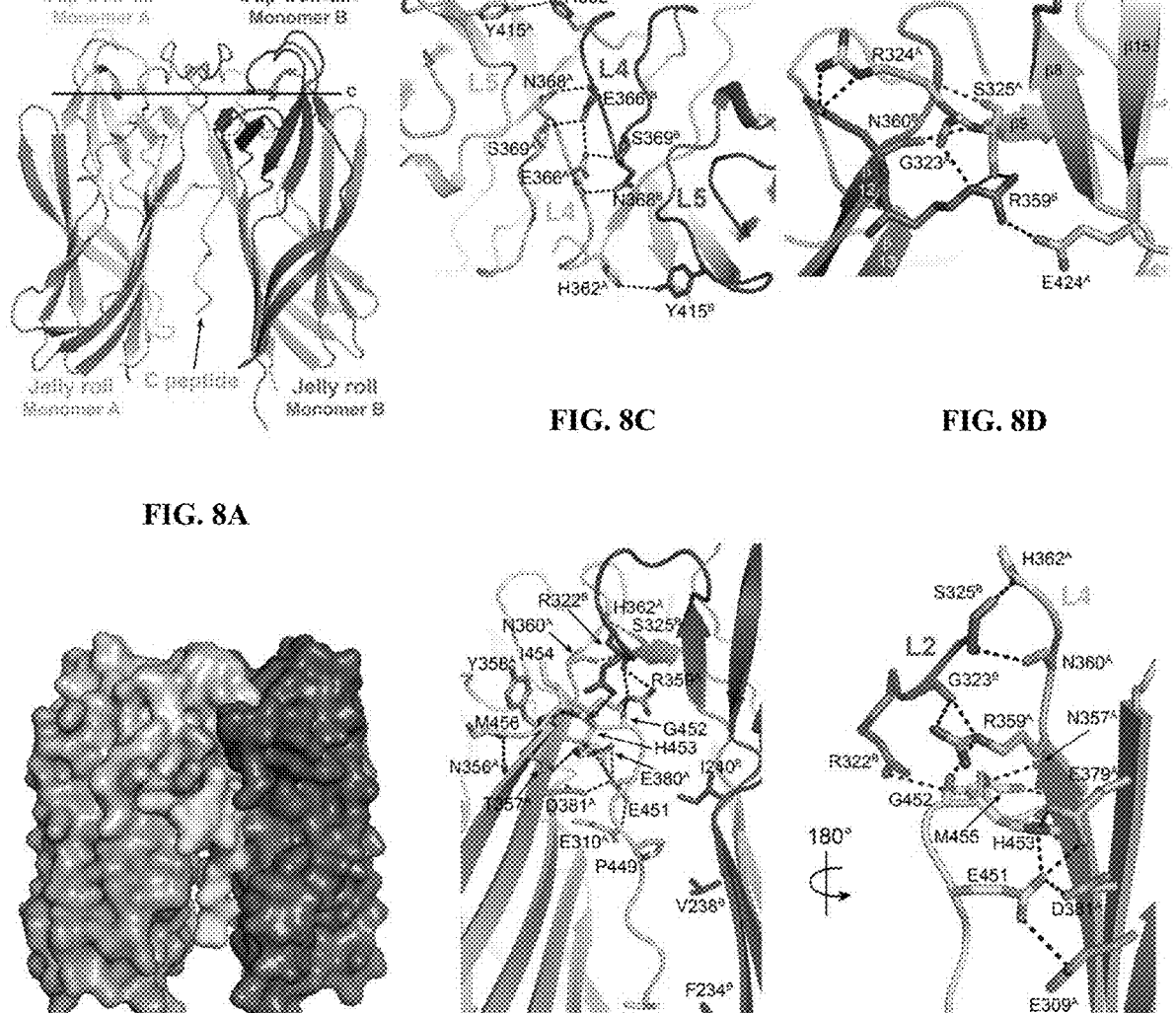

P/E/L virus $^N$RTDs crystallize as dimers (FIG. 1E, FIG. 1F), consistent with their stoichiometry in solution. Individual monomers superimpose with an overall RMSD ranging from 1.12-1.42 Å across all atoms, with the L2, β4-35, and β13-14 loops and portions of the C peptide exhibiting the greatest degree of structural variability (FIG. 3D). Within each dimer, $^N$RTD monomers are oriented parallel to the dimer symmetry axis with the sheet 1 side of the jelly roll facing inward (FIG. 7A, FIG. 7B, FIG. 8A, FIG. 8B). Cap domain loops L4 and L5 form the upper portion of the TuYV dimer interface, with main chain atoms and residues E315, H356, E360, N362, and Y410 of SEQ ID NO: 13 (H362, E366, N368, S369, and Y415 of SEQ ID NO: 1) making hydrogen bonds in trans (FIG. 7C, FIG. 7D, FIG. 8C, FIG. 8D). Interacting side chains from β12, L2, and β9 provide additional contacts at the edges of the dimer (FIG. 7D, FIG. 8D). The C peptides snake up from the bottom of the TuYV jelly roll, filling the large cavity beneath the cap domains before exiting in opposite directions to wrap around sheet 2 (FIG. 6C). The R440 and R443 side chains of SEQ ID NO: 13 anchor an extensive network of stabilizing hydrogen bonds and hydrophobic interactions along interior of the structure while β17 serves a similar role on the exterior (FIG. 7E). Together, the C peptides increase the total buried surface area from 908 Å$^2$ to 3615 Å$^2$, constituting a major driving force of dimerization. Although we only observe a partial fragment from one C peptide the PLRV $^N$RTD dimer (FIG. 6B, FIG. 8A, FIG. 8B), this piece forms similar stabilizing interactions with both monomers (FIG. 8E). ConSurf analysis shows that many of residues directly contacting the TuYV C peptides are highly conserved across all P/E/L viruses (FIG. 9A, FIG. 21A, FIG. 21B). Moreover, deletion of the C peptide from either $^N$RTD expression construct renders the resulting protein insoluble. Together these data underscore the critical role the C peptide plays in the proper folding and stability of the $^N$RTD dimer.

Figures 10A, 10B, 10C, 10D, 10E, 10F:
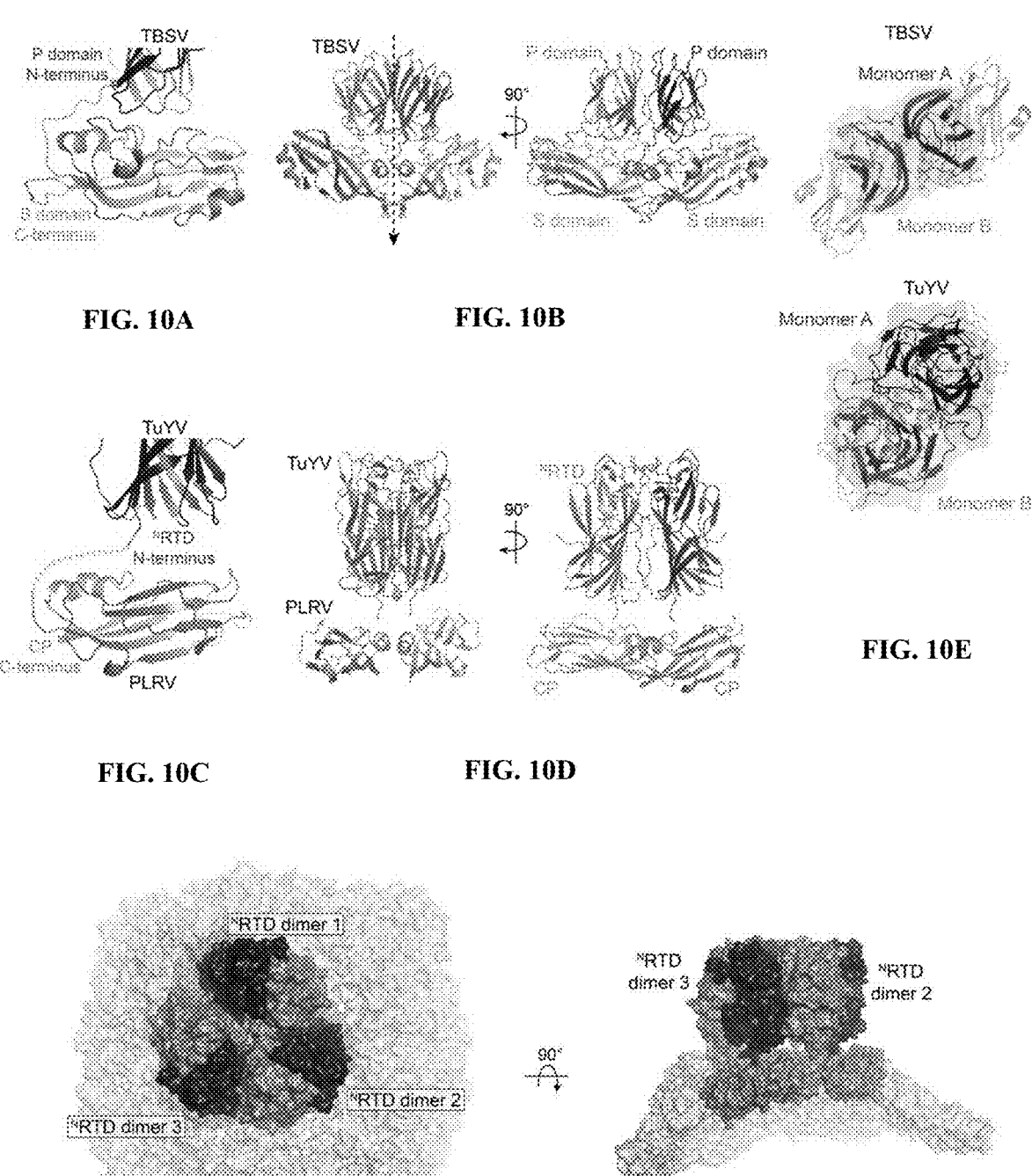
FIG. 10A, FIG. 10B, FIG. 10C, FIG. 10D, FIG. 10E and FIG. 10F provide pictorial representation showing the $^N$RTD architecture does not limit stoichiometry in the context of the mature virion.

$^N$RTD dimers are predicted, based on the structure, to sit atop the two-fold axis of symmetry on the assembled icosahedral virion as a head-to-head dimer. Stochastic ribosomal readthrough of the CP stop codon sub-stoichiometrically limits the amount of RTD present in mature, infectious virions. Why this has been evolutionarily maintained, despite its critical role in aphid transmission, is unknown. Leveraging the observed homology with tombusvirus structural proteins (FIG. 4A, FIG. 4B, FIG. 4C, FIG. 4D, FIG. 2A, FIG. 2B, FIG. 3C), we modelled the organization of the $^N$RTD on the capsid surface to identify possible restraints on virion assembly. Tombusvirid P domains are constitutively translated and tethered to each S domain via an unstructured linker (FIG. 10A). When assembled, the P domains occupy every two-fold symmetry axis in the T=3 icosahedral capsid (FIG. 10B, FIG. 2C). We anticipate that intact P/E/L virus RTPs will follow the same architectural blueprint but with the added constraint of head-to-head $^N$RTD dimerization imposed. A composite model combining the TuYV $^N$RTD and the PLRV CP coordinates suggests a similar overall connectivity (FIG. 10C), with the $^N$RTD dimer situated about the two-fold symmetry axis but rotated approximately 15° relative to the position of the TBSV P domains (FIG. 10D, FIG. 10E). Importantly, we note no steric clashing if this RTP model is placed at each position in the T=3 icosahedral asymmetric unit (FIG. 10F). This implies that the $^N$RTD could feasibly occupy every two-fold position in a polerovirus capsid and that the architecture of the $^N$RTD itself does not intrinsically limit its stoichiometry. The close proximity of this arrangement, however, might be problematic in that it could promote aggregation and/or collision between the disordered C-terminal region of the RTD in neighboring subunits, ultimately destabilizing the structure or masking segments of the RTD that interact with aphid receptors. We speculate that the leaky CP stop codon is therefore preserved to ensure a low concentration of this bulky C-terminal extension on the virion surface.

Example 2

$^N$RTD Reduces Aphid Transmission

Figure 11:
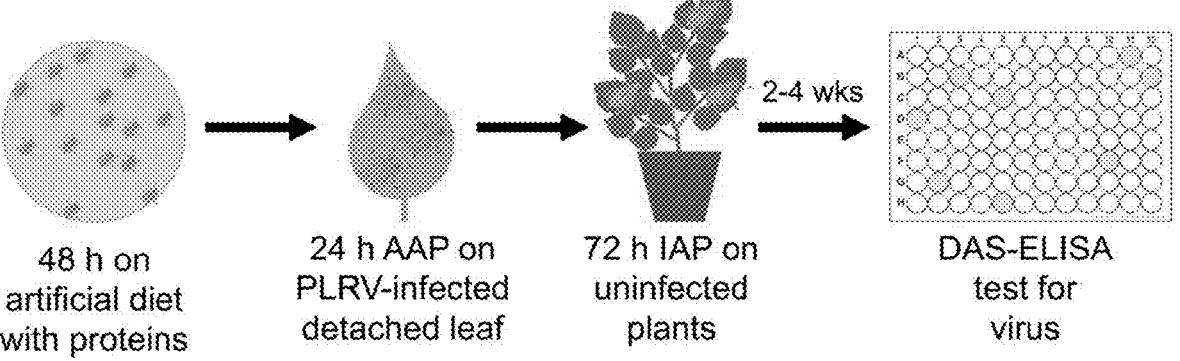
FIG. 11 provides a pictorial depiction of the experimental design for artificial diet feeding experiments. Aphids fed on artificial sucrose diet treatments containing the PLRV $^N$RTD, BSA, or no protein control for 48 hours. Then, aphids were moved to PLRV-infected detached hairy nightshade leaves to acquire virus for a 24-hour acquisition access period (AAP). Next, aphids were moved to uninfected potato plants (cv. Red Maria) for a 72-hour an inoculation access period (IAP), 3-5 aphids/plant, 5-16 plants/treatment. After the IAP, aphids were killed by a pesticide application. After several weeks, the inoculated plants are tested for systemic PLRV infection via DAS-ELISA.

We developed a virus transmission assay to test whether the PLRV $^N$RTD dimer can compete with the virus for binding to aphid tissues (FIG. 11). Experiments were conducted to test whether the $^N$RTD blocks virus transmission by aphids. The potato leafroll virus sequence used for recombinant $^N$RTD protein expression (SEQ ID NO: 2) is from a cDNA infectious clone. This infectious clone was used to inoculate hairy nightshade (Solanum sarrachoides, HNS) for use as a source of inoculum for all virus experiments. The parthenogenetic clone of Myzus persicae Sulz used in these experiments, originally collected from New York state, was maintained on Physalis floridana.

Artificial diet delivery of the PLRV $^N$RTD (purified as described above) and the control protein, bovine serum albumin (BSA, BioRad), was achieved by diluting the proteins to 0.1 mg/mL in an artificial sucrose diet for M. persicae supplemented with amino acids. Diet with no added protein was used as a control. After starving for 1-2 hours, M. persicae were placed in dishes that were sealed by stretching Parafilm over the top and sandwiching the diet beneath a second piece of Parafilm. Aphids were allowed 48 hours of feeding on the diet treatments: no protein control (n=63), BSA (n=74) and PLRV $^N$RTD (n=82).

For microinjection, purified PLRV $^N$RTD or BSA were diluted to 0.1 mg/mL or 1 mg/mL in phosphate-buffered saline (PBS). M. persicae aphids (50 aphids/treatment) were individually injected via a glass micro-capillary tube with ~1 μL of PBS (n=19), PLRV $^N$RTD (SEQ ID NO: 2) (n=38), or BSA (n=40) solutions in the ventral thorax or abdomen. Successful microinjection was visually confirmed by swelling of the insect.

Immediately following artificial diet feeding, microinjection, or in planta delivery (see below), aphids were transferred to detached PLRV-infected HNS leaves for a 24-hour acquisition access period (AAP). After the AAP, 3 aphids per plant (the first two oral delivery experiments, both microinjection experiments) or 5 aphids per plant (the third and fourth artificial delivery experiments) were transferred to uninfected potato seedlings (Solanum tuberosum cv. Red Maria, 6-15 plants/treatment) for a 72-hour inoculation access period (IAP). Potato seedlings were treated with pymetrozine (Endeavor) and bifenthrin (Talstar P) after the IAP to remove aphids. Systemic PLRV infection was accessed three weeks later by double antibody sandwich enzyme-linked immunosorbent assay (DAS-ELISA) using a polyclonal antibody generated towards purified PLRV (Agdia). Each inoculated plant represents a replicate. The artificial diet experiment was repeated five times independently and the microinjection experiments were repeated twice independently.

Figure 13A:
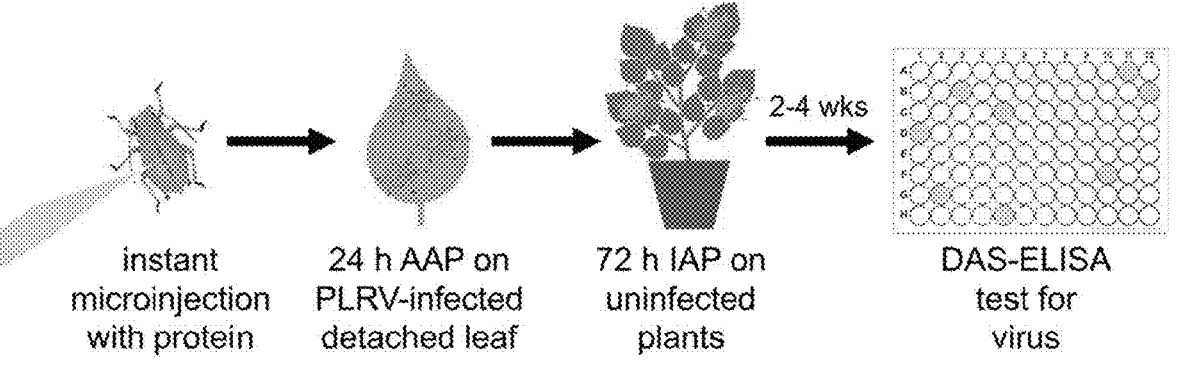
FIG. 13A, and FIG. 13B provide pictorial and graphic data of microinjection of aphids with PLRV $^N$RTD.
Figure 13B:
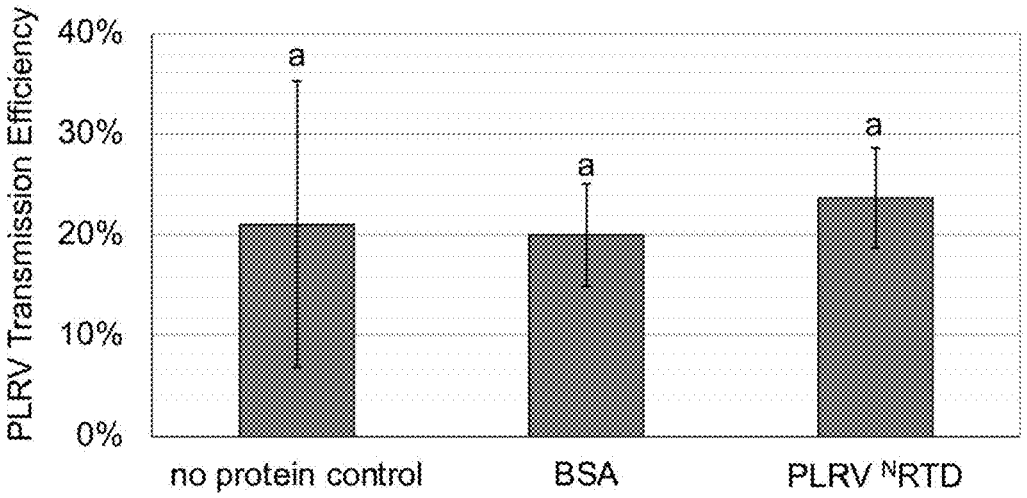

When M. persicae aphids, the primary vector of PLRV, are exposed to the purified $^N$RTD dimer in a membrane feeding cassette prior to PLRV acquisition (FIG. 11), transmission of PLRV to potato is significantly decreased as compared to the no protein control (FIG. 12A and Table 2, P=0.046), despite the fact that oral delivery of the same concentration of BSA significantly increases transmission (compared to the no protein control, P=0.035; compared to $^N$RTD, P<0.0001), a well-described phenotype in the literature observed for many proteins, including BSA, casein, lysozyme and cytochrome C. These data support the role of the $^N$RTD in facilitating interactions with aphid receptors or other proteins in aphid gut epithelial cells. To see if the $^N$RTD interacts with accessory salivary glands, aphids were microinjected with the purified PLRV $^N$RTD (SEQ ID NO: 2) prior to performing the transmission assay (FIG. 13A and Table 3). Microinjection bypasses the gut and delivers $^N$RTD directly to the aphid body cavity, which facilities possible interactions with the accessory salivary glands. No change in transmission was observed when two different concentrations of purified $^N$RTD were microinjected into the hemocoel (FIG. 13B and Table 4, compared to no protein control, P=0.694; compared to BSA control, P=0.820), indicating that the ability of the $^N$RTD alone to interfere with virus transmission occurs at the gut and not the accessory salivary glands.

TABLE 2

Logistic regression analysis of PLRV transmission by *M. persicae* aphids after artificial diet delivery of PLRV [N]RTD.

| Predictor[a] | b | SE b | Wald z | df | Pr > \|z\| |
|---|---|---|---|---|---|
| Intercept | −1.253 | ±0.303 | −4.134 | 1 | <0.001 *** |
| Treatment[b] (vs. no protein control) | | | | | |
| BSA | 0.813 | ±0.385 | 2.110 | 1 | 0.035 * |
| PLRV [N]RTD | −0.958 | ±0.480 | −1.996 | 1 | 0.046 * |

| Test | $H_o$ | $c^2$ | df | $P > c^2$ |
|---|---|---|---|---|
| Removing Exp[c] from Model | $b_{Exp} = 0$ | 9.42 | 4 | 0.051 |
| BSA vs. WT [N]RTD | $b_{BSA} = b_{PLRV\ NRTD}$ | 16.1 | 1 | <0.001 *** |
| Overall Model Evaluation | | | | |
| Likelihood Ratio Test | $b_{BSA} = b_{PLRV\ NRTD} = 0$ | 19.12 | 2 | <0.001 *** |
| Wald Test | $b_{BSA} = b_{PLRV\ NRTD} = 0$ | 16.7 | 2 | <0.001 *** |
| Goodness-of-Fit Test | the model fits | 218.06 | 215 | 0.429 |

Legend for Table 2:
[a]Model output is the categorical variable "InfectionState" with levels
0 = uninfected and
1 = PLRV-infected indicated whether the inoculated plant became systemically infected;
[b]"Treatment" is a categorical variable with levels
0 = no protein control,
1 = BSA,
2 = PLRV [N]RTD;
[c]"Exp" is a categorical variable representing the different trials of the experiment; and
Abbreviations:
PLRV, Potato leafroll virus;
SE, standard error;
df, degrees of freedom;
$H_0$, null hypothesis.

TABLE 3

PLRV transmission by *M. persicae* aphids after microinjection of PLRV [N]RTD.

| | No Protein Control | | | BSA | | PLRV [N]RTD | |
|---|---|---|---|---|---|---|---|
| Exp | Infected/ Total | Transmission Efficiency[a] | Conc | Infected/ Total | Transmission Efficiency[a] | Infected/ Total | Transmission Efficiency[a] |
| 1 | 3/8 | 38% | 0.1 mg/mL | 2/12 | 17% | 2/10 | 20% |
| | | | 1 mg/mL | 2/6 | 33% | 2/11 | 18% |
| 2 | 1/11 | 9% | 0.1 mg/mL | 3/12 | 25% | 3/12 | 25% |
| | | | 1 mg/mL | 1/10 | 10% | 2/5 | 40% |
| Total | 4/19 | 21% | | 8/40 | 20% | 9/38 | 24% |

Legend for Table 3:
[a]Percent of plants that become systemically infected with PLRV after inoculation by aphids exposed to no protein control, BSA, or PLRV [N]RTD.
Aphids were microinjected, followed by a 24-hour acquisition access period and 72-h inoculation access period with 3 aphids/plants.
Plants were tested for virus via ELISA 4 weeks post inoculation.; and
Abbreviations:
PLRV, Potato leafroll virus;
EXP, Experiment;
Conc, concentration

TABLE 4

Logistic regression analysis of PLRV transmission by *M. persicae* aphids after microinjection of PLRV [N]RTD.

| Predictor[a] | b | SE b | Wald z | df | Pr > \|z\| |
|---|---|---|---|---|---|
| Intercept | −1.386 | ±0.395 | −3.507 | 1 | <0.001 *** |
| Treatment[b] (vs. no protein control) | | | | | |
| BSA | 0.065 | ±0.688 | 0.094 | 1 | 0.925 |
| PLRV [N]RTD | 0.216 | ±0.549 | 0.394 | 1 | 0.694 |

TABLE 4-continued

| Logistic regression analysis of PLRV transmission by M. persicae aphids after microinjection of PLRV $^N$RTD. | | | | |
|---|---|---|---|---|
| Test | H$_o$ | $c^2$ | df | P > $c^2$ |
| Removing Exp$^c$ from Model | b$_{Exp}$ = 0 | 0.04 | 1 | 0.718 |
| BSA vs. PLRV $^N$RTD | b$_{BSA}$ = b$_{WT\,NRTD}$ | 0.05 | 1 | 0.820 |
| | Overall Model Evaluation | | | |
| Likelihood Ratio Test | b$_{BSA}$ = b$_{PLRV\,NRTD}$ = 0 | 0.25 | 2 | 1.000 |
| Wald Test | b$_{BSA}$ = b$_{PLRV\,NRTD}$ = 0 | 0.16 | 2 | 0.920 |
| Goodness-of-Fit Test | the model fits | 101.19 | 94 | 0.288 |

Legand for Table 4:
$^a$Model output is the categorical variable "InfectionState" with levels
0 = uninfected and
1 = PLRV-infected indicated whether the inoculated plant became systemically infected;
$^b$"Treatment" is a categorical variable with levels
0 = no protein control,
1 = BSA,
2 = PLRV $^N$RTD;
$^c$"Exp" is a categorical variable representing the different trials of the experiment; and
Abbreviations:
SE, standard error;
df, degrees of freedom;
H$_0$, null hypothesis.

These data are consistent with previous mutational analyses that have shown the $^N$RTD to be important for virus passage through the aphid gut. The $^N$RTD dimer may be a part of the conserved protein structural features of P/E/L virus capsids that regulate interactions with the aphid gut. The purified PLRV $^N$RTD dimer may competitively inhibit PLRV adherence to aphid gut epithelial cells or otherwise block interactions necessary for PLRV transit across the gut. This finding has great potential applications as a novel strategy to slow virus transmission in an agricultural setting.

Example 3

$^N$RTD Reduces Aphid Transmission of PLRV when Delivered in Planta

To begin translating this discovery to a format that could be deployed in the field, we developed a system to transiently express the $^N$RTD in planta using Agrobacterium tumefaciens (FIG. 14A, FIG. 14B, FIG. 14C, FIG. 14D, FIG. 14E, FIG. 14F). For in planta delivery, transient expression constructs were generated by cloning the PLRV $^N$RTD sequence into pEarlyGate binary expression vectors, creating untagged and YFP-tagged versions of the PLRV $^N$RTD, with YFP adhered to the N- or C-terminus. Expression and solubility of these constructs was tested in planta via agroinfiltration into Nicotiana benthamiana. Three leaves per plants, 3 plants per construct were infiltrated, and leaf discs taken at 2-, 3-, and 4-days post inoculation (dpi) for subsequent protein extraction and western blot analysis. Protein was extracted by cryogenic grinding of leaf discs for 6 min at 25 Hz in a Mixer Mill 440 (Retsch) followed by resuspension in extraction buffer (0.1 M Trist pH 8.0, 150 mM NaCl, 20 mM HEPES pH 7.0). Protein extracts were combined with Laemmli buffer (BioRad), separated by SDS-PAGE and analyzed by western blot with the anti-$^N$RTD antibody as described above. The integrity of the YFP tag was confirmed by western blot analysis with 1:5000 anti-GFP polyclonal antibody (Abcam).

To test the ability of aphids to transmit PLRV after exposure to the $^N$RTD via in planta expression, N. benthamiana leaves were infiltrated with 35:YFP-$^N$RTD, 35S:$^N$RTD-YFP, or 35S:GFP (control) constructs. At 2 dpi, aphids were caged on the protein-expressing leaves as well an uninfiltrated (control) leaves for 48 hours. Then aphids were moved to PLRV-infected detached HNS leaves for 24 hours, and health potato seedlings for 72 hours (5 aphids/plant, 10-15 plants/treatment), as in the artificial diet and microinjection experiments described above. Aphids were removed by a pesticide application and systemic PLRV infection of the potato plants was assessed via DAS-ELISA 2-4 weeks post inoculation. Each inoculated plant represents a replicate (n=37 for all treatments). The experiment was repeated three times independently.

Expression tests and western blot analysis showed that the PLRV $^N$RTD requires a small protein tag to facilitate folding in planta (FIG. 14A, FIG. 14B, FIG. 14C, FIG. 14D). Aphids were allowed to feed on Nicotiana benthamiana leaves transiently expressing the YFP-tagged PLRV $^N$RTD before testing their ability to transmit virus (FIG. 14E). Aphids pre-exposed to the $^N$RTD by this delivery method also had a decreased ability to transmit virus (FIG. 14F and Table 4, compared to uninfiltrated control, P=0.011). A meta-analysis of these transmission assays (FIG. 12D) can pool the results of these transmission studies and calculate the risk of a plant becoming infected after aphid exposure to the PLRV $^N$RTD relative to the no protein control (risk ratio) and a 95% confidence interval of that ratio (FIG. 12D, in brackets) for all trials of the experiment, broken down into delivery via artificial diet or in planta, as well as the pooled overall effect (FIG. 12D, black diamond). Overall, this meta-analysis found that pre-treatment of aphids with the PLRV $^N$RTD can significantly reduce the chances of a plant from becoming infected by over half (risk ratio of 0.44) with the 95% confidence interval ranging from a 12% reduction in infection (risk ratio of 0.88) to 88% reduction (risk ratio of 0.22, FIG. 12D). There was remarkably low heterogeneity between experiments and even between delivery methods ($I^2$=0%, $\tau^2$=0, with p-values greater than 0.40) indicating that this effect is highly reproducible.

The same construct used in the transient in planta expression tests was used to generate transgenic potato plants. To generate this plasmid for transformation and expression in potato, the cassette containing 35S: YFP-$^N$RTD from the pEarleyGate104 backbone used for transient expression in

Figure 15:
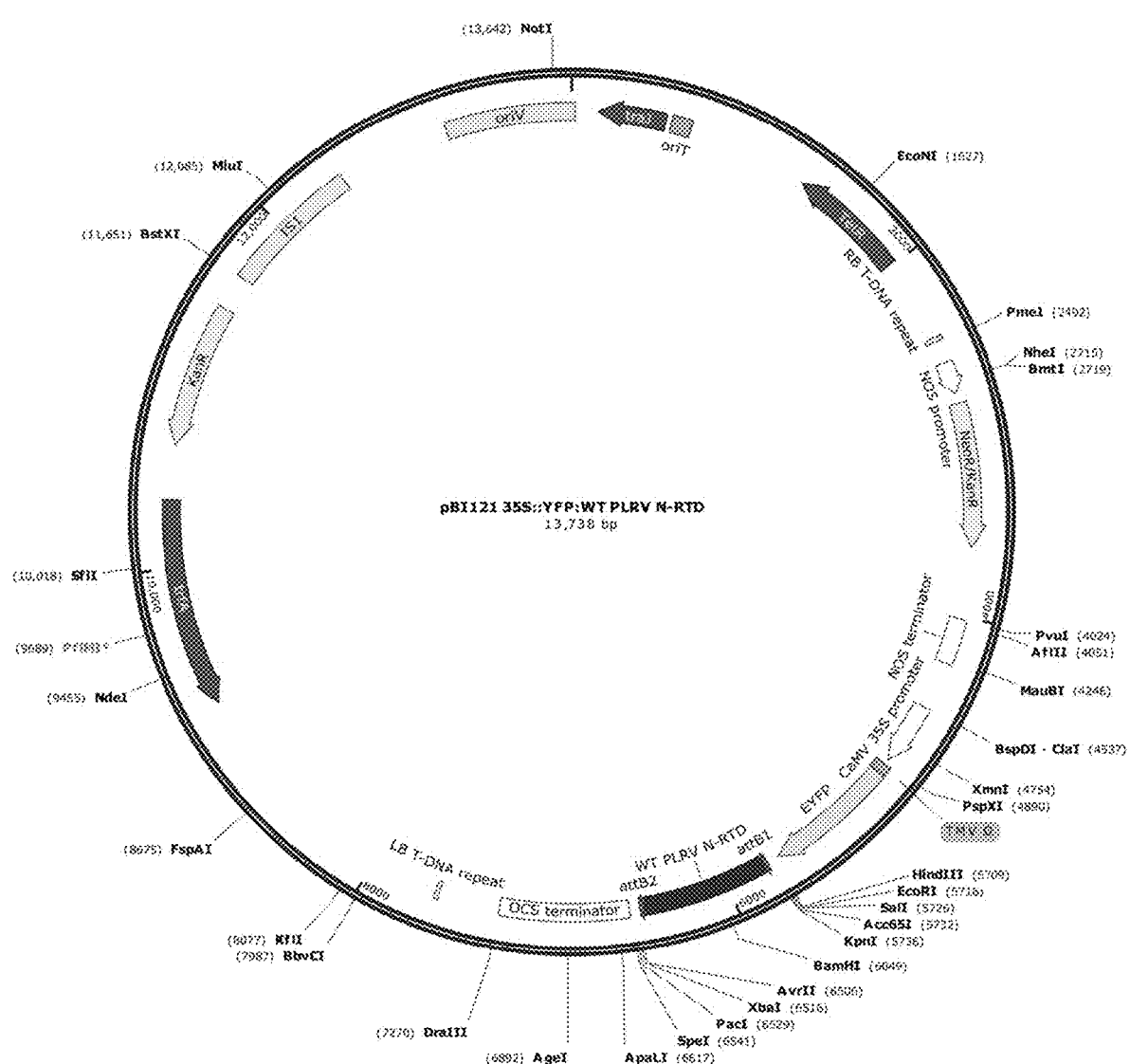
FIG. 15 provides pictorial representation of the plasmid (pBI121 35S::YFP:WT PLRV $^N$RTD) used to generate transgenic potato plants. The plasmid consists of the CaMV 35S promoter, followed by the TMV omega translational enhance, EYFP, the PLRV $^N$RTD (SEQ ID NO: 2), and the OCS transcriptional terminator.

*N. benthamiana* was cloned between the ClaI (nucleotide position 4537) and DraIII (8290) restriction sites in pBI121, resulting in a final plasmid size of 13.7 kb. The full cassette cloned into pBI121 consists of the CaMV 35S promoter, followed by the TMV omega translational enhance, EYFP, the PLRV $^N$RTD, and the OCS transcriptional terminator. The original fragment between ClaI and DraIII in the pBI121 empty vector was excised and discarded and replaced with this cassette (FIG. 15).

A total of 10 transgenic potato lines (Desiree) were generated and confirmed to express the $^N$RTD using RT-PCR according to published protocols. To test whether the PLRV titer in aphids is impacted by feeding on YFP-$^N$RTD expressing potato plants, we used reverse transcriptase-digital droplet PCR (ddPCR) to measure the PLRV titer in viruliferous aphids pre-fed on YFP-$^N$RTD plants. First, aphids were given a 48-hour acquisition access period on YFP-$^N$RTD expressing transgenic potato plants, and an empty vector control plant. Immediately after, aphids were given a 48-hour acquisition access period on PLRV infected HNS (*S. sarrachoides*) plants. Aphids were collected and immediately flash frozen with liquid nitrogen following virus acquisition. RNA was extracted from two tubes of five aphids per treatment (10 aphids per treatment), by cryo-grinding the aphids twice using a Retch Mixer Mill 400 for three minutes at 30 hz. Following homogenization, aphid RNA was extracted using the Zymo Quick-DNA/RNA Mini-prep kit following the manufacturer's instructions. RNA quality was measured using a nanodrop. cDNA synthesis was performed using a minimum of 500 ng and a maximum of 1 ug into each reverse-transcriptase reaction using the Bio-Rad iScript kit with a mix of Oligo dT's and random hexamers. The thermocycling conditions started at 5 minutes at 25° C., 20 minutes at 46° C., ending at 1 minute at 95° C.

Digital droplet PCR reactions were conducted using the QX200 digital droplet PCR system (Bio-Rad). Each ddPCR reaction contained 10 µL of 2×ddPCR Evagreen SuperMix (Bio-Rad), 0.5 µL of each of the 10 µM PLRV primers, FP and RP, 7 µL of RT-grade H2O, and 2 µL of cDNA at correct dilution (100 ng total) for a final volume of 20 µL per reaction. The entire 20 µL reaction and 70 µL of droplet generation oil for Evagreen (Bio-Rad) was placed into the QX100 droplet generator (Bio-Rad), to generate 40 µL droplets. The Droplets were transferred to a partitioned 96-well plate (Eppendorf) and sealed with easy pierce foil (Bio-Rad). PCR amplification on an Applied Biosystems 2720 Thermocycler was carried out with the following conditions: 5 minutes at 95° C., 40 cycles of 95° C. for 30 seconds and one minute at 60° C., 1 cycle for 5 minutes at 4° C., one cycle for 5 minutes at 90° C., and ending at 12° C. Immediately following amplification, the plate was inserted into the droplet reader cassette (Bio-Rad) and loaded into the droplet reader (Bio-Rad). The droplets were read at a rate of 8 wells per 15 minutes. The ddPCR droplet data was analyzed using the Quantasoft analysis software (Bio-Rad). The results are measured by copies of target per microliter of PCR mixture. The number of copies of PLRV per microliter was compared between treatments using Student's t-test, (P=0.038). The results show that lines 2a and b significantly reduce PLRV transmission when aphids are pre-fed the transgenic potato plants (FIG. 19, P<0.05).

Example 4

Cap Domain Mutants Lethal to the Vector

Figure 16:
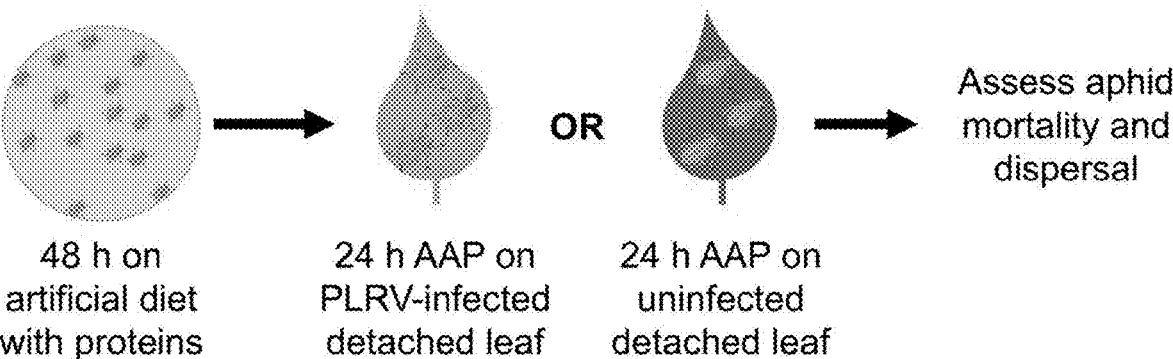
FIG. 16 provides pictorial representation of the experimental design for aphid mortality and dispersal experiments. Age-synchronized *M. persicae* aphids were allowed to feed on 0.1 mg/mL of BSA, WT PLRV $^N$RTD (SEQ ID NO: 2) or PLRV $^N$RTD point mutants SEQ ID NO: 5, SEQ ID NO: 6, SEQ ID NO: 7 or one cluster mutant (SEQ ID NO: 8; containing the three mutations N368A, C370A, Y411A) in artificial diet for 48 hours before being moved to a PLRV-infected or uninfected detached HNS leaf. After 24 hours on the HNS leaves, mortality of *M. persicae* aphids was tallied on and off the leaf for each treatment and leaf combination.

To test our hypothesis that the cap domain serves as the interface for interaction with the aphid vector, several mutations were made in surface-exposed residues of the cap domain of the PLRV $^N$RTD, including alanine substitution point mutations at residues H321, E366, H371, E374, and a single "cluster" mutant containing three alanine substitution point mutations at N368, C370, Y411 in SEQ ID NO: 1; these correspond the $^N$RTD sequences SEQ ID NO: 4, SEQ ID NO: 5, SEQ ID NO: 6, SEQ ID NO: 7, and SEQ ID NO: 8, respectively. Each point mutation was made in a non-conserved residue whereas the cluster mutations were in highly conserved residues (FIG. 9B, FIG. 9C, FIG. 9D, FIG. 21A, FIG. 21B). These mutations were specifically designed to not interfere with $^N$RTD dimerization and folding. Each mutant $^N$RTD construct was purified individually and delivered to aphids via artificial sucrose diet for 48 hours, after which aphids were moved to PLRV-infected or uninfected HNS leaves (FIG. 16). While originally intended to assess PLRV transmission, we noted that aphids died at a significant rate after exposure to several of the mutant forms of the PLRV $^N$RTD, with some mutants causing near complete mortality (FIG. 12C).

Thus, the experiment was repeated and fully replicated to assess the reproducibility of the mortality phenotype. Mortality of *M. persicae* on various mutants of the PLRV $^N$RTD delivered via artificial diet was assessed using age-synchronized fourth instar nymphs and adults. Aphids were synchronized by placing adult *M. persicae* aphids on *Physalis floridana* leaves for two days to lay nymphs. Adults were removed and nymphs were allowed to develop for a week (reaching fourth instar and adulthood) before being used in mortality assays. Purified BSA (n=232), WT PLRV $^N$RTD (SEQ ID NO: 2) (n=247), PLRV $^N$RTD point mutants SEQ ID NO: 4 (n=183), SEQ ID NO: 5 (n=118), SEQ ID NO: 6 (n=264), SEQ ID NO: 7 (n=161), or one cluster mutant SEQ ID NO: 8 (n=256) were diluted to 0.1 mg/mL in artificial sucrose diet. After starving for 1-2 hours, age-synchronized *M. persicae* aphids were allowed to feed on these proteins in membrane feeding cassettes (as well as a no added protein control) for 48 hours before being moved to a PLRV-infected or uninfected detached HNS leaf. After 24 hours on the HNS leaves, mortality of *M. persicae* aphids was tallied on and off the leaf for each treatment and leaf combination. Each individual aphid is considered a replicate. The experiment was repeated three times independently.

Mutants SEQ ID NO: 5, SEQ ID NO: 6, SEQ ID NO: 7 and the cluster mutant SEQ ID NO: 8 all caused significant mortality (P<0.001 for all four mutants, respectively, as compared to no protein control) with SEQ ID NO:7 and the cluster mutant SEQ ID NO: 8 causing the greatest mortality. The mutant SEQ ID NO: 4 did not cause significant mortality of the insects when compared to no protein and BSA controls (FIG. 12B, FIG. 12C, P>0.44). The fact that this particular mutation caused a different phenotype than the others can be explained by different localization in the structure (FIG. 21A, FIG. 21B). It seems perturbations to the amino acid pocket at positions 366-374 of SEQ ID NO: 1 (corresponding to residues 137-145 in SEQ ID NO: 2 and SEQ ID NO: 3) results in mortality of the insect whereas changes to H321 of SEQ ID NO: 1 (corresponding to residue H92 in SEQ ID NO: 2 and SEQ ID NO: 3) are better tolerated. Importantly, SEQ ID NO: 4 does not block virus transmission, indicating that this particular mutation changes the interaction with the $^N$RTD aphid receptor or other aphid protein in a way that is distinct from the other mutations.

Figure 22:
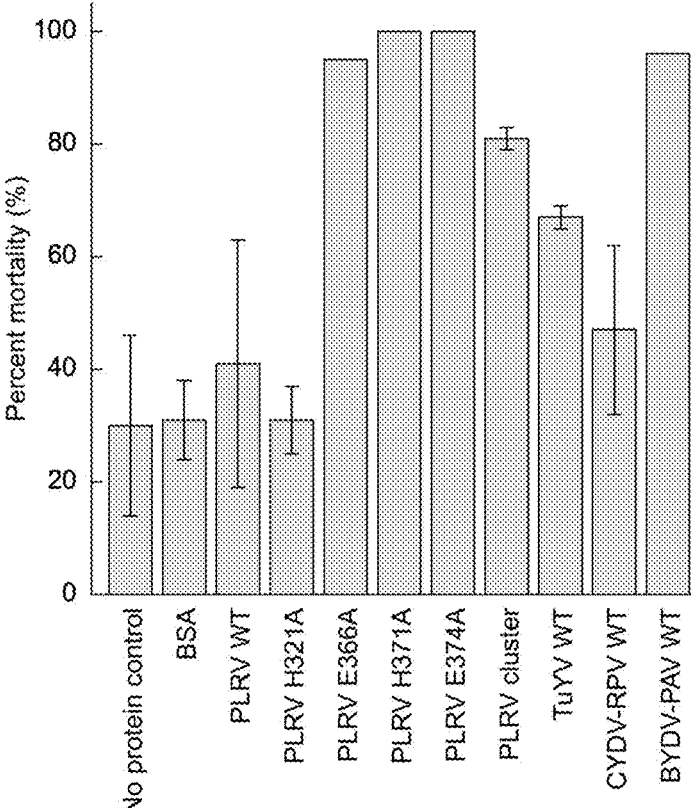
FIG. 22 provides graphical representation of data showing that $^N$RTD proteins can be a used as tool to kill *A. gossypii*. The cotton aphid *Aphis gossypii* mortality after feeding on 0.1 mg/mL of no protein control (n=47), BSA (n=45), the WT PLRV $^N$RTD SEQ ID NO: 2 (n=46), PLRV $^N$RTD with the point mutations SEQ ID NO: 4 (n=49), SEQ ID NO: 5 (n=41), SEQ ID NO: 6 (n=42), SEQ ID NO: 7 (n=44), SEQ ID NO: 8 (n=48), the TuYV WT $^N$RTD SEQ ID NO: 14 (n=46), the CYDV-RPV WT $^N$RTD SEQ ID NO: 19 (n=45), or the BYDV-PAV WT $^N$RTD SEQ ID NO: 21 (n=45), for 96 hours. Percent mortality was calculated at the end of the experiment by counting the number of dead and alive aphids remaining.

Aphid mortality was also tested in a second aphid species, *Aphis gossypii*. Clonally reproducing colonies of *A. gossypii* were used to test the toxicity of PLRV WT and mutant $^N$RTD proteins SEQ ID NO: 2 (n=46), SEQ ID NO: 4 (n=49), SEQ ID NO: 5 (n=41), SEQ ID NO: 6 (n=42), SEQ ID NO: 7 (n=44), and SEQ ID NO: 8 (n=48), using artificial diet delivery on sucrose diets containing 0.1 mg/mL protein (FIG. 22). WT <sup>N</sup>RTDs from the were also tested from other poleroviruses (TuYV SEQ ID NO: 14, CYDV-PAV SEQ ID NO: 19) and a luteovirus (BYDV-PAV SEQ ID NO: 21). Adults were collected from a parthogenetically-reproducing colony maintained on cotton and the experiment was repeated twice. At least 40 aphids were evaluated for each treatment. The percent mortality was calculated after aphids fed on the artificial diet solutions for 96 hours. PLRV mutants SEQ ID NO: 5, SEQ ID NO: 6, and SEQ ID NO: 7 all caused 95-100% mortality in this context while the cluster mutant SEQ ID NO: 8 induced nearly 80% mortality. Other viral <sup>N</sup>RTDs showed differing degrees of lethality, with the corresponding segments from TuYV SEQ ID NO: 14 and CLRDV-RPV SEQ ID NO: 19 killing 60% and 40% of the aphids, respectively, while the BYDV-PAV <sup>N</sup>RTD SEQ ID NO: 21 induced nearly 100% mortality.

Example 5

Figure 17:
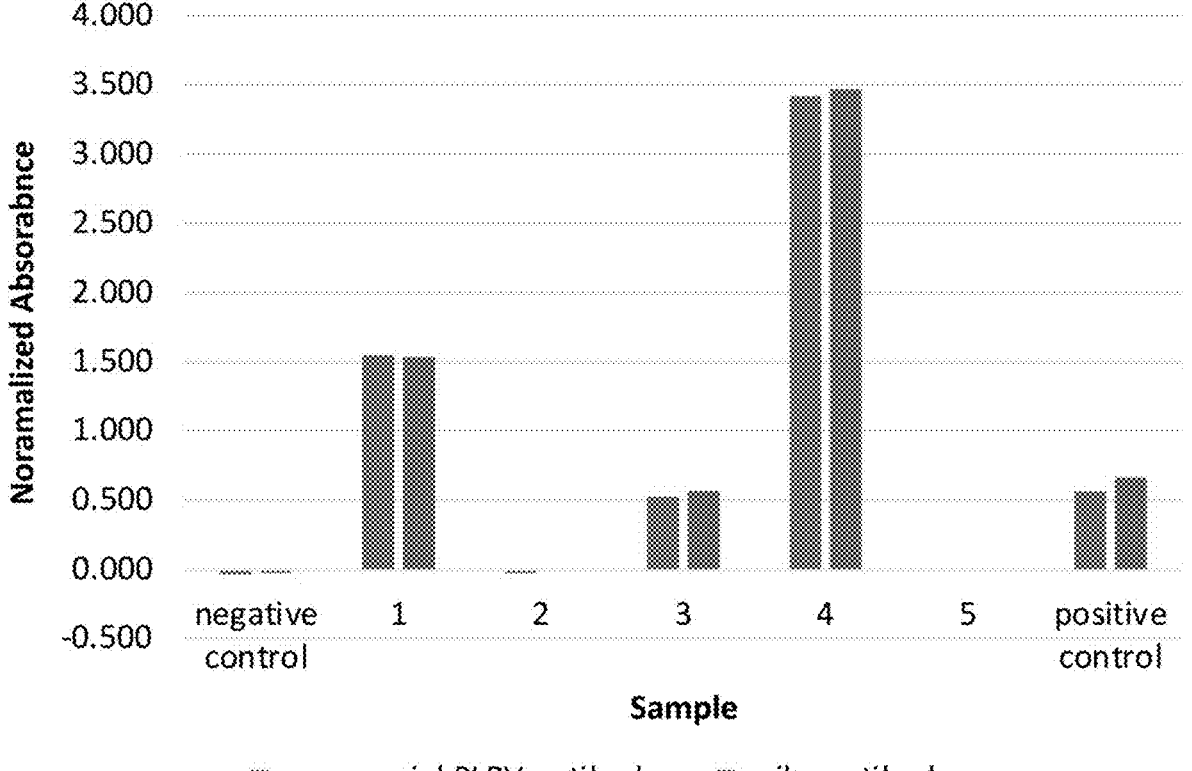
FIG. 17 provides graphic representation of data showing PLRV virus detection by ELISA. Assays used either the commercial Agdia PLRV antibody (blue) or the polyclonal spike antibody raised against purified PLRV $^N$RTD (red; serum, not cross absorbed) as the coating/capture antibody. The commercial Agdia PLRV-AP conjugate was used as the conjugate/detection antibody.
Figure 18:
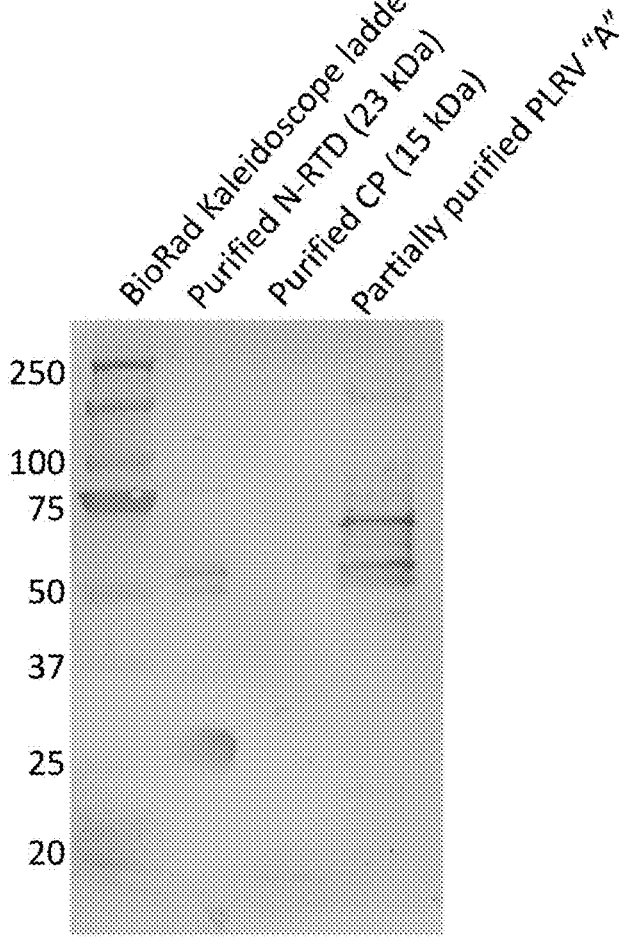
FIG. 18 provides results of western blot analysis using polyclonal PLRV $^N$RTD antibody. Antibody serum (not cross absorbed) raised against the PLRV $^N$RTD recognizes the $^N$RTD as a recombinant protein and when it is incorporated into partially purified virions without cross reacting with the PLRV CP.
Figure 20:
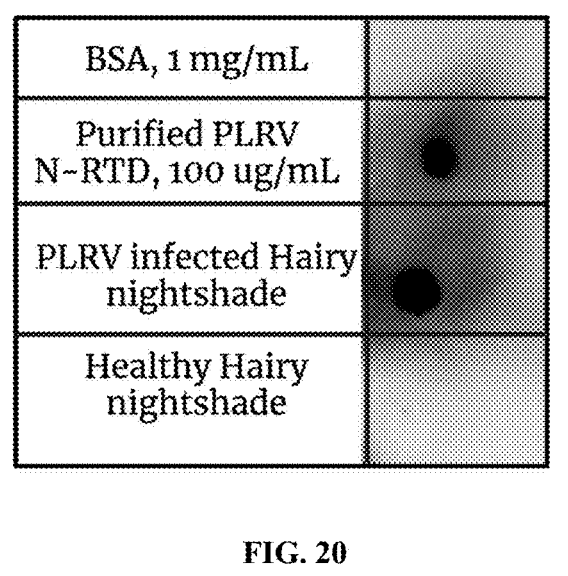

Antibodies and Camelid-VHHs Produced to the <sup>N</sup>RTD are Useful for Virus Detection The <sup>N</sup>RTD was useful in generating polyclonal antibodies in rabbits that recognize PLRV-infected plants with sensitivity and specificity of commercially available antibodies in ELISA (FIG. 17), showing the <sup>N</sup>RTD is useful as an antigen for antibody production (FIG. 17, FIG. 18). By Western blot analysis, the <sup>N</sup>RTD polyclonal antibody recognizes the <sup>N</sup>RTD when it is incorporated into virions and does not appear to cross-react with the purified CP (FIG. 18). Additionally, the soluble <sup>N</sup>RTD was useful to develop three camelid VHH nanobodies (SEQ ID NO: 15, SEQ ID NO: 16, SEQ ID NO: 17) that bind to the PLRV <sup>N</sup>RTD. The PLRV nanobodies can be useful as a detection tool, or to express in plants to provide plant resistance to PLRV infection by neutralizing the virus structural proteins prior to acquisition by aphid vectors. Specificity of one of these nanobodies, A7 (SEQ ID NO: 16), was determined by dot blot (FIG. 20).

While the invention has been described with reference to details of the illustrated embodiments, these details are not intended to limit the scope of the invention as defined in the appended claims. The embodiment of the invention in which exclusive property or privilege is claimed is defined as follows:

```
SEQUENCE LISTING

Sequence total quantity: 59
SEQ ID NO: 1              moltype = AA  length = 717
FEATURE                   Location/Qualifiers
source                    1..717
                          mol_type = protein
                          organism = potato leaf roll virus
SEQUENCE: 1
MSTVVVKGNV NGGVQQPRRR RRQSLRRRAN RVQPVVMVTA PGQPRRRRRR RGGNRRSRRT  60
GVPRGRGSSE TFVFTKDNLV GNSQGSFTFG PSLSDCPAFK DGILKAYHEY KITSILLQFV  120
SEASSTSSGS IAYELDPHCK VSSLQSYVNK FQITKGGAKT YQARMINGVE WHDSSEDQCR  180
ILWKGNGKSS DPAGSFRVTI RVALQNPKQV DSGSEPGPSP QPTPTPTPQK HERFIAYVGI  240
PMLTIQAREN DDQIILGSLG SQRMKYIEDE NQNYTNISSE YYSQSSMQAV PMYYFNVPKG  300
QWSVDISCEG YQPTSSTSDP HRGRSDGMIA YSNADSDYWN VGEADGVKIS KLRNDNTYRQ  360
GHPELEINSC HFREGQLLER DATISFHVEA PTDGRFFLVG PAIQKTAKYN YTISYGDWTD  420
RDMELGLITV VLDEHLEGTG SANRVRRPPR EGHIYMASPH EPEGKPVGNK PRDETPIQTQ  480
ERQPDQTPSD DVSDAGSVNS GGSTESLQLE FGANSDSTHD ATVDGTDWPR IPPPRHPPEL  540
RVSGNSRTVT DFSPKADLLE NWDAEHFDPG YSKEDVAAAT IIAHGSIQDG RSMLEKREEN  600
VKNKTSSWKP PLPKAVSPAI AKLRSIRKSQ PLEGGTLKKD ATDGVSSIGS GSLTGGTLKR  660
KATIEERLLQ TLTTEQRLWY ENLKKTNPPA ATQWLFEYQP PPQVDRNIAE NPFQGRK    717

SEQ ID NO: 2              moltype = AA  length = 229
FEATURE                   Location/Qualifiers
source                    1..229
                          mol_type = protein
                          organism = potato leaf roll virus
SEQUENCE: 2
KHERFIAYVG IPMLTIQARE NDDQIILGSL GSQRMKYIED ENQNYTNISS EYYSQSSMQA  60
VPMYYFNVPK GQWSVDISCE GYQPTSSTSD PHRGRSDGMI AYSNADSDYW NVGEADGVKI  120
SKLRNDNTYR QGHPELEINS CHFREGQLLE RDATISFHVE APTDGRFFLV GPAIQKTAKY  180
NYTISYGDWT DRDMELGLIT VVLDEHLEGT GSANRVRRPP REGHIYMAS            229

SEQ ID NO: 3              moltype = AA  length = 237
FEATURE                   Location/Qualifiers
source                    1..237
                          mol_type = protein
                          organism = potato leaf roll virus
SEQUENCE: 3
KHERFIAYVG IPMLTIQARE NDDQIILGSL GSQRMKYIED ENQNYTNISS EYYSQSSMQA  60
VPMYYFNVPK GQWSVDISCE GYQPTSSTSD PHRGRSDGMI AYSNADSDYW NVGEADGVKI  120
SKLRNDNTYR QGHPELEINS CHFREGQLLE RDATISFHVE APTDGRFFLV GPAIQKTAKY  180
NYTISYGDWT DRDMELGLIT VVLDEHLEGT GSANRVRRPP REGHIYMASP HEPEGKP     237

SEQ ID NO: 4              moltype = AA  length = 229
FEATURE                   Location/Qualifiers
source                    1..229
                          mol_type = protein
```

-continued

```
                            organism = synthetic construct
SEQUENCE: 4
KHERFIAYVG IPMLTIQARE NDDQIILGSL GSQRMKYIED ENQNYTNISS EYYSQSSMQA   60
VPMYYFNVPK GQWSVDISCE GYQPTSSTSD PARGRSDGMI AYSNADSDYW NVGEADGVKI   120
SKLRNDNTYR QGHPELEINS CHFREGQLLE RDATISFHVE APTDGRFFLV GPAIQKTAKY   180
NYTISYGDWT DRDMELGLIT VVLDEHLEGT GSANRVRRPP REGHIYMAS              229

SEQ ID NO: 5              moltype = AA  length = 229
FEATURE                   Location/Qualifiers
source                    1..229
                          mol_type = protein
                          organism = synthetic construct
SEQUENCE: 5
KHERFIAYVG IPMLTIQARE NDDQIILGSL GSQRMKYIED ENQNYTNISS EYYSQSSMQA   60
VPMYYFNVPK GQWSVDISCE GYQPTSSTSD PHRGRSDGMI AYSNADSDYW NVGEADGVKI   120
SKLRNDNTYR QGHPELAINS CHFREGQLLE RDATISFHVE APTDGRFFLV GPAIQKTAKY   180
NYTISYGDWT DRDMELGLIT VVLDEHLEGT GSANRVRRPP REGHIYMAS              229

SEQ ID NO: 6              moltype = AA  length = 229
FEATURE                   Location/Qualifiers
source                    1..229
                          mol_type = protein
                          organism = synthetic construct
SEQUENCE: 6
KHERFIAYVG IPMLTIQARE NDDQIILGSL GSQRMKYIED ENQNYTNISS EYYSQSSMQA   60
VPMYYFNVPK GQWSVDISCE GYQPTSSTSD PHRGRSDGMI AYSNADSDYW NVGEADGVKI   120
SKLRNDNTYR QGHPELEINS CAFREGQLLE RDATISFHVE APTDGRFFLV GPAIQKTAKY   180
NYTISYGDWT DRDMELGLIT VVLDEHLEGT GSANRVRRPP REGHIYMAS              229

SEQ ID NO: 7              moltype = AA  length = 229
FEATURE                   Location/Qualifiers
source                    1..229
                          mol_type = protein
                          organism = synthetic construct
SEQUENCE: 7
KHERFIAYVG IPMLTIQARE NDDQIILGSL GSQRMKYIED ENQNYTNISS EYYSQSSMQA   60
VPMYYFNVPK GQWSVDISCE GYQPTSSTSD PHRGRSDGMI AYSNADSDYW NVGEADGVKI   120
SKLRNDNTYR QGHPELEINS CHFRAGQLLE RDATISFHVE APTDGRFFLV GPAIQKTAKY   180
NYTISYGDWT DRDMELGLIT VVLDEHLEGT GSANRVRRPP REGHIYMAS              229

SEQ ID NO: 8              moltype = AA  length = 229
FEATURE                   Location/Qualifiers
source                    1..229
                          mol_type = protein
                          organism = synthetic construct
SEQUENCE: 8
KHERFIAYVG IPMLTIQARE NDDQIILGSL GSQRMKYIED ENQNYTNISS EYYSQSSMQA   60
VPMYYFNVPK GQWSVDISCE GYQPTSSTSD PHRGRSDGMI AYSNADSDYW NVGEADGVKI   120
SKLRNDNTYR QGHPELEIAS AHFREGQLLE RDATISFHVE APTDGRFFLV GPAIQKTAKY   180
NATISYGDWT DRDMELGLIT VVLDEHLEGT GSANRVRRPP REGHIYMAS              229

SEQ ID NO: 9              moltype = AA  length = 229
FEATURE                   Location/Qualifiers
source                    1..229
                          mol_type = protein
                          organism = synthetic construct
SEQUENCE: 9
KHERFIAYVG IPMLTIQARE NDAQIILGSL GSQRMKYIED ENQNYTNISS EYYSQSSMQA   60
VPMYYFNVPK GQWSVDISCE GYQPTSSTSD PHRGRSDGMI AYSNADSDYW NVGEADGVKI   120
SKLRNDNTYR QGHPELEINS CHFREGQLLE RDATISFHVE APTDGRFFLV GPAIQKTAKY   180
NYTISYGDAT DRDMELGLIT VVLDEHLEGT GSANRVRRPP REGHIYMAS              229

SEQ ID NO: 10             moltype = AA  length = 229
FEATURE                   Location/Qualifiers
source                    1..229
                          mol_type = protein
                          organism = synthetic construct
SEQUENCE: 10
KHERFIAYVG IPMLTIQARE NDDQIILGSL GSQRMKYIED ENQNYTNISS EYYSQSSMQA   60
VPMYYFNVPK GQWSVDISCE GYQPTSSTSD PHRGRSDGMI AYAAADSDYW NVGEADGVKI   120
SKLRNDNTYR QGHPELEINS CHFREGQLLE RDATISFHVE APTDGRFFLV GPAIQKTAAY   180
NYTISYGDWT DRDMELGLIT VVLDEHLEGT GSANRVRRPP REGHIYMAS              229

SEQ ID NO: 11             moltype = AA  length = 229
FEATURE                   Location/Qualifiers
source                    1..229
                          mol_type = protein
                          organism = synthetic construct
SEQUENCE: 11
```

```
KHERFIAYVG IPMLTIQARE ADDQIILGSL GSQRMKYIED ENQNYTNISS EYYSQSSMQA    60
VPMYYFNVPK GQWSVDISCE GYQPTSSTSD PHRGRSDGMI AYSNADSDYW NVGEADGVKI   120
SKLRNDNTYR QGHPELEINS CHFREGQLLE RDATISFHVE APTDGRFFLV GPAIQKTAKY   180
NYTAAYGDWT DRDMELGLIT VVLDEHLEGT GSANRVRRPP REGHIYMAS              229

SEQ ID NO: 12          moltype = AA  length = 229
FEATURE                Location/Qualifiers
source                 1..229
                       mol_type = protein
                       organism = synthetic construct
SEQUENCE: 12
KHERFIAYVG IPMLTIQARE NDDQIILGSL GSQRMKYIED ENQNYTNISS EYYSQSSMQA    60
VPMYYFNVPK GQWSVDISCE GYQPTSSTAD PHRGRSDGMI AYSNADSDYW NVGEADGVKI   120
SKLRNDNTYR QGAPALEINS CHFREGQLLE RDATISFHVE APTDGRFFLV GPAIQKTAKY   180
NYTISYGDWT DRDMELGLIT VVLDEHLEGT GSANRVRRPP REGHIYMAS              229

SEQ ID NO: 13          moltype = AA  length = 670
FEATURE                Location/Qualifiers
source                 1..670
                       mol_type = protein
                       organism = Turnip yellows virus
SEQUENCE: 13
MNTVVGRRII NGRRRPRRQT RRAQRPQPVV VVQTSRATQR RPRRRRRGNN RTGRTVPTRG    60
AGSSETFVFS KDNLAGSSSG AITFGPSLSD CPAFSNGMLK AYHEYKISMV ILEFVSEASS   120
QNSGSIAYEL DPHCKLNSLS STINKFGITK PGKRAFTASY INGTEWHDVA EDQFRILYKG   180
NGSSSIAGSF RITIKCQFHN PKYVDEEPGP SPGPSPSPQP TPQKKYRFIV YTGVPVTRIM   240
AQSTDDAISL YDMPSQRFRY IEDENMNWTN LDSRWYSQNS LKAIPMIIVP VPQGEWTVEI   300
SMEGYQPTSS TTDPNKDKQD GLIAYNDDLS EGWNVGIYNN VEITNNKADN TLKYGHPDME   360
LNGCHFNQGQ CLERDGDLTC HIKTTGDNAS FFVVGPAVQK QSKYNYAVSY GAWTDRMMEI   420
GMIAIALDEQ GSSGSVKTER PKRVGHSMAV STWETIKLPE KGNSEGYETS QRQDSKTPPT   480
ASGGSDTLDV EEGGLPLPVE EEIPDFVGDN PWSDLSTKNS QEEEAMSSES GLRPQLKPPG   540
LPKPQPIRTI RNFDPTPDLV EAWRPDVNPG YSKADVAAAT IIAGGSIKDG RSMIDKRNKA   600
VLDGRKSWGS SLASSLTGGT LKASAKSEKL AKLTTSERAR YERIKRQQGS TRASEFLESL   660
LAGEDPDSRF                                                        670

SEQ ID NO: 14          moltype = AA  length = 670
FEATURE                Location/Qualifiers
source                 1..670
                       mol_type = protein
                       organism = Turnip yellows virus
SEQUENCE: 14
MNTVVGRRII NGRRRPRRQT RRAQRPQPVV VVQTSRATQR RPRRRRRGNN RTGRTVPTRG    60
AGSSETFVFS KDNLAGSSSG AITFGPSLSD CPAFSNGMLK AYHEYKISMV ILEFVSEASS   120
QNSGSIAYEL DPHCKLNSLS STINKFGITK PGKRAFTASY INGTEWHDVA EDQFRILYKG   180
NGSSSIAGSF RITIKCQFHN PKYVDEEPGP SPGPSPSPQP TPQKKYRFIV YTGVPVTRIM   240
AQSTDDAISL YDMPSQRFRY IEDENMNWTN LDSRWYSQNS LKAIPMIIVP VPQGEWTVEI   300
SMEGYQPTSS TTDPNKDKQD GLIAYNDDLS EGWNVGIYNN VEITNNKADN TLKYGHPDME   360
LNGCHFNQGQ CLERDGDLTC HIKTTGDNAS FFVVGPAVQK QSKYNYAVSY GAWTDRMMEI   420
GMIAIALDEQ GSSGSVKTER PKRVGHSMAV STWETIKLPE KGNSEGYETS QRQDSKTPPT   480
ASGGSDTLDV EEGGLPLPVE EEIPDFVGDN PWSDLSTKNS QEEEAMSSES GLRPQLKPPG   540
LPKPQPIRTI RNFDPTPDLV EAWRPDVNPG YSKADVAAAT IIAGGSIKDG RSMIDKRNKA   600
VLDGRKSWGS SLASSLTGGT LKASAKSEKL AKLTTSERAR YERIKRQQGS TRASEFLESL   660
LAGEDPDSRF                                                        670

SEQ ID NO: 15          moltype = AA  length = 125
FEATURE                Location/Qualifiers
source                 1..125
                       mol_type = protein
                       organism = synthetic construct
SEQUENCE: 15
QVQLQESGGG LVQAGDSLRL SCAASGRSFS RYNMGWFRQA PGKEREFVAA ITWSGGTTHY    60
ADSVKGRFTI SRDNAKNTVY LQMNSLKPED TAVHYCAAGA PSTRLWHDSG SWGSWGQGTQ   120
VTVSS                                                             125

SEQ ID NO: 16          moltype = AA  length = 123
FEATURE                Location/Qualifiers
source                 1..123
                       mol_type = protein
                       organism = synthetic construct
SEQUENCE: 16
QVQLQESGGG LVQAGGSLRL SCAASGRTVN KYTMGWFRQG PGKEREFVAT ISYLGGRAAY    60
ADSVKGQFTI SRDNINNTVF LQMNSLKPED TAVYYCAATN AVLATSRSAY NYWGQGTQVT   120
VSS                                                              123

SEQ ID NO: 17          moltype = AA  length = 124
FEATURE                Location/Qualifiers
source                 1..124
                       mol_type = protein
                       organism = synthetic construct
```

```
SEQUENCE: 17
QVQLQESGGG LVQPGGSLAL SCAASGFTFS SYYMNWVRQA PGKGLEWVLS IDSDGSVKHS   60
ADSVKGRSTI SRDNAKNTMY LQMNSLKPED TAVYYCAACL GCVIESAVGE YDYWGQGTQV  120
TVSS                                                                124

SEQ ID NO: 18                moltype = AA  length = 603
FEATURE                      Location/Qualifiers
source                       1..603
                             mol_type = protein
                             organism = Cereal yellow dwarf virus RPV
SEQUENCE: 18
MSTVVLRSNG NGSRRRRQRV ARRRPAARTQ PVVVVASNGP ARRGRRRRPV GPRRGRTPRS   60
GGGSRGETFV FSKDSLAGNS SGSITFGPSL SEYPAFQNGV LKAYHEYKIT NCVLQFVSEA  120
SSTAAGSISY ELDPHCKASS LASTINKFTI TKTGARSFPA KMINGLEWHP SDEDQFRILY  180
KGNGASSVAG SFKITLRVQL QNPKXVDAEP GPSPGPSPDP PPPPSPSPEP APAKEERFIV  240
YSGVAHTIIS AQSTDDSIIV RDIPDQRFRY VENENFYWFQ IAAQWYSNTN TKAVPMFVFP  300
VPIGEWSVEI STEGYQATSS TTDPNKGRID GLIAYDNSSE GWNIGAGSNV TITNNKADNS  360
WKYGHPDLEI NSCHFNQNQV LEKDGIISFH VKATEKEANF FLVAPPVQKT SKYNYAVSYG  420
AWTDRDMEFG LITVTLDEKR GSGSPTRKSL RAGHAGVTTT TDLVALPEME NSGIETSETP  480
SAPVTSSKAP LPTVSDSESE DDPLSAAPDV GFGGTRLLID TDIKTIPDPD VADAFVNSAH  540
VGVDPWAEVR AFKRAQRPPR GPSSVASSSL SGGSLRGSLR PKTEDPKDSS KSKSRKWSLG  600
SLR                                                                603

SEQ ID NO: 19                moltype = AA  length = 246
FEATURE                      Location/Qualifiers
source                       1..246
                             mol_type = protein
                             organism = Cereal yellow dwarf virus RPV
SEQUENCE: 19
KEERFIVYSG VAHTIISAQS TDDSIIVRDI PDQRFRYVEN ENFYWFQIAA QWYSNTNTKA   60
VPMFVFPVPI GEWSVEISTE GYQATSSTTD PNKGRIDGLI AYDNSSEGWN IGAGSNVTIT  120
NNKADNSWKY GHPDLEINSC HFNQNQVLEK DGIISFHVKA TEKEANFFLV APPVQKTSKY  180
NYAVSYGAWT DRDMEFGLIT VTLDEKRGSG SPTRKSLRAG HAGVTTTTDL VALPEMENSG  240
IETSET                                                             246

SEQ ID NO: 20                moltype = AA  length = 650
FEATURE                      Location/Qualifiers
source                       1..650
                             mol_type = protein
                             organism = Barley yellow dwarf virus PAV
SEQUENCE: 20
MNSVGRRGPR RANQNGTRRR RRRTVRPVVV VQPNRAGPRR RNGRRKGRGG ANPVFRPTGG   60
TEVFVFSVDN LKANSSGAIK FGPSLSQCPA LSDGILKSYH RYKITSIRVE FKSHASATTA  120
GAIFIELDTA CKQSALASYI NSFTISRTAS KVFRAEAING KEFQESTIDQ FWMLYKANGT  180
PTDTAGQFII TMSVSLMTAK XVDSSTPEPK PAPEPTPTPQ PTPAPQPAPE PTPAPVYKRF  240
FEYIGTPTGT ISTRENSDSI SVSKLGGQSM QYIENEICET KVIDSFWSTN NNVSAQAAFV  300
YPVPEGSYSV NISCEGFQSV DHIGGNEDGY WIGLIAYSNS SGDNWGVGNY KGCSFKNFLA  360
TNTWRPGHKD LKLNDCQFTD GQIVERDAVM SFHVEATGTD ACFYLMAPKT MKTDKYNYVV  420
SYGGYTNKRM EFGTISVTCD ESDVEAERIT RHAETPIRSK HILVSEQYEQ PLPTIIDQGL  480
CDVQTPEQEQ TLVDEEDKQT VSTEPDIALM EYEAATAEIP DAEEDVLPSK EQLSFRPVDT  540
SGNKIPKPRE PEVLGTYQGQ NIYPEDVPPI ARQKLREAAN APSTLLYERT PKKSSNFLTR  600
FVEANRSPTT PAAPTVSTAS NMTREQLAEY TRIRRSLGLT AAKEYKAQFQ             650

SEQ ID NO: 21                moltype = AA  length = 234
FEATURE                      Location/Qualifiers
source                       1..234
                             mol_type = protein
                             organism = Barley yellow dwarf virus PAV
SEQUENCE: 21
KRFFEYIGTP TGTISTRENS DSISVSKLGG QSMQYIENEI CETKVIDSFW STNNNVSAQA   60
APVPVPEGS YSVNISCEGF QSVDHIGGNE DGYWIGLIAY SNSSGDNWGV GNYKGCSFKN  120
FLATNTWRPG HKDLKLNDCQ FTDGQIVERD AVMSFHVEAT GTDACFYLMA PKTMKTDKYN  180
YVVSYGGYTN KRMEFGTISV TCDESDVEAE RITRHAETPI RSKHILVSEQ YEQP        234

SEQ ID NO: 22                moltype = AA  length = 667
FEATURE                      Location/Qualifiers
source                       1..667
                             mol_type = protein
                             organism = Beet chlorosis virus
SEQUENCE: 22
MNTVVGRRTI NGRRRPRRQT RRAQRNQPVV VVQTSRRTQR RPRRRRRGNN RAGRTVSTRG   60
TGQSETFVFS EDNLAGSSSG AITFGPSLSD CPAFSNGMLK AYHEYKISMV ILEFVSEASS  120
QSSGSIAYEL DPHCKLNSLS STINKFGITK PGRRAFTASY INGTEWHDVA KDQFRILYKG  180
NGSSSIAGSF RITIKCHFHN PKXVDEEPGC GPGPSPSPQP APQKKYRFIV YTGVPVTRIM  240
AQSTDDAISL YDMPSQRFRY IEDENMNWTN LDSRWYSQNS LKAIPMVIVP VPQGEWTVEI  300
SMEGYQPTSS TTDPNKDKQD GLIAYNDDLK EGWNVGVYNN VEITNNKADN TLKYGHPDME  360
LNSCHFNQQQ CLERDGDLTC HIKTTGDNAS FFIVGPAVQK QSKYNYAVSY GAWTDRMVEI  420
GMIAIALDEQ GSSGSARTER PKRVGHSMAV STWETINLPE KEDSEKLKTG QRQDLKTPFT  480
ISGSSDVKGI EKRDLPLPAD EDIPDFIGND PWSNVSIRKL QEEEAMTSKS GLRPQLKPPG  540
```

```
LPKPQPVRTI GNFNPTPELV ESWRPDVNPG YSKEDVAAAT ILYGGSIKDG RSMIDKRDKA    600
VLDGRKHWGS SLASSLTGGT LKASAKSEKL AKLTSRERAE FERIKRQQGT TQASEYLEFI    660
LKSMNPD                                                              667

SEQ ID NO: 23              moltype = AA   length = 670
FEATURE                    Location/Qualifiers
source                     1..670
                           mol_type = protein
                           organism = Beet mild yellowing virus
SEQUENCE: 23
MNTVVGRRTI NGRRRPRRQT RRAQRSQPVV VVQASRTTQR RPRRRRRGNN RTRRTVSTRG    60
TGSSETFVFS KDNLAGSSSG AITFGPSLSD CPAFADGMLK AYHEYKISMV ILEFVSEASS    120
QNSGSIAYEL DPHCKLSALS STINKFGITK PGRRAFAASY INGADWHDVA KDQFRILYKG    180
NGSSSIAGSF RITMKCQFHN PKXVDKEPGP SPGPSPSPQP TPSKKYRFIV YTGVPVTRIM    240
AQSTDDAISL YDMPSQRFRY IEDENMNWTN LDSRWYSQNS LKAIPMIIVP VPQGEWTVEI    300
SMEGYQPTSS TTDPNKDKQD GLIAYNDDLK EGWNVGVYNN VEITNNKADN TLKYGHPDME    360
LNSCHFNQGQ CLERDGDLTC HVKTTGDNAS FFVVGPAVQK QSKYNYAVSY GAWTDRMMEI    420
GMIAIALDEQ GSSGSAKIER PKRVGHSMAV STWETINLPE KENSGEFKTD QRQDLKTPPT    480
SGGSSDMPDI VQGGLPLPIE EDIPDFIRDD PWSNIPAKTS REDEAASSKS GFKPQLKPPG    540
LPKPQPVRTI RNFDPEPDLV EAWRPDVNPG YSKEDVAAAT VMYGGSVNEG RSMIDKRDKA    600
VLDGRKSWGS SLASSLTGGT LKASAKSEKL AKLTSSERAQ FKRIKRQQGA TRASEFLEQL    660
LAGTNPDPRS                                                          670

SEQ ID NO: 24              moltype = AA   length = 723
FEATURE                    Location/Qualifiers
source                     1..723
                           mol_type = protein
                           organism = Tobacco vein distorting virus
SEQUENCE: 24
MNTGGARSNN GNGGSRVSRP RRRARSVRPV VVVAPPRGAR XRTRRRRNGG RNRRGRNGVG    60
GRSSNSETFI FNKDSIKDSS SGSITFGPSL SESVALSGGV LKAYHEYKIT MVNIRFISES    120
SSTAEGSIAY ELDPHCKLSS LQSTLRKFPV TKGGQATFRA AQINGVEWHD TTEDQFRLLY    180
KGNGTKGVAA GFFQIRYTVQ LHNPKXVDAE PGPSPGPQPQ PTPSPSPQKH ERFIAYVGIP    240
MLTIQAREND DQILLRSMGL QRMKYIEDEN QNYTNIDSQF YSQSNVNAVP MYYFNVPKGT    300
WSVDISCEGY QPTSSTTDPN RGRSDGLIAY SNSDSDYWNV GEADGVKISN LRNDNTYRXG    360
HPDLEINSCH FRDGQLLERD ATISFHVEAP DDGRFFLIGP AIQKTAKYNY TISYGEWTDR    420
DMELGLITVV LDEHLEGSGS GNLARRERRS LHQHCKSLYA PEGPPENKPW DDNQIIVGER    480
QLRKTLSMDM SEAGSDLREG KLESNPSGDA RDELNYTLNL SDSEDELIDE PNFVPGMRMN    540
LEAVPLANPA DKDYILRDRG ITTTLXEPAY MQGVAPQDKI EEDPXKHVRD FKSAHASKGP    600
ASVASGSTMR GNLRGGTLRG RSMPPPLPPP AEKVGDSLPS GKLQWDPPGS PLTPFKDKEL    660
AKPPSDARSS ISGRLTGGLL KSRVDKDLAS LTTAQRQQYE ITRQTLGKIA AKEFLQRCKE    720
GGS                                                                 723

SEQ ID NO: 25              moltype = AA   length = 667
FEATURE                    Location/Qualifiers
source                     1..667
                           mol_type = protein
                           organism = Cucurbit aphid-borne yellows virus
SEQUENCE: 25
MNTVAARNQN AGRRRRRNQR PARRDRVVVV NPIGGPPRGR RQRRNRRRPN RGGRARRGSP    60
GETFVFSKDN LTGSSTGSIT FGPSLSESPA FSSGILKAYH EYKIIMVQLE FISEASSTSS    120
GSISYELDPH CKLSSLQSTI NKFGITKSGL RRWTAKQING MEWHDATEDQ FKILYKGNGS    180
SSVAGSFRIT IKCQVQNPKY VDGSSPPPPS PSPTPPPPPP PQPQPQPCAQ RFWGYEGNPQ    240
NKILTAENSR NIDSRPLNFV QMYKWEDEKW DKVNLQAGYS RNDRRCMETY LTIPADKGKF    300
HVYLEADGEF VVKHIGDELD GSWLGNIAYD VSQRGWNVQN YKGCKITNYQ SNTVFVAGHP    360
DATMNGKSFD TARAVEVDWF ASFELECDDE EGSWAIYPPP IQKDSSYNYT VSYGNYTEKY    420
CEWGAISVSI DEDNNGNEPR RIPRRGVMAW STPEPSFSGD DSQRQDFNTP SLEERGSDAL    480
ESEEKKEEDN LLDLEEENIP DVDDDDLWKG ISRASEAGTA EDDRASTSSR LRGNLKPKGL    540
PKPQPTRTIT EFNPGPDLIE VWRPDLAPGY SKADVAAATV LAGGSVHEGR DMLERREAKV    600
MDSRKKWGIL SSTSSLTSGA LKKLSAQSEK LATLTTGERV QYQRLKNSMG STVAAEYLEK    660
VLADKTS                                                             667

SEQ ID NO: 26              moltype = AA   length = 663
FEATURE                    Location/Qualifiers
source                     1..663
                           mol_type = protein
                           organism = Melon aphid-borne yellows virus
SEQUENCE: 26
MNTVAARNQN GMGRRRRNRR RTSKSNRVVV VQTTGQPQRG RRRRRNPRRS PRGGRAGGRP    60
GETFVFSKDN LTGSSSGAIT FGPSLSESPA FSSGILKAYH EYKISMVKLE FISEASSTSS    120
GSISYELDPH CKLNALQSTV NKFGITKSGS RTWSAKLING LEWHDATEDQ FRILYKGNGS    180
SSTAGSFRIT IKCQVQNPKX VEGTSPSAPT PTPPPPAPSP EPTPCKGARF WGYEGNPQSK    240
IQTAENNRNI DSRPLNYVSM YRWEDEKWDQ VNLQAGYSRN DRRCMETYFV IPANKGKFHV    300
YLEADGEFVV KHIGGDLDGS WLGNIAYDVS QRGWNIGNYK GCSIKNYQSK TTFVAGHPDA    360
SMNGKNFDAA RAVEVDWFAS FELECDDDEG SWRIYPPPIQ KDSSYNYTVS YGNYTEKYCE    420
WGAVSISIDE DNATGRVPQK IKPRKGVMTW STPEPERQPV EQTPVQEPSE TSGLDAPPTT    480
KQEDETTDDL GGRFKEPQIP EFSTPMHMLA RDLGGLTESS SRAPEGVASW VQLEADPVNE    540
SEYSSDNETI ASPPTTTVSS PFTSIPNTER VLQMPGVYQG DRQIASSVLD EHRKRSFAKR    600
LLPSLGGSRA SALSGGTLRQ KHSDLIKQYM TAAEHAEAQR IRNQLGKGAQ TRYIESLNLH    660
```

-continued

```
DRV                                                            663

SEQ ID NO: 27          moltype = AA  length = 736
FEATURE                Location/Qualifiers
source                 1..736
                       mol_type = protein
                       organism = Pepper vein yellows virus
SEQUENCE: 27
MNTGGVRRNN NGNGGSRNTR RRRRPRQVRP VVVVAPPGRT RRGNRRRRNG GRNRRSRNRV   60
GGRSSNSETF IFNKDSIKDS SSGSVTFGPS LSESVALSGG VLKAYHEYKI TMVNIRFVSE  120
SSSTAEGSIA YELDPHCKLT SLQSTLRKFP VTKGGQATFR ASQINGVEWH DTSEDQFRLL  180
YRGNGTKNVA AGFFQIRFTV QLHNPKXVEG STPPPPPPSG PEPPPPPPQP EPCKKNRFWG  240
YEGNPQSKIL TAENDRNIDS RPLNFVSMYK WEDEKWDKVN LQAGYSRNDR RCMETYLTIP  300
ADKGKFHVYL EADGEFVVKH IGGDLDGSWL GNIAYDVSQR GWTVGNYKGC KIKNYQTNIT  360
FVAGHPEAKM NGKAFDSARA VEVDWFASFE LECDDEEGSW MIYPPPIQKD SSYNYTVSYG  420
NYTEKYCEWG AISVSIDEDN EGYAPRRIPR KGEMAWSYPE KDYSENKPQK ENWDTEPLDT  480
GEMQRERQLV KTPSPDVSDS GSEFGADPIP QDLIDKVNRG EALDPMQQLE YDKYRFQENV  540
IELSESQDQS SEYPKLPPPV PHKPLPLGRT EKFFRPRADL LEAWDKDHFD PGYTKEEVAA  600
ATIISHGSIT DGRAAIEERD NKIQRARVSW PHDKSTTSPS IAKLREETSE KKALFGGSLR  660
RGSEAASSLG GGSITGGTLK SKRTVEEGIV PKLTTTQRLR YEQLKARSQT AANEYLWSVE  720
IPPEKPPGPS TFKGRS                                                 736

SEQ ID NO: 28          moltype = AA  length = 731
FEATURE                Location/Qualifiers
source                 1..731
                       mol_type = protein
                       organism = Pepper vein yellows virus 5
SEQUENCE: 28
MNTGGVRSDN NGNGGSRNTR RRRRPRQVRP VVVVAPPGRA RRGNRRRRNG GRNRRSRDRV   60
GGRSSNSETF VFNKDSIKDS SSGAVTFGPS LSESIALSGG VLKAYHEYKI TMVNIRFVSE  120
SSSTAEGSIA YELDPHCKLT SLQSTLRKFP VTKGGQATFR ASQINGVEWH DTSEDQFRLL  180
YKGNGTKNVA AGFFQIRFTV QLHNPKXVEG STPPPPPPSP GPEPPPPSPQ PEPCKKSRFW  240
GYEGNPQSKI LTAENDRNID SRPLNFVSMY KWEDEKWDKV NLQAGYSRND RRCMETYLTI  300
PADKGKFHVY LEADGEFVVK HIGGDLDGSW LGNIAYDVSQ RGWTVGNYKG CKIKNYQTNI  360
TFVAGHPEAK MNGKAFDSAR AVEVDWFASF ELECDDEEGS WMIYPPPIQK DSSYNYTVSY  420
GNYTEKYCEW GAISVSIDED NEGYVPRRIP RKGEMAWSHP EKDYSENKPQ KENWNIEPLD  480
AGETQRERQL VKTPSPDVSD AGSDIDDDLI PVDLIERVKR GEKLDPMEQL EYDRHYRSR  540
DVEPEDSTVD DTSSYPRITP REPVEQLPAG RTTSDFAPKA ELLEAWDNKH FNPGYSEAEV  600
AAAATIIKAGS IMEGRSMIRE RDKKILRAAT SWKPEEKPES PSIAKLRSSK LTGGSLRANS  660
ETASSIGGGS LSGGSLKPKR TIEQGIVEMM TTAQRLEYER LKTINTGKAN EFLWSIGKPP  720
PPNPDPFNRR I                                                     731

SEQ ID NO: 29          moltype = AA  length = 657
FEATURE                Location/Qualifiers
source                 1..657
                       mol_type = protein
                       organism = BARLEY VIRUS G
SEQUENCE: 29
MNTGGRNGRR TRSRRRVRPA SRTQPVVVVA AGQRRRRPRR RGRRTGNTSG GSGIRRGSRE   60
TFVFSKDSLT GNASGKLTFG ASLSECAAFS SGILKAYHEY KISKVTLEFI SEASSQSEGS  120
IAYELDPHNK LSALSSTINK FSIVKGGKRT FTSNQIGGGV WRDSTEDQFA ILYKGNGKSS  180
IAGSFRVTMD VLTQNPKXVD GASPQPAPAP TPAPTPPPTP APATQPKFYN YSGVPESRIQ  240
SRKNSEFIDI YSLSFIKMYY WHDESWSSET LSAGYVQNDS SRATPYFLIP THVGSYKVYI  300
ECEGFQAVKA KGGANNGKMS GFITYDPKQS GWQAYSWSGC TFSNYKVTDG CVEAHPDMKV  360
NGCSFSKGQC VEKDVVLSFD LTVSEEGYWA LQAPPIEKSD DHNFIVSYGS YTEKILEWGM  420
VSISIDEINN NDAHRVPKRN KDARELRRLT DFTNSDSVGV LVKDKDLNSE PDGQLVVQTP  480
AQPETGGELT VQNPPPKPAL QVSTRVQQWL DDSEPESDAD APPPPAPGPT QVRLPTLNER  540
NLKPSPPRSP RRDMNVTYED DVASRTSRTP TITGGNLRPK LKSVSDDVET QSVTPSRTGS  600
LTGGSLRPSL QGGRLGQQQF RMTAEQARQY DMIKRSFGKT RANEYYEELK KAAGSSS     657

SEQ ID NO: 30          moltype = AA  length = 700
FEATURE                Location/Qualifiers
source                 1..700
                       mol_type = protein
                       organism = Carrot red leaf virus
SEQUENCE: 30
MATYGLTKRA TGIKPMVVVN TPSRRPRRRT RTKPIVVVQT ARTGRRRRRR RGRGSGNPRT   60
MGGSGGGISS QKFVFSKDNI AGSSGGVLTF GKDLSDHPAF SNGLLKAFHQ YKITNMRVRY  120
ISEAPSTAGG SISYELDPSC ELDKLSSTIY KFGVLKNGQA SWSSAEKINGK EWHSSSENQF  180
RFLWKGNGSN STVGSFEIHY TCLFQNPKXV DAEPGPSPGP SPPPLPTPTP EPTPKQHERF  240
IVYVGSPTMD IQARENDDII TLTEPGPQNW RRIQDEDMNE VSLDSRFWTN SDLKAKPMFY  300
FPVPAGSWSV DITCEGYQPT SDPTKQGDNR SDGLIAYSAD NNDNLWNVGQ TGSLKISNLR  360
GINTFKAGHP KLVVNGCNFN DGQVMERDGT LSFHVQTEKD GSFFLTGPPV QKQGRYNYTV  420
SYGEWTKRIL EFGLITVVLD EHLDNSGSNK FKRPPRNGHQ WAGLVTDTVM ENTVSDKTPD  480
PPKSKRKLEP EKANSDNKLP EPQKRKLVID PKLDEVEVES IPDAPEDFNW ATLGIPRGKG  540
PASLAGFNDT ELARGKDQSS DDELPSHFSA PGLDEIPAKP QPVDLSQTSF DYGTHIPNTD  600
DLGMFDRPGD KPVVSGILDK QRVKSFGKRL LPALSGSTTS SLQGGTLRQK YSDATRKYMS  660
SEEVVKANKI RTSLGKTALA NYLKSLNLHE RVGSSPSQEQ                       700
```

-continued

```
SEQ ID NO: 31          moltype = AA  length = 686
FEATURE                Location/Qualifiers
source                 1..686
                       mol_type = protein
                       organism = Chickpea chlorotic stunt virus
SEQUENCE: 31
MNTVVVRNNG RRRRNRRTVQ RARRRNPVVV VEAPRQPQRG RRRRRNRRRA SGRSTAGRRG   60
SSETFVFSKD NLAGSSSGSI TFGPSLSDCP AFSSGILRAY HEYKISMVKL EFISEAASTS  120
SGSIAYELDP HCKSTSLGSY INKFGITSNG QRTFAARLIN GIEWHSSDED QPRILYKGNG  180
GSAIAGSFRI TIKCQTQNPK XVDDSSPPGP SPTPPPPPPA PAPEPQPCKK YRFWGYEGVP  240
QNKIVTAQND RNIDVRGLNY VKFYKWEDDN WTEVNLQANY SVNNSQYAEP YMIIPASKGK  300
FHVYLECDGQ MAVKSVGGKA DNSWRGLIAY DTSRRMWNVG NYKGCTIENY RKTDSFVLGH  360
PDVEVNDCKF DKARGVEADW YASFQLTCDD DEGSWILYAP PIPKDSLYNY TVSYGEYTEN  420
MCEWGAVSIS IDEDNSSTGN EVKIKPGRGH LVHRALPEGT LEQQPLEDVQ VKEYFWKENQ  480
SETTSDSDGE SFISKIKGKL PMTTKLPPKG FLSRLKPSEK EETARSKESE VKPEDVDNLV  540
RAAGKEFQYG IYDDARERLH NKEFNQNMEE LESDLEEINR LEPPDIDVWR GKDTAETVAV  600
FEDPWEFFRK QEDPNPPKLK GTLSKIGSSI GGGSLSGGNL RRAAESVNED SMKFKLSTTE  660
RNQYERIRKS KGETAARVYL RSRFSS                                       686

SEQ ID NO: 32          moltype = AA  length = 672
FEATURE                Location/Qualifiers
source                 1..672
                       mol_type = protein
                       organism = Ixeridium yellow mottle virus 2
SEQUENCE: 32
MNTGAGRNVG RRRRRRTNTI PRRRNRVVVV QASRQPQRGA RRRRVRRRPA GGSGVGVRRS   60
RETFVFTKDS IAGSASGSIT FGPSLSESPA FSSGILRAYH EYKITMVKLE FISEASSTSS  120
GSISYELDPH CKSSSLQSTV NKFGITKNGA KTWTARLING QEWHDATEDQ FRILYKGNGA  180
SSVAGSFRIT ITCQLQNPKX VDGTSPPAPA PPQPPPPPSP PPPPPPEPTP CKGARFWGYE  240
GNPQSKIITA ENDRNIDSQP LHFVYMWRWE DEKWEKVTMQ AGYSRNDRRC MEPYFVIPAN  300
KGKFRIYLEA DGEFVVKHIG GGYEGNWLGN IAYDVTQRGW NIGEYKGCKI SNYQAQLTYV  360
PGHPDARMNA KQFDSNRVIQ VDWFASFEME CDDDEGSWRI YPPPIQKDSS YNYTVSYGNY  420
TEKYCEWGTV SISIDEENPK GKAPKFKPRK GAMTPATPLA LNDLPEDLSQ RPDYNTPPTG  480
SSVELERSRS EKPLKHLDLR SLDSEPINLL ARDLRGLDDN SSDGEEKKPN DVSSWLENTD  540
AFEEVVENEP DWNSEPVARP PSPTETQTLT SVPNTEQVMR MPGVYDPSDR PHARAVLDEK  600
HSKSFAKRLL PSLGGSRTSA LQGGALRQKH SDTIRRYMTT AEQREANRRK QQLGETAMKQ  660
YIEGLNLHER VQ                                                      672

SEQ ID NO: 33          moltype = AA  length = 683
FEATURE                Location/Qualifiers
source                 1..683
                       mol_type = protein
                       organism = Pepo aphid-borne yellows virus
SEQUENCE: 33
MNTVAVRSSN GTRRRRRPRR SARRVRVAMV QAIGPAQRGG RRRRNRRRVN RGGRARGGRQ   60
GETFVFSKDN LSGSSSGSIT FGPSLSESPA FSSGILKAYH EYKITMVKLE FISEASSTSS  120
GSISYELDPH CKLSSLQSTV NKFGITKNGS RSWTAKFING LEWHDATEDQ FRILYKGNGS  180
SSVAGSFKIT IQCQVQNPKX VDGSSPDPPP PPPQPAPKGA RFWGYEGNPQ CKIITAENDR  240
NIDVKSLYSV SMYKWENEKW DTINLQANYS RNDRRCAEPY MVVPADKGKF HVYIECDGEF  300
VVKHIGGDID GSWLGNIAYD RSQRSWTVGE YKGCKIENFQ NNTTFVPGHP DATMNGKHFD  360
TARVVEVDWF ASFHLICDDD EGGWLLYPPP IQKDSSYNYT VSYGNYTEKY CEWGAISVSI  420
DEDDENGNVP NRRIPRRDSI QGKENPLPAE TGQRQDLNTP SEKVPDAGSG EHEEKENSSL  480
AETGQRQDLN TPSQEVLDPG SSKESEPGHF EGSSLPPDDG DAPEYIGEDP WEGITVDLPK  540
DDEATTTASR LKGNLRPPGL PKPQPTRTIR NFDPNPDLIA AWNPGVSDPG YTAEDVAAAT  600
VLAGGSISDG RSILKKRDER ILNSRDKWSF TSALTGGTLR ASQKSEKLAK LTTAERQQYE  660
KLKRQSGSTV AAEYLESIIK FRG                                          683

SEQ ID NO: 34          moltype = AA  length = 668
FEATURE                Location/Qualifiers
source                 1..668
                       mol_type = protein
                       organism = STRAWBERRY POLEROVIRUS 1
SEQUENCE: 34
MARRPRGSRG GKGKKKQNAG RRNPSRMARP AQPIYVVQRP PNQGTGRRGR RNRNRRLRAQ   60
GYGLGGKHET LKFTKEDIKR NSSGYITFGP SLSEHPAFSN GNLKAYKHYR ITRINVEYLS  120
ESTDQAPGAI KFEMDTSLSA TKVTSPIHRF PIKKNGRYTW TAPHINGQLT RETTSDQCRF  180
LYEATTTSTE PAGVFNFTYD VHLMDNKYVE GASPSPSPPP PGPAPPPPPP PPPAPPPEPT  240
PAKRFWGYDG TPVSKISTAR NDQNIDVKSL NSIRLWKWEN ESWTDTVLTA NYSKNDRVEA  300
IPYFLVPVAK GTHRVYIECE GDYGVKSIGG KADGCWGGII CFDSKKDGWM ARPYSSCKMT  360
NYKARTTFVC GHPDAELNGC KFPKERGVES DCQISFHLEV EDDGYFAMQP PPIQKSHEYN  420
YDTSYAAYTD KNMEWGSISI SIDEVDTARP EYESTFRNKP EKPNSITRWI SQLNVEKLVV  480
GAETTAEETN QQSDQIPVGT YRKRASDDDY PLLYEYDDNP PDSEIENWEF VTPTPIAPDL  540
PRPVPRTETR FAPKATLLRK VDPEHFDTNP SIDEAERLAE FHRFTPAQNR EAAEQMEVKT  600
QNKRETWAPS VAGSTSSRFT GNLRGRFASR PDPRLAQLTT EQRRAYESER NSLGSQAAKI  660
WLDNLFKS                                                           668

SEQ ID NO: 35          moltype = AA  length = 665
FEATURE                Location/Qualifiers
source                 1..665
```

-continued

```
                        mol_type = protein
                        organism = Suakwa aphid-borne yellows virus
SEQUENCE: 35
MNTVVVRNRN GMGRRRRNSR RNAKGNRVVV VQAPGAPQRG RRRRRNGRRP SRGGRARGTS    60
QGETFVFSKD NLTGSSSGAI TFGPSLSDSP AFSSGILKAY HEYKISMVKL EFISEASSTS   120
SGSISYELDP HCKLSSLQST VNKFGITKSG SRTWSAKFIN GMEWHDATED QFRILYKGNG   180
SSSTAGSFRI TIRCQVQNPK XVDGASPPPA PTPPPPPPGP PPEPTPCKGA RFWGYEGNPQ   240
SKIQTAQNYR NIDFRPLNYV SMYRWEDEKW DKVELQAGYS RNDRRCMETY FEVPASKGKF   300
HVYLEADGEF VVKHIGGDLD GSWLGNIAYD VSQRGWNVGN HKGCNIKNYQ SNTSFVAGHP   360
DATMNGKQFD KARAVEVDWY ASFELECDDD GGSWRIYPPP IQKDSSYNYT VSYGNYTDKY   420
CEWGAVSISI DEDNPTGRAP QSIKPRKGVM TWSMPEPERQ LAEQTPAEEP SETSGLGGPP   480
LIKFGEDSTG SQGDHITKSQ IPEASTPMHQ IVRDLGGLTD STNRAPRGVA EWIQVDADPV   540
NEEEYSSDGM ECASPPSPTR TSILTSIPNT ETVLGLPGVY PSDREVASSL LNDKRVKSFG   600
KHLLPSLGGS RTSALSGGTL RQKHSDLIKS KMTTAEQAQA QKIRRELGKG AQTRYIESLN   660
LHDRV                                                              665

SEQ ID NO: 36            moltype = AA  length = 704
FEATURE                  Location/Qualifiers
source                   1..704
                         mol_type = protein
                         organism = WHITE CLOVER MOTTLE VIRUS
SEQUENCE: 36
MNTVVVRNNG RRRRNRRPIR RAQRRNPVVV VQPARQPQRR RRRRRNRRRA ARGSTAGRRG    60
SSETFIFSKD NLKGSDSGRI TFGPSLSDCP AFSSGILKAY HEYKITMVKL EFISEAASTS   120
SGSIAYELDP HCKASELGSY INKFGITKSG QRTFSARFIN GIEWHSSDED QFRILYKGNG   180
NSAIAGSFRI TIKCQTQNAK XVDDSSPPGP APTPPPPPPP APSPEPQPCK KFRFWGYEGV   240
PQNKIITAQN NRNIDVRALN YVKFWKWEDD NWSEVNMQAN YSTNNSQYAE PYMVIPASKG   300
KPHVYLECDG QMAVKSVGGK ADNTWRGLIA YDTSRRMWNV GNYKGCVIEN YKMSSTFVNG   360
HPDVELNDCK FDKARGVEAD WYASFQLTCD DDEGSWLLYA PPIPKDSLYN YTVSYGEYTE   420
NMCEWGAVSI SIDEDNGSTG NEVSDYCRRG YMRQSLPEGK LEQQPYVEDV DKINSWKENQ   480
SETSSDSEDV AFANKMRGKL PNQTKLPPKG FLSRLKPSEK EEIVQAKPTQ VTDDDVLRGM   540
KAVGVFANPS YVHPVREKLE DIERQELMKE LEKDLQEINR LEPPDEISAE ENIPDFVEPV   600
LPVPDPDWFN EHTAKTISVI EHPWDFPPIE DTSKKKLRGT LSQAGGSISG KSSLGGGTLR   660
RSTEDVWRET LKSKLSTSDR NRYERIVKGQ GKTVADQFLR DRAA                    704

SEQ ID NO: 37            moltype = AA  length = 646
FEATURE                  Location/Qualifiers
source                   1..646
                         mol_type = protein
                         organism = Maize yellow dwarf virus RMV
SEQUENCE: 37
MNLGGRRNGR RGTRLRRRVR IARTTQPMVV VAQTQRRRRI RRRGRPSGDT SGGPRGRGGS    60
RETFVFSKDS IAGSASGKLT FGASLSECAA FSGGILKAYH EYKITKVILE FISEAPYTAA   120
GSIAYELDPH NKLSTLASTI NKFSIVKGGK RAYTSKQIGG GVWRDSSEDQ FAILYKGSGN   180
SSVAGSFRIT MEVHTQNPKX VDGASPAPDP TPTPTPTPTP TPTPTPTPVT QEAFYGYSGV   240
PECKIQSRKN SEFIDIYSLN FVKLFYWRDE AWSSETLSAG YIQNDSLRAT PYLLVPTKKG   300
KYSVYIECEG FQAVKAKGGN NDGKMSGFVT YDKDQSGWQV YSWAGCSLSQ IKVKDTGVVA   360
HPDMKVNGCS FTKGQLIERD FICSFHLEAT EDGYWALQAP PVEKSDDHNF IVSYGSYTEK   420
ILEWGSVSIS IDEINRTEAR KIPKRDKDLS QSGRLADMTN VPTVGVVVAA TTKPDLPVEQ   480
PNQLAVVEQP TEEQQKKRAT IDQWLDAVEA LAPPEPEGLV TQVRLPTAAE RGLTSQKLPL   540
HQRGTFKDLA NRDADTYSVA SRGLTGGLRG TPATPQVETI EENPVQVDDD SKSLVSSSSR   600
LTGGLRLRTS YRMTTQEAKQ YDEIRRSFGK ARAKAYYDDL CKANWY                  646

SEQ ID NO: 38            moltype = AA  length = 612
FEATURE                  Location/Qualifiers
source                   1..612
                         mol_type = protein
                         organism = Cereal yellow dwarf virus RPS
SEQUENCE: 38
MSTVVLRSNG NGSRRRRQRV ARRRPAVRTQ PVVVVTPNGP ARRGRRRGPA RPRRRRTPGL    60
GGGGRGETFV FTKDSLAGNS SGSITFGPSL SDYPAFQNGV LKAYHEYKIT GCILQFVSEA   120
SSTAAGSIAY ELDPHCKISS LASTNNKFTI TKTGARSFPA KMINGLEWHP SDEDQFRILY   180
KGNGASSVAG SFKITLRVQL QNPKXVDAEP GPSPGPSPDP PPPSPSPEPA PAKEERFIVY   240
SGVAHTVITA QGTDDSIIVK DIPDQRFRYV ENENFYWFQI AAQWYSNTNT KAVPMFVFPV   300
PIGEWSVEIS TEGYQATSSM TDPNKGRIDG LIAYDNSNEG WNIGAGSNVT ITNNKADNSW   360
KYGHPDLEIN SCHFNQNQVL EKDGLISFHI KATEKEANFF LVAPPVQKTS KYNYAVSYGA   420
WTDRDMEFGL ISVTLDEKRS SGSPTRKSLR AGHTQVASTT DLVASPEKDN SGIQTSETPA   480
VPVTSSKAPI PMVSDSESED DPLSAAPDVG FGGTRLLLDT DIQTVPNPEV AEAFLNSAHV   540
GYDPWAEIRA FKNAQKPVRG PSSVASGSIT GGSLRGTLRP ASEPARETPY ERDENKTTRR   600
QKSRFSFGGG RS                                                      612

SEQ ID NO: 39            moltype = AA  length = 643
FEATURE                  Location/Qualifiers
source                   1..643
                         mol_type = protein
                         organism = WHEAT YELLOW DWARF VIRUS GPV
SEQUENCE: 39
MSTVALRNGN GPRRRRVSRR RVVARTQPMV MVATNGQPRR RRRRRPAGRG RRRVPRSTGG    60
SHGETFVFAK DSLKGNSSGS LTFGPSLSEY PAFKDGILKA YHEYKITNCV LQFITEASST   120
```

-continued

```
AAGSISYELG PHCKSSSLTS TINKFSITKT GARSFPAKMI NGLEWVANDT DQFRILYKGN   180
GDANTAGSFR ITMKVLFQNP KXVDAEPGPS PGPSPTPPPP PPEPTPPVEE RFIVYTGVAH   240
TTILAQSTDD AISLRNIPDQ RFRYIENENF YWFNIEAQWY SNTNIKAVPM FYFPIPEGQW   300
SVEISTEGYQ ATSSTTDPNK GRVDGLMAYD DSSEGWNIGI GNNVEITNNK ADNTWKYGHP   360
NLEINSCHFK QQQCLERDGV ISCHVKTIGP SATIFVVAPP VQKLSKYNYA VSYGAWTERD   420
MEIGLITVTL DEKRDSGSAR KKILRSGLPE ATNFTLAAHP EKENFGIQTS ESPLAPAISP   480
KAQLLTLSDS DSEDDPLSAS PDVGFGGTRL LVDTDIKTIP DPSVAEAFVN SAHVGEDPWA   540
DVRAFKSAQR PPRGPSSVAS GSISGGSLRG TLRPASKPAR ETPYERDENK TTRRQKSRFS   600
FGGGRSLKSH RAETVNLPKQ AKENALDHPS HDVKRRIKTL PPS                     643

SEQ ID NO: 40           moltype = AA  length = 669
FEATURE                 Location/Qualifiers
source                  1..669
                        mol_type = protein
                        organism = COWPEA POLEROVIRUS 1

SEQUENCE: 40
MNTVVVKRRN GGPNRRRNRR AARSNTMVMV QAPRPTGRGG RRRRNRRRPN RGGRNRGGSG   60
ETFVFSKDNL SGSSSGAITF GPSLSDCPAF SSGILKAYHE YKISMVKVEF ISEAASTSSG   120
SIAYELDPHC KSTSLQSYVN KFGITRNGQR TWTGRLINGV EWHDTTEDQF RILYKGNGSS   180
AIAGSFRITI KCQTQNPKXV DDSSPPPAPA PQPTPPSPTP EPKPCKKDRF WGYEGVPQSK   240
ITAARNDQFI DVKPLNYVQM YKWEDDKWDR INMQASYARN DKSYAEPYMV IPANKGKFHV   300
YVECNGMMAV KSIGGKSPDS WNGLIAYDTH RKAWDVGNYK GCVIENYQKN NTFVAGHPDV   360
ELNNCKFESD RGVECDCYLS FQLTCDDEDG AWCLYAPPIP KDDRFNYTVS YGAYTERNCE   420
WASVSISIDE DNGTGNEVKR KPRGGNYDWA SPGVLPTEDY NDRGRPEGKQ VMDQSIHGQT   480
FSEISGPGEG SKSQGVTDDA MSDISGQLVP VLTTSPLAGF EEYSPPASPP PPFELPVPAL   540
EWKPPSPPSS PPMTRNRTGL FKGLRAKIKQ NKADLAETAS RVSRGEEFAD TPANIDSRFR   600
ELQASNTAAN LPSYEPRERD VWEGVRFANQ RAQDTDTRSR TSTLQGGTLR GGILRSPKQQ   660
RFGRMEDVD                                                          669

SEQ ID NO: 41           moltype = AA  length = 699
FEATURE                 Location/Qualifiers
source                  1..699
                        mol_type = protein
                        organism = COWPEA POLEROVIRUS 2

SEQUENCE: 41
MNSAGVRNSN GRRTRRGRRI QRRQRVVVVQ ASGLPRRRRR QRRNRRAPAR GGGPGRGSSD   60
TFVFSPDSIK GSDSGYFTFG PSLSAKPEFC NGILRAYHEY KITMVKLEFI SEASSTSSGS   120
IAFELDPHCK YSSVQSSINK FGIVKGGNRT WNARQINGLE WHDATEDQFR ILYKGNGGSA   180
VAGAFRITFR CQFQNPKXVD GSSPPPPPTP QPGPSPPPPD PQPCKKFRFW GYEGVPQNKI   240
ITAENDRNID VRGLNFVKFD KWEDDNWTSV DLQAGYSVNN SQYAEPYMVV PATKGKFHVY   300
IEASGLMSVK SVGGKADNSC RGFIAYDTSR RAWNIGNWKG CVFESYKSKT QFVLGHPDLV   360
INNCKFDKAR GMEADWYASF QLSCDDDDGA WVLYAPPIPK DSLYNYTVSY GEYTENMCEW   420
GTVSISIDED NQQGNNALKP QKGEMLWSTP EKELPGGQRQ DSKTPAIKVV PVTGQDQAPI   480
PTKPFKFVGH TALQNAAYEA VEDLGLPIKP TINEFGRIGD GYSIEVPEYV PPKQYIQYCN   540
DQITARKFQD ADDAEAMRLK TLDDFRSCGD SRVQNLSRES EIAEIDAIYA RRVQSQETDK   600
MNLSFTPDWG DYDFKRDRTP SPDRSSQKPN LKGKMRGVLK RTSDQASSTV SSLTGSLRPR   660
RLDPRLERLT TAQRFSYENM LRVNKDQAAR FLDREFGPL                          699

SEQ ID NO: 42           moltype = AA  length = 674
FEATURE                 Location/Qualifiers
source                  1..674
                        mol_type = protein
                        organism = WHEAT LEAF YELLOWING-ASSOCIATED VIRUS SEQUENCE: 42
MNTGGNRTRR NARRRANRRR STRPVVVVRP TPKPRRVRRR RASAGGGAVR GPGGRSNREV   60
FTFTVDDLKA NSSGILKFGP NLSQYAAFNN GILKAYHEYK ITSLTIQYNS CSSSTTSGAI   120
ALEVDTSCSQ TTTGSKIVSF PVKSNTRKTF PTSFIRGKDF VTTTADQFWL LYKGNGDSSL   180
AGQFVCRFEC QFQNPKXVDG ASPQPEPTPT PAPTPPPKKN AFFGYEGVPT SIVKTRRNDE   240
YMDVGSLSSV KLYFWKDESW SIEYLSANYS QNDSNRATPY FLIPVSEGKY SVYIECEGFQ   300
AVKAKDGPND GKMSGFITYS EGQNGWMARA YTGCTISNYR ATDSKVAGHP DLEVNGCNVT   360
DQLVERDFYC SFHLDATGDG YFALQAPPIE KSDHHNFVVS YGNFTNKTLE WGSVSISIDE   420
VNTTEAHQRS NRDKTAGGNS RLGAVLDLGT YESTIDKPAP RATESTEPKP SPALAPRAAA   480
PEPQLKISDK PDPKIQNWLN SLEDESVVDE VLNETVYAPP KPPSLKPTSE DTLRQADKVR   540
RALMANASQN SPPKDHLVNV ETSSTFGGSL QGGSLHGGSL QGGSLRGGSL GGRSSRPPLP   600
TIASPPRGRS VSPPASMAST LRGGSLSGGS LRGGNINVRR EMTREESREY TRLRNSMGKT   660
AARNYADSIN AKYP                                                     674

SEQ ID NO: 43           moltype = AA  length = 658
FEATURE                 Location/Qualifiers
source                  1..658
                        mol_type = protein
                        organism = BARLEY YELLOW DWARF VIRUS GAV SEQUENCE: 43
MNSVGRRNNR RRNGPRRARR AGAVRRMVVV QPNRAGPKRR TRRRTRGGGA NLISGPAGRT   60
EVFVFSVNDL KANSSGTIKF GPDLSQCPAL SGGILKSYHR YKITNVKVEF KSHASASTVG   120
AMFIELDTSC SQSTLGSYIN SFTLSKSATK NFTAQQIDGK EFRESSVNQF YMLYKANGST   180
SDTAGQFIIT IRVANMTPKX VDSSTPEPTP QPQPEPKPDP QPTPEPQHKR FFEYVGTPYV   240
IIQTRESSDS IAVKSMNDQS FQYIENETSE QRTVQAWRTS NNGVQAQAAF VFPIPAGEYS   300
VNISCEGLQS VDHIGGNRDG YWIGLIAYQN QSGDYWGVGN YAGCDITNLL GTNTWRPGHE   360
```

-continued

```
DLELDGCKFT NGQIVERDAV ISFHVKAQGA DPKFYLMAPK TMKSDKYNYV VSYGGYTDKR   420
MEFGSISVTV DESDVEAQRY NRHTSTVGKA ENRDYGWMSV LPPYDPNQVP EQEEEQPMVD   480
KEMDSRPPVE PPSPTSDTEA ERAFDLREEE LTRARLEYEA ATESIPDAAP DVLPSKSEMS   540
SRPIDHDGRS LPKPQSKEVL GTYQGQNITP DDVPPVIAEK LREVNRAPST LLYDRQPKTP   600
KSFLSRFVET NKTSLASPGS QSSTSGMTRE QASEYTRIRK SMGLTAAKEY KASLADTW     658

SEQ ID NO: 44          moltype = AA  length = 657
FEATURE                Location/Qualifiers
source                 1..657
                       mol_type = protein
                       organism = Barley yellow dwarf virus MAV
SEQUENCE: 44
MNSVGRRNNR RRNGPRRARR VSAVRRMVVV QPNRAGPKRR ARRRTRGGGA NLISGPAGRT   60
EVFVFSVNDL KANSSGTIKF GPDLSQCPAL SGGILKSYHL YKITNVKVEF KSHASASTVG   120
AMFIELDTWC SQSTLGSYIN SFTISKSATK TFTAQQIDGK EFRESTVNQF YMLYKANGST   180
SDTAGQFIIT IRVANMTPKX VDSSTPEPSP QPQPEPKPDP QPTPEPRQKR FFEYVGTPYV   240
VIQTRESSDS IAVKAMNDQS FQYIENETSE QRTVKAWWNS NNSVQAQAAF IFPIPAGEYS   300
VNISCEGLQS VDHIGGNRDG YWIGLIAYQS QSGDYWGVGN YVGCDITNLL GTNTWRPGHE   360
DLELNSCKFT DGQIVERDAV ISFHVKARGA DPKFYLMAPK TMKADKYNYV VSYGGYTDKR   420
MEFGTISVTV DESDVEAERY SRHTSTVRRT ENRDYGWMNV LPPYNPDQVP EQEDEQPVVD   480
KEMDAGSPID TASLTSDTEA EKAFDLKEEE LTRAILEYEA ATVSIPDAAP DILPSKSEMS   540
SKPIDRDGRS LPKSQTKEVL GTYQGQNITS DDVPPVIAEK LREVNRAPST LLYDRQPKQP   600
KNPLTRFVLS NKTSTASPGS QSSTAGMTRE QASEYTRIRK SLGLTAAKQY KASLDDT      657

SEQ ID NO: 45          moltype = AA  length = 651
FEATURE                Location/Qualifiers
source                 1..651
                       mol_type = protein
                       organism = Barley yellow dwarf virus PAV
SEQUENCE: 45
MNSVGRRGPR RANQNGTRRR RRRTVRPVVV VQPNRAGPRR RNGRRKGRGG ANFVFRPTGG   60
TEVFVFSVDN LKANSSGAIK FGPSLSQCPA LSDGILKSYH RYKITSIRVE FKSHASANTA   120
GAIFIELDTA CKQSALGSYI NSFTISKTAS KTFRSEAING KEFQESTIDQ FWMLYKANGT   180
TTDTAGQFII TMSVSLMTAK XVDSSTPEPK PAPEPTPTPQ PTPAPQPTPE PTPAPVPKRF   240
FEYIGTPTGT ISTRENTDSI SVSKLGGQSM QYIENEKCET KVIDSFWSTN NNVSAQAAFV   300
YPVPEGSYSV NISCEGFQSV DHIGGNEDGY WIGLIAYSNS SGDNWGVGNY KGCSFKNFLA   360
TNTWRPGHKD LKLTDCQFTD GQIVERDAVM SFHVEATGKD ASFYLMAPKT MKTDKYNYVV   420
SYGGYTNKRM EFGTISVTCD ESDVEAERIT RHAETPIRSK HILVSERYAE PLPTIVNQGL   480
CDVKTPEQEQ TLVDEDDRQT VSTESDIALL EYEAATAEIP DAEEDVLPSK EQLSSKPMDT   540
SGNIIPKPKE PEVLGTYQGQ NIYPEDVPPM ARQKLREAAN APSTLLYERR TPKKSGNFLS   600
RLVEANRSPT TPTAPSVSTT SNMTREQLRE YTRIRNSSGI TAAKAYKAQF Q            651

SEQ ID NO: 46          moltype = AA  length = 650
FEATURE                Location/Qualifiers
source                 1..650
                       mol_type = protein
                       organism = Barley yellow dwarf virus PAS
SEQUENCE: 46
MNSVGRRGPR RANQNGPRRR SRRTIRPVVV VQPNRAGPRR RNGRRSGRRG PNSIPGSTGR   60
TEVFIFSVDN LKANSSGTIK FGPSLSQCPA LSDGILKSYH RYKITSIRVK FQSHASAATS   120
GAIFVELDTA CKQSALGSYI NSFTISKTAS KSFRAEAING KEFQESTIDQ FWLLYKANGT   180
TTDTAGQFII TINVSMLTPK XVDSSTPEPK PAPEPTPAPQ PTPTPQPTPE PTPAPVPKRF   240
FEYVGTPTGV ISTRENSDSI SVSKLGGQSM QYIENEKCES KVIDSFWSTN NNVSAQAAFV   300
FPVPEGSYSV NISCEGFQSV DHIGGNEDGY WIGLIAYSNS SGDNWGIGNY KGCSFKNFLA   360
TNTWRPGHKD LKLNDCQFTD GQIVERDGVI SFHVDATGCD ACFYLAAPKT MKTDKYNYVV   420
SYGGYTNKRM EFGTISVTFD ESDVEAERIA RHSETPARHN HILLSESYEE PLPTIIDQGL   480
CDVKTPEQEI VKVDEEDRQT VSTEPDIALQ EYEAATAEIP DAEEDVLPSK EQLSVKPVDS   540
SGTPLPKSKE PEVLGTYQGM NIYPEDVPPV ARQKLREAAK APSTMLYDKA PKGSKSILSR   600
FVEGNRSKAT PAAPTVSTTS NMTREQLREY TRIRNSLGVT AAKEYKAQFQ              650

SEQ ID NO: 47          moltype = AA  length = 667
FEATURE                Location/Qualifiers
source                 1..667
                       mol_type = protein
                       organism = Barley yellow dwarf virus kerII
SEQUENCE: 47
MNSVGRRRAS KNVRARSNRT VRPVVVVRTN PNGRRRRAPR RPRRGRANPI LGPAGRSEVF   60
VFSINDIKAN SSGVIKFGPD LSQCPALSSG ILKSYHRYKI SNVKIEFKSH ASSTTVGAMF   120
IELDTACTQS TLGSYINSFT LSKSGTKTFN AQQIAGKEFR ETSVNQFYLL FKANGVTSDT   180
AGQFIITLRV SNMTPKXVDS STPGPGPKPK PDPTPTPAPE PKTPKRFFEF IGTPSGVIQT   240
RESSDSISVS KLGDQTFQKI ENEKSNDVFL SSYWQYSNSV YAQAAFVIPI YQGSYSVNIS   300
CEGMQSVDHI GGEQDGYWIG LIAYSNSTDD VWGVGNYQGC TITKYLVTNS WRPGHQDLKL   360
NDCAFDKGQI VERDAVLSFH VEAVGDNPSF YLLAPKTQKT DKYNYVVSYG GYTNKKMEFG   420
TIAITCDESD VEALRNARHA NYPIKENHQE LYHGSGTLLP AYSPDRVEVY PDITSSERTV   480
QPRPSEEPKF RDIQNQEELS SLFDLYDLAT SEIPDAREDV LPTKQEMSKK PIDSLGTEIP   540
RPRSMSPEYP RPRSRSPEYP RPRSRSPEPI GTYHGQNIYD DDVPKQVAER LREAAELPST   600
MLYNRKPKNR NSSFLSRFIE QNKSPDATAP SEATTSRMTR DQLKEYTRVR NQYGLTAAKQ   660
YKASLGQ                                                            667
```

-continued

```
SEQ ID NO: 48              moltype = AA  length = 680
FEATURE                    Location/Qualifiers
source                     1..680
                           mol_type = protein
                           organism = Rose spring dwarf-associated virus
SEQUENCE: 48
MSTVVVRQQA RNNSRRNGQA QQAQGRSRQP NKARPVVVQV QPSRNGRRPR RRGGRRSSRR   60
RGSRMASSRS HWEDYKFTIN NLKASDAGVV KFGPSISQCS ALKSGIFKSF HEFKITNLNV  120
KYITHAASTT SGAFAVEVDT SCTQTTLKSY LQTVPVAKCG QFSWPAGKIR GTGWLPTPDP  180
DKTPVDKDNQ FFLLYAGNGP SSVAGQFVIT ARCWFQSPRE XRDAAPAPSP SPPSPTPAPT  240
PAPTPQPERF FVYAGVPGVD IQTRETDDSI IVGRLNSERL RYVEDEQQTL VDIRADWYSN  300
NSVEAVPMLL FDLEEGSWSV DAECQGYQAV TAVGGSEDSN WLGFIAYNNA NGATWNVGEY  360
NNVKITKLLN TSSWKKGHKD VVLNGCHFND GQIIERDSTM SFHCEVGHGG GTILLVAPPV  420
CKSDKYNYVV SYGEYTTKHM EFGSIAICFD EKNDGARAGK FLGAPFPRAG HVVREQQTEI  480
ARFPAGSDVP IVKISDNDFA TSTQPAAHIL PVPSSVQLPD DPVSKKVRSW IENSSEDLRL  540
AREAEQTDSD WEPLPPPAPP PGPRQLPTDT SGATQAIRNQ ILRDHTQPYS GPGTPPVFDD  600
IEDTRSTTRT ESSRRSFLSG VLRPQLKPKS NLRPTSSLPR KLTADQEARV KAVRESFGSA  660
AAKRLRDEFL EGKVSPDQIY                                             680

SEQ ID NO: 49              moltype = AA  length = 647
FEATURE                    Location/Qualifiers
source                     1..647
                           mol_type = protein
                           organism = Cherry associated luteovirus
SEQUENCE: 49
MPKGKKGKGK GRKGKKNGRN RAASVAKSVV VNVQPGRGGG TGRGNARGNR IPNPGPGDRL   60
DRFTFTVDDL KANDSGTIKF GPSLSQYANF SNGILRSFHE YKITNLTVKF VSYASSTTSG  120
AFAIEIDTSR KQSDIRSRII SFPVAKGFTR SFQSKVIRGL IWHPTTEDQF FLIYKGNGKA  180
EIAGQFNISF TVNFQGPQXV VEAPQPSPTP EPTSPPPPPQ PTPCKQEKFY CYAGVPTATI  240
QTRENDESII LKSLGSQEFR YMEDDYQSTR YLQSTWYSQN NVQATPMIVV PLDEGDWYVD  300
IVCEGYQAVD AIGGDXDKKW LGFIAYNDDE QSNWNVGNYR NVVCSELLVT SSWKFGHKDL  360
VLNNCNFQRG QVIERDSVIT CKVKSGDGGG SFFLVGPPVM KTEKYNYVVS YGGYTDKTME  420
LGSVTIAIDE RAAGAAGVGI RAKRNNNCFE SHVPMSMPQL TIPDSVLDVV PSRDLIASSL  480
PPLPPNRKPA RQLIVHDPVN DWLTNHNPYN ISQTRQDVLD NESREWREGH HLGRVATQNE  540
VYRPEQDIVI FKQRDDQEAV VNDTVTQPVP STQAVDTLNS NNPPAAPYLA QGDIGPSQVQ  600
ARLMQEALER VRSQYDSGEI ETSSVAGSTS SRRSVLGGSL FGKRKGR               647

SEQ ID NO: 50              moltype = AA  length = 526
FEATURE                    Location/Qualifiers
source                     1..526
                           mol_type = protein
                           organism = Nectarine stem pitting associated virus
SEQUENCE: 50
MSQRNRRSQN AGWLPPMRQQ PPRWSSQRQG APAPRIVYVT GPPVQPKKAA KKKSPPSKQP   60
QPTSPFPAFK FTIDDLKGDA SGVLKFGPKL DQYQAFVNGI MKSFHDYRIS SVVIRYVSNA  120
ASTTPGAMAF EIDTSCTQTE LSSKVMSSPL NRSFTKTFSG PTIRGNLWLN TKQEQFWLLY  180
KANGAKSDIA GQFIITLHTH WQNPKSXRDD APPPEPTPCP PSPTQSRFWG YEGVLQSVIS  240
TRTHDDFVHP KPLSFCSMYK WEDENWTKEN FTANYSRNDS DEAFPYVLIP CSPGSFSVYV  300
ECQGFMVVKA RSGNYNGHWL GCVAYNVNRS GWVAQEYSGC KITNYKVSHT FVSGHPDVVL  360
NDCHFHDDQG VECDSIISFH LDCDVDGFWA LQPPPIQKND HYNYVVSYSD WTDKTLEWGS  420
VSISVDEVNQ GACTAIRGKQ EIRETLTSNY TAPAVAGGSV HFEKENSDKP VEIVKDNTPL  480
PEYMKETPRS VATTVPPWPP QPSVWRKPTS AAPTKKSNSF LGFRKG                526

SEQ ID NO: 51              moltype = AA  length = 722
FEATURE                    Location/Qualifiers
source                     1..722
                           mol_type = protein
                           organism = Soybean dwarf virus
SEQUENCE: 51
MVAVSNVAIQ RRRTRRAARR APRVQLMAVP TVTSRPQRRG RQRRRRRNNR GGSFISGGSG   60
KAHTFVFSKD GINGSSKGSI TFGPSLSECK PFSDGILKAY HEYKITSILL QFITEASSTS  120
SGSIAYELDP HCKYSEIQSL LNKFSITKSG SKRFPTRAIN GLEWHDTSED QFKIHYKGNG  180
ESKIAGSFKI SINVLTQNAK XVDGEPGPKP GPDPAPQPTP TPEPTPAKHE RFIAYTGTLS  240
TLISARQSSD SISLYSIRSQ RIRYIEDENS SWTNIDAKWY SQNSVEAIPM FVYPVPEGTW  300
SIEISCEGYQ AASSTSDPHR GKCDGMIAYD DDSSKVWNVG QQNNVTITNN KADNDWKYGH  360
PDLTINGDRF DQNQVVEKDG IISFHLVTTG PNASFFLVAP AVKKTAKYNF CVSYGDWTDR  420
DMEFGMVSVV LDEHLEGARS SQYVRKTPRS GHVGVNRSHR LQDNFVPTEY VSDEDSSSNS  480
SIVSNRPSTP DNDSDAKFAE SMKGKLPSQT KLPPKGFLSQ LSTKEKKEIS NSKPSNVEGL  540
VGPLVAAYGY PSQTGVHDAA REILQAKEAA ENLAELERDL KEINKLEPPD VIVQEEIPDF  600
VPPSEKILKE DDPDYVPPIW HNADQAVLVS SYEPPDWSRP AYESGDPPKK TGTLKGTLSK  660
LGGSLRSGES SLRGSLRKTQ DQTDLDNKLS KLSVIQRSRY QRILNNLGKM RARTYIDGLD  720
LD                                                               722

SEQ ID NO: 52              moltype = AA  length = 722
FEATURE                    Location/Qualifiers
source                     1..722
                           mol_type = protein
                           organism = Bean leafroll virus
SEQUENCE: 52
```

```
MVARGKRVVV RQLQTRARRR LPVVLATAPV RPQRKRRQRG RNNKSRGGNG FARRSSQVHE   60
FVFSKDNLNG NSKGSITFGP SLSECKPLAD GILKAYHEYN ITNVELAYIT EASSTSSGSI  120
AYELDPHLKN TTIQSKINKF SITKSEKKKF SRKAINGQAW HDTSEDQFRI LYEGNGDAKI  180
AGSFRVTIKV LTQNPKXVDG EPDPPGPGPD PPPPTPAPTP QPQPTPKHER FIVYTGVPES  240
RISAQSTDDS ISVYSLQNQR LRYIEDENAN WTNIEARWYS NNNVKATPMF IFPVPQGKWS  300
VEISTEGYQP TSSTTDPNNG KCDGLIAYSD DDKTDVWNVG VQKNITLSNN KADNTWKYGH  360
PDLEINNCKF NNRQVLERDA YISPHVETTG PNASFFLVAP PVQKTARYNY AVSYGAWTDR  420
MLEFGSVTVA LDEHLEGGNS SRYIRRSPRP GHLESTRTYD LHLLPHMDDL IAANTTAVVD  480
GYGSSISIDR QVLVAVDNHI VDSGDETDDL PGYSSSSSEA PKLPAVNQTK LPPKGFLSRL  540
RESEIEEIAD KPTEITTPEV RQLADATHQP FAAGMYNDAF ERLSINEKKR NFDSVKDDIA  600
EIERTLPKEE YRVPKLPRIK PASEVDNDHY GESQQTLAEI ERRNVWASKD DAVAVESPPP  660
GYPLGPIEAR ELMPVEWSRP DYEPPKPKKS LFGRLKSQAK VEANPSSPRN DIRRSSFSSF  720
RR                                                                722

SEQ ID NO: 53           moltype = AA   length = 672
FEATURE                 Location/Qualifiers
source                  1..672
                        mol_type = protein
                        organism = Apple associated luteovirus
SEQUENCE: 53
MNSAAVRRRA RGTARRRNGR RVIRATPRLV VVPGLGRRRR NGRPRPRTNR IGSARLTRAP   60
EEFTFTVDDL RANASGIIKF GPSLSQCAAI SSGVLKSYLE YKIISVAIQY VTNASSTTAG  120
AFSLEVDTSR TRSALDSRVI SFPVSKNYSR SFNASLIKGL SWVPTTDDQF HLLYKGNGSS  180
DIAGQFIIRT RIVLQGPKXV DAAPSPSPDP PAPQPSPTPK QERFFAFSGV PKLTVRTREN  240
SDSIILPNEF PNQVLRYLED DKQEDRWVSA RWYTSNNMQA VPMLIFDVPQ GVWFVDFMCE  300
GYQALSAVGG AEDQKWMGFV AYNDNNSDSW NIGVYNSVAI TDLNLLTKWK LGHKDMELNG  360
CHAKDGQVIE RDAVGSCKVD ASGGAGRLFI VPPPIMKTEK YNYCVSYQDY TDKNLDLGFV  420
TVCFDERDGA QRACNLLHRA AWLSGNDQIH AWATPAPLQD YLSDLDDAPS DVESEPKTGT  480
DKITPLQESD KITPEPVSDK VTQADSRVIS WLNNDTTNDT ETDTDYSKLK PPLPPKQQVE  540
LTRENVADIV RKDILRDTTL PFSRFSGDPL TERAEEDARS MRSSGSIGGR SITPSLSGSL  600
GRGVLKSGPS VPHIKHIPTG KPASLFVKID KKSFLTDAER AEYDKIRASF SKARADEYLD  660
FIFNARNTSS SN                                                     672

SEQ ID NO: 54           moltype = AA   length = 781
FEATURE                 Location/Qualifiers
source                  1..781
                        mol_type = protein
                        organism = Apple luteovirus 1
SEQUENCE: 54
MVVRRRQPVR RNIRRRRNGP RRFAAPPRVV VVPGRPRRRR RNGRTNPRAN RGRITFSSRP   60
AEVFTFTVDD LKAGSTGILK FGPGLSQCAA VSGGVLKSYH QYKIIGLTCG YVTNASSTTA  120
GAFALEIDTT CSRSALESRI ISFPVTKNTS KFFPPGVING QNWVSSDTNQ FFLLYGGNGS  180
KTEIAGQLLI KVMITLQGPK XVDAAPSPSP KPDDPKPSPPP PSPKPAKERR FFAYSGIPKT  240
KIKTKGNDDS IIASSNLEQQ VFRYIEANNQ KDVTLNARWY STSTVKNKPM IVFDVPAGDW  300
FVDFLCEGYM PIEAIGGSED QKWMGIVAYN NDTADIWSVG VYDNVSITEL NITSSWKLGH  360
KDLELNGCHF HDGQVVERDS IGSCKVSSNT GGSLFLVAPS IMKTAKYNYC VSYGDYTDKT  420
LEFGFVSMVF DERDGANTAV PHIRRELKNV KYLRPSPVKL NDGGDYIDEV QKPIAAAPPS  480
AKRPTSSRFV VAPEPKPEPA PEPKPEPAPE PQPEVSQSPQ REPAVPTKEP AVPTNEPFWP  540
ISVIDSIHVA EVTTSDESKI RVPLETRDPD GNILSLHPGG LNAMGRDLQQ FERDAVYKMW  600
VEGQAEDIRR KQIETDAASA RSISENDYRQ INQEIRAAEL PNQPNFVYRD DPIVKQNSTS  660
DFIAARRADF DEQSVSDLKS NASTRTITGN LGGGKLKKKA NDLDDVEDKI LKALPEIDYK  720
PSEILGVKAR YHGGCGKWRD TFDSSMNCRC WMPTLEWQQV DFQYKGKASK NEGKSIISWP  780
P                                                                781

SEQ ID NO: 55           moltype = AA   length = 670
FEATURE                 Location/Qualifiers
source                  1..670
                        mol_type = protein
                        organism = PEACH ASSOCIATED LUTEOVIRUS
SEQUENCE: 55
MPTKKGKGKG KKGKKNGKGG NSGANAKSVV VNVQSGGRGR TGRSASGGNR VAGSGPGDHS   60
NRFSFTVDDL NSASSGILKF GPNLSQYTNF SNGILKSFHE YKITNLTVKY VSYASSTTSG  120
AFAIEIDTSR KQTDLKSRII SFPVSKGFSR GFQARVLRGL LWHPTSEDQF WLVYKGNGKS  180
TDIAGQFVIS FNVNFQGPCX VDAAPQPSPT LDPTPPTPPP EPTPVKQERF ICYAGVPRAT  240
IQTRENDESI ALKRLEDQNL RFLEDDYQST TSIASCWYSQ NNVQATPMFI FPLDEGDWYV  300
DIVCEGYQAV MAIGGDEDKK WLGFIAYNDD EQANWNVGNY RNVVCSELLV TSSWKFGHKD  360
LVLNGCNFQR GQVIERDSVI TFKVKSGNGG GEFFLVGPPV MKTEKYNYVV SYGGYTDKTM  420
EFGSINDCAD ERADGARGAG IRAKLGDLDH HNWNLCDLPP LQIPDVKLDV VPSVNKVNNS  480
PPIGFNADRP PPIPNPSQLP PSSSSDEKLR KKIMDWQLDS GPMKNDPDRD DAIAREPPEW  540
REGHHLGRTH TRAEIFPRET SMVIIPQQDE TPEVQADTVV TSVATEAVQV TTVPVSAQPA  600
YISQLPPSWR QDKPPMVLSQ RQMELANKAL NSAMSGEFSD DDETHSVAQS TASNRSLFGG  660
GLFGKKKGRR                                                        670

SEQ ID NO: 56           moltype = AA   length = 493
FEATURE                 Location/Qualifiers
source                  1..493
                        mol_type = protein
                        organism = Pea enation mosaic virus 1
SEQUENCE: 56
```

```
MPTRSRSKAN QRRRRPRRVV VVAPSMAQPR TQSRRPRRRN KRGGGLNGSH TVDFSMVHGP    60
FNGNATGTVK FGPSSDCQCI KGNLAAYQKY RIVWLKVVYQ SEAAATDRGC IAYHVDTSTT   120
KKAADVVLLD TWNIRSNGSA TFGREILGDQ PWYESNKDQF FFLYRGTGGT DVAGHYRISG   180
RIQLMNASLX GDDAPPSPGP DPGPQPPPPP PPSPTPVGAR FWGYEGVPES RMISERNDHD   240
IDVKPLSFIT MYKWEDESWT SVKLSASYLQ NDQVEATPYF LIPSSKGKFS VYIECEGFQA   300
VKSIGGKSDG CWGGLIAYNR KKDGWQARAY TGTVLSNYRS TTTVINGHPD CEVNDCKFKP   360
DRGVESDLIC SFHLEAEEDS YWALQAPPIQ KSSDYNYVVS YGGYTEKSIE WGSVSISIDE   420
VNQTASASPW RGRARKLAIL QETAVPPPFP PGGVMDYHLG DREGDQTGTS EKGLLKKPPL   480
PKWDLQRSRS PLD                                                     493

SEQ ID NO: 57           moltype = AA  length = 494
FEATURE                 Location/Qualifiers
source                  1..494
                        mol_type = protein
                        organism = Citrus vein enation virus SEQUENCE: 57
MVSRNQRRRN RPRRMRRRQA PNRVVVMGNN PTRSRRRNAP ARRRRAVNRS TGEMRPYHLY    60
GLKCNDKGYL TFGPSGQTPS LGGGILKAFS EYKITQLRVQ WKAQASSTAA GSMAIQIGLG   120
TSLTALDNRA ISFKLTSSGQ RVFTARDLGG DGRMYNSSNE DQFRLAYQGN GDSTLGGDLL   180
CFFRLETRLP KXVDADPPSP PSPEPSPEPP PQPPAPTPAR CRFWGYEGIP SVSVSSAEND   240
RDVEVRALST IDLYKFEDEN WSTVHLRAGY STNDRVHAQP YIVFPIEKGE FDVYIECEGF   300
QAVKSIGGKA DGSWEGLIAY STSDSGWLVS EYVGVSITKY QSSTAFVGGH PDTRLNDCSF   360
KQDRAVECDI VCSFRLSADS DNAKWLLYAP WIQKASEYNY IVSYGAYTEK ICELGSISVN   420
IDEVNEQQGP SPASKRWGRR RLDRERQLVK TLVNQPSSDL EEAKETGSLR APGWRERVEK   480
EKKKEDKPSR FSWR                                                    494

SEQ ID NO: 58           moltype = AA  length = 492
FEATURE                 Location/Qualifiers
source                  1..492
                        mol_type = protein
                        organism = Alfalfa enamovirus 1

SEQUENCE: 58
MPTKSKAPQR RRRQPKRKAV VADLVVQPRA RPRRPRRRRN RRGSGQNGSH TVDFSMVHGP    60
FNGNSTGTIK FGPSSDCQCV KGNLNAYQKY RITWLKVVYQ SEAASTDRGC IAYHVDTSTT   120
KRATDVVLLD TWNVRSNGSA TFGREILGDQ PWYESNKDQF NFLYRGTGGS DVAGHFRING   180
KIQLMNASLX GDDAPPSPGP DPGPPPPPPP SPAPKGARFW GYEGTPELRI ISERNDNFID   240
VKSLSTVRLF KWEDENWSTV TLSAAYIKND RSEAIPYFLI PSSKGSFSVY IECEGFQAVK   300
HIGGTADGCW CGLVAYDRSK DGWAARMYSG CNITNYRASS TTVGGHPDAE LNDCKFRPER   360
CVESDFSCSF HMECEDDGYW ALQAPPIQKS NDYNYIVSYG NYTEKVLEWG TVSISIDEVN   420
SNGTASPRSL RGRPRKPVVL QETAVPPPIP PGGAMDCPVG NREDDQTGTY GSRPLRRSNP   480
RWDPFGSRNP WS                                                      492

SEQ ID NO: 59           moltype = AA  length = 544
FEATURE                 Location/Qualifiers
source                  1..544
                        mol_type = protein
                        organism = Grapevine enamovirus 1

SEQUENCE: 59
MVARSKKAGK KKSAGPGNRR RLQPRARQMV VVSTQRPRKP RPRRTRGRGS QGGGLNAGVN    60
FTFLVNSFAG NASGTIKFGP NLTESSAFVG VLGSFQRYRI VSLQVHYVTE ASKMDRGCIA   120
YHVDTSCSMR ASGLLPTTSW PVTQSALKTY GAGVLGDQPH YEHTKEQFWF LYKGNGSSDI   180
AGHLRLTIRV VFTNTLXYLD SSPPSPTPPP SPRPPAETAL LIGYCGTPTC SIATRQSKES   240
IIVGKTEMIQ LFRWQDDRWE TVSIPIEQTR LSDRDTHLAR FQIERTGTFR IHIQCEGLQC   300
VADAKAEEEE EWKGIITYSP TGGVFSVVPL GDSVLSDKQQ STTLTKGHKD SSINGDKLSG   360
QVVEVDWTCS FDVLCTSPNT GFGMFFPDIM KDQHYNFVVS YGDYTWKTME YGTISIDIDQ   420
VNDSQGRPCD SRRGKGVPRH WKRAIRGKEQ PYNAPGPAGD RKEGSAQVPV SIAPMAEPTV   480
LPRTMTPPAP MVMEPVRRTG IEVAPIAPPS PPPLPPVPKP PVESNQPAAS PQKKKSSSSP   540
WIRF                                                              544
```

What is claimed is:

1. An isolated protein comprising the protein sequence of SEQ ID NO: 5, SEQ ID NO: 6, SEQ ID NO: 7, SEQ ID NO: 8, or SEQ ID NO: 12.

2. The isolated protein of claim 1, further comprising a green-fluorescent protein (GFP), a yellow fluorescent protein (YFP), strep tag, FlAsH tag, or polyhistidine (HIS) tag.

3. A vector comprising a nucleic acid encoding a protein having SEQ ID NO: 5, SEQ ID NO: 6, SEQ ID NO: 7, SEQ ID NO: 8, or SEQ ID NO: 12.

4. A recombinant potato leaf roll virus comprising the protein of SEQ ID NO: 5, SEQ ID NO: 6, SEQ ID NO: 7, SEQ ID NO: 8, or SEQ ID NO: 12.

5. A modified protein comprising a polypeptide having at least 98% identity to SEQ ID NO: 2 or 98% identity to SEQ ID NO: 3, and wherein the modified protein comprises an amino acid substitution in any one of residues 137, 138, 139, 140, 141, 142, 143, 144, or 145.

6. The modified protein of claim 5, wherein the polypeptide has at least 98% identity to SEQ ID NO: 2 and wherein the modified protein comprises an amino acid substitution in any one of residues 137, 138, 139, 140, 141, 142, 143, 144, or 145.

7. The modified protein of claim 6, wherein the amino acid substitution comprises an alanine substitution.

8. The modified protein of claim 5, wherein the polypeptide has at least 98% identity to SEQ ID NO: 3 and wherein the modified protein comprises an amino acid substitution in any one of residues 137, 138, 139, 140, 141, 142, 143, 144, or 145.

9. The modified protein of claim 8, wherein the amino acid substitution comprises an alanine substitution.

10. A transgenic plant comprising a heterologous nucleic acid encoding SEQ ID NO: 5, SEQ ID NO: 6, SEQ ID NO: 7, SEQ ID NO: 8, or SEQ ID NO: 12.

11. The transgenic plant of claim 10, wherein the heterologous nucleic acid is operatively linked to a plant promoter sequence.

12. A plant comprising a protein having the amino acid sequence of SEQ ID NO: 5, SEQ ID NO: 6, SEQ ID NO: 7, SEQ ID NO: 8, or SEQ ID NO: 12.

13. A method of controlling aphids, comprising the step of:

exposing an aphid to a protein having an amino acid sequence: 1) at least 98% identical to SEQ ID NO: 2 and wherein the protein comprises an amino acid substitution in at least one of residues 137, 138, 139, 140, 141, 142, 143, 144, or 145, and the protein further comprises a green-fluorescent protein (GFP), a yellow fluorescent protein (YFP), strep tag, FlAsH tag, or polyhistidine (HIS) tag operably linked to the protein; or 2) at least 98% identical to SEQ ID NO: 3 and wherein the protein comprises an amino acid substitution in any one of residues 137, 138, 139, 140, 141, 142, 143, 144, or 145, and the protein further comprises a green-fluorescent protein (GFP), a yellow fluorescent protein (YFP), strep tag, FlAsH tag, or polyhistidine (HIS) tag operably linked to the protein, thereby inducing increased mortality in the aphid.

14. The method of claim 13, wherein the protein has an amino acid sequence of SEQ ID NO: 5, SEQ ID NO: 6, SEQ ID NO: 7, SEQ ID NO: 8, or SEQ ID NO: 12 and the protein further comprises a green-fluorescent protein (GFP), a yellow fluorescent protein (YFP), strep tag, FlAsH tag, or polyhistidine (HIS) tag operably linked to the protein.

15. The method of claim 13, wherein the exposing step comprises an aphid feeding on a plant containing the protein.

16. The recombinant potato leaf roll virus of claim 4, further comprising a green-fluorescent protein (GFP), a yellow fluorescent protein (YFP), strep tag, FlAsH tag, or polyhistidine (HIS) tag operably linked to said protein.

17. The modified protein of claim 5, further comprising a green-fluorescent protein (GFP), a yellow fluorescent protein (YFP), strep tag, FlAsH tag, or polyhistidine (HIS) tag.

18. The transgenic plant of claim 10, wherein the heterologous nucleic acid further encodes a green-fluorescent protein (GFP), a yellow fluorescent protein (YFP), strep tag, FLASH tag, or polyhistidine (HIS) tag operably linked to said protein.

*     *     *     *     *